United States Patent
Low et al.

(10) Patent No.: US 12,144,850 B2
(45) Date of Patent: Nov. 19, 2024

(54) METHODS AND COMPOSITIONS FOR CAR T CELL THERAPY

(71) Applicants: PURDUE RESEARCH FOUNDATION, West Lafayette, IN (US); ENDOCYTE, INC., West Lafayette, IN (US)

(72) Inventors: Philip Stewart Low, West Lafayette, IN (US); Haiyan Chu, West Lafayette, IN (US); Yong Gu Lee, West Lafayette, IN (US)

(73) Assignees: Purdue Research Foundation, West Lafayette, IN (US); Endocyte, Inc, West Lafayette, IN (US)

( * ) Notice: Subject to any disclaimer, the term of this patent is extended or adjusted under 35 U.S.C. 154(b) by 617 days.

(21) Appl. No.: 16/092,054

(22) PCT Filed: Apr. 7, 2017

(86) PCT No.: PCT/US2017/026618
§ 371 (c)(1),
(2) Date: Oct. 8, 2018

(87) PCT Pub. No.: WO2017/177149
PCT Pub. Date: Oct. 12, 2017

(65) Prior Publication Data
US 2019/0091308 A1 Mar. 28, 2019

Related U.S. Application Data

(60) Provisional application No. 62/323,971, filed on Apr. 18, 2016, provisional application No. 62/320,183, filed on Apr. 8, 2016.

(51) Int. Cl.
| | |
|---|---|
| A61K 39/00 | (2006.01) |
| A61K 9/00 | (2006.01) |
| A61K 35/12 | (2015.01) |
| A61K 35/17 | (2015.01) |
| A61K 39/395 | (2006.01) |
| A61K 47/54 | (2017.01) |
| A61K 47/55 | (2017.01) |
| A61K 48/00 | (2006.01) |
| A61P 35/00 | (2006.01) |
| C07K 14/705 | (2006.01) |
| C07K 14/725 | (2006.01) |
| C07K 16/44 | (2006.01) |
| C12N 15/86 | (2006.01) |

(52) U.S. Cl.
CPC ........ *A61K 39/0011* (2013.01); *A61K 9/0019* (2013.01); *A61K 35/12* (2013.01); *A61K 35/17* (2013.01); *A61K 39/39558* (2013.01); *A61K 47/551* (2017.08); *A61K 47/555* (2017.08); *A61K 48/005* (2013.01); *A61P 35/00* (2018.01); *C07K 14/7051* (2013.01); *C07K 14/70517* (2013.01); *C07K 16/44* (2013.01); *C12N 15/86* (2013.01); *A61K 2039/505* (2013.01); *A61K 2039/5156* (2013.01); *C07K 2317/622* (2013.01); *C07K 2317/73* (2013.01); *C07K 2317/92* (2013.01); *C07K 2319/02* (2013.01); *C07K 2319/03* (2013.01); *C07K 2319/33* (2013.01); *C12N 2740/15043* (2013.01); *C12N 2740/16043* (2013.01)

(58) Field of Classification Search
CPC ...... A61P 35/00; C07K 14/7051; C07K 16/44
See application file for complete search history.

(56) References Cited

U.S. PATENT DOCUMENTS

| | | |
|---|---|---|
| 4,690,915 A | 9/1987 | Rosenberg |
| 4,946,778 A | 8/1990 | Ladner et al. |
| 5,087,616 A | 2/1992 | Myers et al. |
| 5,116,964 A | 5/1992 | Capon et al. |
| 5,202,238 A | 4/1993 | Fell, Jr. et al. |
| 5,216,132 A | 6/1993 | Basi |
| 5,359,046 A | 10/1994 | Capon et al. |
| 5,372,930 A | 12/1994 | Colton et al. |
| 5,482,856 A | 1/1996 | Fell, Jr. et al. |
| 5,514,582 A | 5/1996 | Capon et al. |
| 5,525,503 A | 6/1996 | Rudd et al. |
| 5,538,866 A | 7/1996 | Israeli et al. |
| 5,670,148 A | 9/1997 | Sherwin et al. |
| 5,686,281 A | 11/1997 | Roberts |
| 5,712,149 A | 1/1998 | Roberts |

(Continued)

FOREIGN PATENT DOCUMENTS

| | | |
|---|---|---|
| CN | 102775500 | 11/2012 |
| CN | 106132436 A | 11/2016 |

(Continued)

OTHER PUBLICATIONS

Hennig et al. (Substance-P receptors in human primary neoplasms tumoral and vascualr localization. Int.J.Cancer:61, 786-792 1995. (Year: 1995).*

Lu, Y. et al., "Preclinical pharmacokinetics, tissue distribution, and antitumor activity of a folate-hapten conjugate-targeted immunotheraphy in hapten-immunized mice," Molecular Cancer Therapeutics, 2006, 5, 3258-3267.

International Search Report prepared for PCT/US2013/076986, mailed Apr. 28, 2014.

(Continued)

*Primary Examiner* — Amy E Juedes
*Assistant Examiner* — Brian Hartnett
(74) *Attorney, Agent, or Firm* — Schwegman Lundberg & Woessner, P.A.

(57) ABSTRACT

The present disclosure relates to methods of treating a patient with a cancer by administering to the patient a composition comprising CAR T cells and a small molecule linked to a targeting moiety by a linker. The disclosure also relates to compositions for use in such methods.

14 Claims, 27 Drawing Sheets

Specification includes a Sequence Listing.

(56) References Cited

U.S. PATENT DOCUMENTS

| | | |
|---|---|---|
| 5,714,147 A | 2/1998 | Capon et al. |
| 5,741,899 A | 4/1998 | Capon et al. |
| 5,747,292 A | 5/1998 | Greenberg et al. |
| 5,830,755 A | 11/1998 | Nishimura et al. |
| 5,834,256 A | 11/1998 | Finer et al. |
| 5,837,544 A | 11/1998 | Capon et al. |
| 5,843,728 A | 12/1998 | Seed et al. |
| 5,851,828 A | 12/1998 | Seed et al. |
| 5,858,740 A | 1/1999 | Finer et al. |
| 5,861,156 A | 1/1999 | George et al. |
| 5,906,936 A | 5/1999 | Eshhar et al. |
| 5,908,638 A | 6/1999 | Huber et al. |
| 5,912,170 A | 6/1999 | Seed et al. |
| 5,912,172 A | 6/1999 | Eshhar et al. |
| 5,914,109 A | 6/1999 | Zolla-Pazner et al. |
| 5,935,818 A | 8/1999 | Israeli et al. |
| 5,969,102 A | 10/1999 | Bram et al. |
| 6,004,781 A | 12/1999 | Seed |
| 6,004,811 A | 12/1999 | Seed et al. |
| 6,077,947 A | 6/2000 | Capon et al. |
| 6,083,751 A | 7/2000 | Feldhaus et al. |
| 6,103,521 A | 8/2000 | Capon et al. |
| 6,117,656 A | 9/2000 | Seed |
| 6,132,718 A | 10/2000 | Hansen et al. |
| 6,218,187 B1 | 4/2001 | Finer et al. |
| 6,261,787 B1 | 7/2001 | Davis et al. |
| 6,319,494 B1 | 11/2001 | Capon et al. |
| 6,392,013 B1 | 5/2002 | Seed et al. |
| 6,406,697 B1 | 6/2002 | Capon et al. |
| 6,407,221 B1 | 6/2002 | Capon et al. |
| 6,410,014 B1 | 6/2002 | Seed et al. |
| 6,410,319 B1 | 6/2002 | Raubitschek et al. |
| 6,432,403 B1 | 8/2002 | Philips |
| 6,521,602 B1 | 2/2003 | Patel et al. |
| 6,524,572 B1 | 2/2003 | Li |
| 6,699,972 B1 | 3/2004 | Roffler et al. |
| 6,753,162 B1 | 6/2004 | Seed et al. |
| 6,759,243 B2 | 7/2004 | Kranz et al. |
| 6,770,749 B2 | 8/2004 | Ellenhorn et al. |
| 6,953,668 B1 | 10/2005 | Israeli et al. |
| 7,037,647 B1 | 5/2006 | Israeli et al. |
| 7,049,136 B2 | 5/2006 | Seed et al. |
| 7,052,906 B1 | 5/2006 | Lawson et al. |
| 7,070,995 B2 | 7/2006 | Jensen |
| 7,105,159 B1 | 9/2006 | Israeli et al. |
| 7,217,421 B1 | 5/2007 | McArthur et al. |
| 7,265,209 B2 | 9/2007 | Jensen |
| 7,320,787 B2 | 1/2008 | Seed et al. |
| 7,348,004 B2 | 3/2008 | Peters et al. |
| 7,354,587 B1 | 4/2008 | Hansen |
| 7,354,762 B2 | 4/2008 | Jensen |
| 7,381,408 B2 | 6/2008 | Mezo et al. |
| 7,404,956 B2 | 7/2008 | Peters et al. |
| 7,435,596 B2 | 10/2008 | Campana et al. |
| 7,446,179 B2 | 11/2008 | Jensen et al. |
| 7,446,190 B2 | 11/2008 | Sadelain et al. |
| 7,446,191 B2 | 11/2008 | Jensen |
| 7,482,005 B2 | 1/2009 | Kim |
| 7,514,537 B2 | 4/2009 | Jensen |
| 7,569,663 B2 | 8/2009 | Tykocinski et al. |
| 7,572,891 B2 | 8/2009 | Belldegrun et al. |
| 7,618,817 B2 | 11/2009 | Campbell |
| 7,632,497 B2 | 12/2009 | Stavenhagen |
| 7,655,461 B2 | 2/2010 | Finn et al. |
| 7,666,424 B2 | 2/2010 | Cheung et al. |
| 7,723,111 B2 | 5/2010 | Hwu et al. |
| 7,741,465 B1 | 6/2010 | Eshhar et al. |
| 7,871,817 B2 | 1/2011 | Voss et al. |
| 7,906,620 B2 | 3/2011 | Eisenbach et al. |
| 7,919,079 B2 | 4/2011 | Simmons et al. |
| 7,939,059 B2 | 5/2011 | Yang et al. |
| 7,994,298 B2 | 8/2011 | Zhang et al. |
| 7,998,736 B2 | 8/2011 | Morgan et al. |
| 8,105,830 B2 | 1/2012 | Weidanz et al. |
| 8,148,154 B2 | 4/2012 | Cheung et al. |
| 8,163,887 B2 | 4/2012 | Hansen |
| 8,211,422 B2 | 7/2012 | Eshhar et al. |
| RE43,586 E | 8/2012 | Israeli et al. |
| 8,252,914 B2 | 8/2012 | Zhang et al. |
| 8,324,353 B2 | 12/2012 | Jensen |
| 8,389,282 B2 | 3/2013 | Sadelain et al. |
| 8,399,645 B2 | 3/2013 | Campana et al. |
| 8,409,577 B2 | 4/2013 | Thompson et al. |
| 8,450,112 B2 | 5/2013 | Li et al. |
| 8,465,743 B2 | 6/2013 | Rosenberg et al. |
| 8,486,911 B2 | 7/2013 | Okada et al. |
| 8,497,118 B2 | 7/2013 | Jensen |
| 8,741,306 B2 | 6/2014 | Belldegrun et al. |
| 8,802,374 B2 | 8/2014 | Jensen |
| 8,809,050 B2 | 8/2014 | Vera et al. |
| 8,822,196 B2 | 9/2014 | Rosenberg et al. |
| 8,822,647 B2 | 9/2014 | Jensen |
| 8,859,229 B2 | 10/2014 | Rabinovich et al. |
| 8,877,199 B2 | 11/2014 | Rader et al. |
| 8,906,682 B2 | 12/2014 | June et al. |
| 8,911,993 B2 | 12/2014 | June et al. |
| 8,932,830 B2 | 1/2015 | Peters et al. |
| 8,946,385 B2 | 2/2015 | Kawai |
| 8,956,860 B2 | 2/2015 | Vera et al. |
| 9,023,621 B2 | 5/2015 | Gurney et al. |
| 9,040,669 B2 | 5/2015 | Cheung et al. |
| 9,062,127 B2 | 6/2015 | Voss et al. |
| 9,074,000 B2 | 7/2015 | Scheinberg et al. |
| 9,089,520 B2 | 7/2015 | Brenner |
| 9,101,584 B2 | 8/2015 | June et al. |
| 9,101,609 B2 | 8/2015 | Tan et al. |
| 9,102,760 B2 | 8/2015 | June et al. |
| 9,102,761 B2 | 8/2015 | June et al. |
| 9,111,061 B2 | 8/2015 | Otsuka et al. |
| 9,133,436 B2 | 9/2015 | Riley et al. |
| 9,156,915 B2 | 10/2015 | Waldman et al. |
| 9,163,258 B2 | 10/2015 | Riddell et al. |
| 9,175,308 B2 | 11/2015 | Shiku et al. |
| 9,181,527 B2 | 11/2015 | Sentman |
| 9,211,321 B2 | 12/2015 | Karlsson-Parra et al. |
| 9,212,229 B2 | 12/2015 | Schönfeld et al. |
| 9,220,728 B2 | 12/2015 | Sadelain et al. |
| 9,226,936 B2 | 1/2016 | Hu et al. |
| 9,233,125 B2 | 1/2016 | Davila et al. |
| 9,242,014 B2 | 1/2016 | Kipps et al. |
| 9,266,960 B2 | 2/2016 | Morgan et al. |
| 9,272,002 B2 | 3/2016 | Powell, Jr. et al. |
| 9,273,283 B2 | 3/2016 | Sentman |
| 9,279,008 B2 | 3/2016 | Scholler et al. |
| 9,334,330 B2 | 5/2016 | Birkle et al. |
| 9,345,748 B2 | 5/2016 | Morgan et al. |
| 9,352,036 B2 | 5/2016 | McBride et al. |
| 9,359,447 B2 | 6/2016 | Feldman et al. |
| 9,365,641 B2 | 6/2016 | June et al. |
| 9,393,268 B2 | 7/2016 | Waldman et al. |
| 9,393,292 B2 | 7/2016 | Brenner |
| 9,394,364 B2 | 7/2016 | Ho et al. |
| 9,394,368 B2 | 7/2016 | Brogdon et al. |
| 9,402,865 B2 | 8/2016 | Powell et al. |
| 9,402,888 B2 | 8/2016 | Hildegund et al. |
| 9,408,904 B2 | 8/2016 | Wright et al. |
| 9,409,992 B2 | 8/2016 | Ho et al. |
| 9,409,994 B2 | 8/2016 | Ho et al. |
| 9,416,190 B2 | 8/2016 | Ho et al. |
| 9,422,351 B2 | 8/2016 | Scholler et al. |
| 9,434,935 B2 | 9/2016 | Spencer et al. |
| 9,446,105 B2 | 9/2016 | Powell et al. |
| 9,447,194 B2 | 9/2016 | Jensen |
| 9,453,075 B2 | 9/2016 | Cheung et al. |
| 9,464,140 B2 | 10/2016 | June et al. |
| 9,469,684 B2 | 10/2016 | Finn et al. |
| 9,476,028 B2 | 10/2016 | Karlsson-Parra et al. |
| 9,481,728 B2 | 11/2016 | June et al. |
| 9,487,800 B2 | 11/2016 | Schonfeld et al. |
| 9,492,499 B2 | 11/2016 | Jaynes et al. |
| 9,492,529 B2 | 11/2016 | Karlsson-Parra et al. |
| 9,493,740 B2 | 11/2016 | Brenner et al. |
| 9,499,629 B2 | 11/2016 | June et al. |
| 9,499,855 B2 | 11/2016 | Hyde et al. |

(56) References Cited

U.S. PATENT DOCUMENTS

| | | |
|---|---|---|
| 9,511,092 B2 | 12/2016 | Campana et al. |
| 9,518,123 B2 | 12/2016 | June et al. |
| 9,522,955 B2 | 12/2016 | Rosenberg et al. |
| 9,540,445 B2 | 1/2017 | June et al. |
| 9,540,448 B2 | 1/2017 | Scheinberg et al. |
| 9,561,291 B2 | 2/2017 | Kovesdi et al. |
| 9,562,087 B2 | 2/2017 | Ring et al. |
| 9,567,399 B1 | 2/2017 | Campbell et al. |
| 9,572,836 B2 | 2/2017 | June et al. |
| 9,572,837 B2 | 2/2017 | Wu |
| 9,573,988 B2 | 2/2017 | Brogdon et al. |
| 9,574,014 B2 | 2/2017 | Williams et al. |
| 9,587,020 B2 | 3/2017 | Wu et al. |
| 9,587,237 B2 | 3/2017 | Hyde et al. |
| 9,597,357 B2 | 3/2017 | Gregory et al. |
| 9,605,049 B2 | 3/2017 | Campana et al. |
| 9,623,049 B2 | 4/2017 | Eshhar et al. |
| 9,624,292 B2 | 4/2017 | Voss et al. |
| 9,624,306 B2 | 4/2017 | Morgan et al. |
| 9,629,877 B2 | 4/2017 | Cooper et al. |
| 9,636,388 B2 | 5/2017 | Lawman et al. |
| 9,636,416 B2 | 5/2017 | Peters et al. |
| 9,642,906 B2 | 5/2017 | Ramos et al. |
| 9,650,428 B2 | 5/2017 | Sampath et al. |
| 9,657,105 B2 | 5/2017 | Forman et al. |
| 9,662,405 B2 | 5/2017 | Waldman et al. |
| 9,663,756 B1 | 5/2017 | Lipkens et al. |
| 9,663,763 B2 | 5/2017 | Sentman |
| 9,669,058 B2 | 6/2017 | Li et al. |
| 9,670,281 B2 | 6/2017 | Lim et al. |
| 9,676,867 B2 | 6/2017 | Marasco et al. |
| 9,688,740 B2 | 6/2017 | Choi et al. |
| 9,688,760 B2 | 6/2017 | Kufer et al. |
| 9,694,033 B2 | 7/2017 | Yi et al. |
| 9,701,758 B2 | 7/2017 | Cooper et al. |
| 9,708,384 B2 | 7/2017 | Scholler et al. |
| 9,714,278 B2 | 7/2017 | June et al. |
| 9,717,745 B2 | 8/2017 | He |
| 9,725,519 B2 | 8/2017 | Masuko et al. |
| 9,733,245 B2 | 8/2017 | Kawai |
| 9,738,726 B2 | 8/2017 | Dimitrov et al. |
| 9,745,368 B2 | 8/2017 | Milone et al. |
| 9,765,142 B2 | 9/2017 | Dimitrov et al. |
| 9,765,156 B2 | 9/2017 | June et al. |
| 9,765,330 B1 | 9/2017 | Niazi et al. |
| 9,765,342 B2 | 9/2017 | Kochenderfer |
| 9,777,061 B2 | 10/2017 | Ebersbach et al. |
| 9,777,064 B2 | 10/2017 | Wang et al. |
| 9,783,591 B2 | 10/2017 | June et al. |
| 9,789,174 B2 | 10/2017 | Karlsson-Parra et al. |
| 9,790,267 B2 | 10/2017 | Kaplan |
| 9,790,278 B2 | 10/2017 | Sentman et al. |
| 9,790,282 B2 | 10/2017 | Orentas et al. |
| 9,790,467 B2 | 10/2017 | Kevlahan et al. |
| 9,796,783 B2 | 10/2017 | Agerstam et al. |
| 9,802,997 B2 | 10/2017 | Mahr et al. |
| 9,803,022 B2 | 10/2017 | Ho et al. |
| 9,808,486 B2 | 11/2017 | Georgiou et al. |
| 9,809,581 B2 | 11/2017 | Chen et al. |
| 9,815,901 B2 | 11/2017 | Brogdon et al. |
| 9,815,908 B2 | 11/2017 | Schonfeld et al. |
| 9,821,011 B1 | 11/2017 | Sentman |
| 9,821,012 B2 | 11/2017 | Wu et al. |
| 9,822,340 B1 | 11/2017 | Sentman |
| 9,828,399 B2 | 11/2017 | Tremblay et al. |
| 9,828,435 B2 | 11/2017 | Evans et al. |
| 9,833,476 B2 | 12/2017 | Zhang et al. |
| 9,833,480 B2 | 12/2017 | Junghans et al. |
| 9,834,545 B2 | 12/2017 | Chen et al. |
| 9,834,590 B2 | 12/2017 | Campana et al. |
| 9,840,548 B2 | 12/2017 | Mahr et al. |
| 9,845,362 B2 | 12/2017 | Mukherjee |
| 9,849,092 B2 | 12/2017 | Peyman |
| 9,855,297 B2 | 1/2018 | Duchateau et al. |
| 9,855,298 B2 | 1/2018 | Bot et al. |
| 9,856,322 B2 | 1/2018 | Campana et al. |
| 9,856,497 B2 | 1/2018 | Qi et al. |
| 9,856,501 B2 | 1/2018 | O'Keefe et al. |
| 9,862,756 B2 | 1/2018 | Mahr et al. |
| 9,862,775 B2 | 1/2018 | Kwon et al. |
| 9,868,774 B2 | 1/2018 | Orentas et al. |
| 9,868,951 B2 | 1/2018 | Hu et al. |
| 9,873,894 B2 | 1/2018 | Conway et al. |
| 9,879,087 B2 | 1/2018 | DeSander et al. |
| 9,885,021 B2 | 2/2018 | Bollard et al. |
| 9,889,160 B2 | 2/2018 | Jantz et al. |
| 9,889,161 B2 | 2/2018 | Jantz et al. |
| 9,890,393 B2 | 2/2018 | Duchateau et al. |
| 9,914,909 B2 | 3/2018 | Brown et al. |
| 10,117,897 B2 | 11/2018 | Sadelain et al. |
| 11,311,576 B2 | 4/2022 | Jensen et al. |
| 11,759,480 B2 | 9/2023 | Low et al. |
| 11,779,602 B2 | 10/2023 | Low et al. |
| 11,850,262 B2 | 12/2023 | Low et al. |
| 2001/0031252 A1 | 10/2001 | Low et al. |
| 2002/0004052 A1 | 1/2002 | Berd et al. |
| 2002/0018783 A1 | 2/2002 | Sadelain et al. |
| 2002/0111474 A1 | 8/2002 | Capon et al. |
| 2002/0132983 A1 | 9/2002 | Junghans |
| 2003/0077249 A1 | 4/2003 | Bebbington et al. |
| 2003/0170238 A1 | 9/2003 | Gruenberg et al. |
| 2003/0171546 A1 | 9/2003 | Jensen |
| 2003/0175288 A1 | 9/2003 | Itoh |
| 2003/0215427 A1 | 11/2003 | Jensen |
| 2004/0043401 A1 | 3/2004 | Sadelain et al. |
| 2005/0113564 A1 | 5/2005 | Campana |
| 2005/0129671 A1 | 6/2005 | Cooper et al. |
| 2006/0018878 A1 | 1/2006 | Cooper et al. |
| 2006/0067920 A1 | 3/2006 | Jensen |
| 2007/0031438 A1 | 2/2007 | Junghans |
| 2007/0036773 A1 | 2/2007 | Cooper et al. |
| 2008/0051380 A1 | 2/2008 | Auerbach et al. |
| 2008/0188000 A1 | 8/2008 | Reik et al. |
| 2009/0011984 A1 | 1/2009 | Yla-Herttuala et al. |
| 2009/0191172 A1 | 7/2009 | Cooper et al. |
| 2009/0202501 A1 | 8/2009 | Zhang et al. |
| 2009/0257994 A1 | 10/2009 | Jensen |
| 2009/0324630 A1 | 12/2009 | Jensen |
| 2010/0135974 A1 | 6/2010 | Eshhar et al. |
| 2010/0178276 A1 | 7/2010 | Sadelain et al. |
| 2010/0278830 A1 | 11/2010 | Shoemaker et al. |
| 2011/0172254 A1 | 7/2011 | Leamon |
| 2012/0093842 A1 | 4/2012 | Eshhar et al. |
| 2012/0213783 A1 | 8/2012 | Rosenberg et al. |
| 2012/0302466 A1 | 11/2012 | Sentman |
| 2013/0058936 A1 | 3/2013 | Bruenker et al. |
| 2013/0143895 A1 | 6/2013 | McAllister et al. |
| 2013/0149337 A1 | 6/2013 | Cooper et al. |
| 2013/0156794 A1 | 6/2013 | Eshhar et al. |
| 2013/0287748 A1 | 10/2013 | June et al. |
| 2013/0287752 A1 | 10/2013 | Davila |
| 2013/0309267 A1 | 11/2013 | Simmons et al. |
| 2013/0309258 A1 | 12/2013 | June et al. |
| 2013/0323834 A1 | 12/2013 | Brenner |
| 2013/0344066 A1 | 12/2013 | Faham et al. |
| 2014/0004132 A1 | 1/2014 | Brenner et al. |
| 2014/0004137 A1 | 1/2014 | Ovaa et al. |
| 2014/0017170 A1 | 1/2014 | Irvine et al. |
| 2014/0050708 A1 | 2/2014 | Powell et al. |
| 2014/0099309 A1 | 4/2014 | Powell, Jr. et al. |
| 2014/0120136 A1 | 5/2014 | Katsikis et al. |
| 2014/0134142 A1 | 5/2014 | Smith et al. |
| 2014/0134720 A1 | 5/2014 | Stauss et al. |
| 2014/0227237 A1 | 8/2014 | June et al. |
| 2014/0234348 A1 | 8/2014 | Scholler et al. |
| 2014/0255363 A1 | 9/2014 | Metelitsa et al. |
| 2014/0271582 A1 | 9/2014 | Forman et al. |
| 2014/0271635 A1 | 9/2014 | Brogdon et al. |
| 2014/0274909 A1 | 9/2014 | Orentas et al. |
| 2014/0286973 A1 | 9/2014 | Powell |
| 2014/0286987 A1 | 9/2014 | Spencer et al. |
| 2014/0294861 A1 | 10/2014 | Scholler et al. |
| 2014/0301993 A1 | 10/2014 | Powell, Jr. et al. |
| 2014/0308259 A1 | 10/2014 | Scholler et al. |

(56) References Cited

U.S. PATENT DOCUMENTS

| | | |
|---|---|---|
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0356398 A1 | 12/2014 | Riddell et al. |
| 2014/0378389 A1 | 12/2014 | Robbins et al. |
| 2015/0073154 A1 | 3/2015 | Davis |
| 2015/0110760 A1 | 4/2015 | Zhang et al. |
| 2015/0139943 A1 | 5/2015 | Campana et al. |
| 2015/0152181 A1 | 6/2015 | Sentman et al. |
| 2015/0211023 A1 | 7/2015 | Shiboleth et al. |
| 2015/0225470 A1 | 8/2015 | Zhang et al. |
| 2015/0225480 A1 | 8/2015 | Powell, Jr. |
| 2015/0238631 A1* | 8/2015 | Kim .................. A61K 47/6849 530/391.9 |
| 2015/0283178 A1 | 10/2015 | June et al. |
| 2015/0306141 A1 | 10/2015 | Jensen et al. |
| 2015/0307564 A1 | 10/2015 | Young et al. |
| 2015/0307842 A1 | 10/2015 | Sentman |
| 2015/0314014 A1 | 11/2015 | Lauermann |
| 2015/0320799 A1 | 11/2015 | Low et al. |
| 2015/0328292 A1 | 11/2015 | Spencer et al. |
| 2015/0368342 A1 | 12/2015 | Wu et al. |
| 2016/0008398 A1 | 1/2016 | Sadelain et al. |
| 2016/0046700 A1 | 2/2016 | Foster et al. |
| 2016/0046724 A1 | 2/2016 | Brogdon et al. |
| 2016/0046729 A1 | 2/2016 | Schonfeld et al. |
| 2016/0051651 A1 | 2/2016 | Brogdon et al. |
| 2016/0058857 A1 | 3/2016 | Spencer et al. |
| 2016/0068601 A1 | 3/2016 | Brogdon et al. |
| 2016/0076056 A1 | 3/2016 | Reik et al. |
| 2016/0096892 A1 | 4/2016 | Brogdon et al. |
| 2016/0120907 A1 | 5/2016 | Sentman |
| 2016/0129109 A1 | 5/2016 | Davila et al. |
| 2016/0136190 A1 | 5/2016 | Weichert et al. |
| 2016/0151465 A1 | 6/2016 | Slawin et al. |
| 2016/0166613 A1 | 6/2016 | Spencer et al. |
| 2016/0175359 A1 | 6/2016 | Spencer et al. |
| 2016/0185861 A1 | 6/2016 | Bedoya et al. |
| 2016/0222119 A1 | 8/2016 | Scholler et al. |
| 2016/0243258 A1 | 8/2016 | Scharenberg et al. |
| 2016/0250258 A1 | 9/2016 | Delaney et al. |
| 2016/0340649 A1 | 11/2016 | Brown et al. |
| 2016/0361360 A1 | 12/2016 | Chang et al. |
| 2017/0002017 A1 | 1/2017 | Andrez et al. |
| 2017/0015746 A1 | 1/2017 | Jensen |
| 2017/0029531 A1 | 2/2017 | Crane |
| 2017/0029774 A1 | 2/2017 | Jensen et al. |
| 2017/0044240 A1 | 2/2017 | Wagner et al. |
| 2017/0081411 A1 | 3/2017 | Engels et al. |
| 2017/0087185 A1 | 3/2017 | Crane et al. |
| 2017/0152297 A1 | 6/2017 | Jensen |
| 2017/0166877 A1 | 6/2017 | Bayle et al. |
| 2017/0209543 A9 | 7/2017 | Jensen |
| 2017/0224733 A1 | 8/2017 | Badie et al. |
| 2017/0267742 A1 | 9/2017 | Jensen et al. |
| 2017/0290900 A1 | 10/2017 | Low et al. |
| 2017/0306303 A1 | 10/2017 | Taunton et al. |
| 2017/0340672 A1 | 11/2017 | Wu et al. |
| 2017/0342124 A1 | 11/2017 | Scholler et al. |
| 2017/0356010 A1 | 12/2017 | Frost et al. |
| 2017/0360910 A1 | 12/2017 | Wang et al. |
| 2017/0368098 A1 | 12/2017 | Chen et al. |
| 2018/0009891 A1 | 1/2018 | Jensen |
| 2018/0016539 A1 | 1/2018 | Ding et al. |
| 2018/0022795 A1 | 1/2018 | Milone et al. |
| 2018/0022828 A1 | 1/2018 | Schonfeld et al. |
| 2018/0142198 A1 | 5/2018 | Sharei et al. |
| 2018/0142239 A1 | 5/2018 | Yu et al. |
| 2018/0214527 A1 | 8/2018 | Wang et al. |
| 2018/0282692 A1 | 10/2018 | Rawlings et al. |
| 2018/0320133 A1 | 11/2018 | Forman et al. |
| 2018/0327781 A1 | 11/2018 | Scharenberg et al. |
| 2019/0000881 A1 | 1/2019 | Sadelain et al. |
| 2019/0016776 A1 | 1/2019 | Jensen et al. |
| 2019/0161531 A1 | 5/2019 | Pule et al. |
| 2019/0209611 A1 | 7/2019 | Eckardt et al. |
| 2019/0224237 A1 | 7/2019 | Jensen et al. |
| 2019/0255109 A1 | 8/2019 | Low et al. |
| 2019/0292517 A1 | 9/2019 | Cheung et al. |
| 2019/0388468 A1 | 12/2019 | Lock et al. |
| 2020/0023009 A1 | 1/2020 | Low et al. |
| 2020/0054676 A1 | 2/2020 | Low et al. |
| 2020/0087399 A1 | 3/2020 | Jensen et al. |
| 2020/0123224 A1 | 4/2020 | Scharenberg |
| 2020/0354477 A1 | 11/2020 | Jensen et al. |
| 2020/0405760 A1 | 12/2020 | Low et al. |
| 2021/0147871 A1 | 5/2021 | Scharenberg et al. |
| 2021/0308267 A1 | 10/2021 | Low et al. |
| 2021/0317407 A1 | 10/2021 | Jensen et al. |
| 2021/0340573 A1 | 11/2021 | Scharenberg et al. |
| 2021/0346431 A1 | 11/2021 | Messmann et al. |
| 2022/0000996 A1 | 1/2022 | Low |
| 2022/0017920 A1 | 1/2022 | Scharenberg et al. |
| 2022/0257652 A1 | 8/2022 | Jensen et al. |
| 2022/0280648 A1 | 9/2022 | Low et al. |
| 2022/0409747 A1 | 12/2022 | Low et al. |
| 2023/0068879 A1 | 3/2023 | Jensen et al. |
| 2023/0172981 A1 | 6/2023 | Jensen et al. |
| 2023/0322925 A1 | 10/2023 | Jensen et al. |
| 2023/0348624 A1 | 11/2023 | Scharenberg et al. |

FOREIGN PATENT DOCUMENTS

| | | |
|---|---|---|
| CN | 106163547 A | 11/2016 |
| EP | 0340793 A2 | 11/1989 |
| EP | 2177230 A1 | 4/2010 |
| EP | 10009345 | 9/2010 |
| EP | 2537416 B1 | 11/2014 |
| EP | 2614077 B1 | 8/2016 |
| IN | 201917036615 A | 11/2019 |
| IN | 202117002059 A | 3/2021 |
| IN | 421235 | 2/2023 |
| IN | 546820 | 7/2024 |
| JP | 2015525765 A | 9/2015 |
| JP | 2016534995 A | 11/2016 |
| JP | 2017507919 A | 3/2017 |
| WO | WO 86/04356 | 7/1986 |
| WO | WO 92/10591 | 6/1992 |
| WO | WO 92/15671 | 9/1992 |
| WO | WO-9215322 A1 | 9/1992 |
| WO | WO-9530014 A1 | 11/1995 |
| WO | WO-9723613 A2 | 7/1997 |
| WO | WO-9734634 A1 | 9/1997 |
| WO | WO-9958572 A1 | 11/1999 |
| WO | WO-0014257 | 3/2000 |
| WO | WO-0023573 A2 | 4/2000 |
| WO | WO 2001/091625 | 12/2001 |
| WO | WO 02/088334 | 11/2002 |
| WO | WO-02088334 A1 | 11/2002 |
| WO | WO-2005079836 A1 | 9/2005 |
| WO | WO-2005084716 A2 | 9/2005 |
| WO | WO 2006/029879 | 3/2006 |
| WO | WO-2006036445 A2 | 4/2006 |
| WO | WO-2008031577 A1 | 3/2008 |
| WO | WO-2008045437 A2 | 4/2008 |
| WO | WO 2008/057437 | 5/2008 |
| WO | WO-2008121420 A1 | 10/2008 |
| WO | WO 2009/091826 | 7/2009 |
| WO | WO-2009117117 A1 | 9/2009 |
| WO | WO 2010/025177 | 3/2010 |
| WO | WO-2011041093 A1 | 4/2011 |
| WO | WO-2011059836 A2 | 5/2011 |
| WO | WO-2012028241 A1 | 3/2012 |
| WO | WO-2012031744 A1 | 3/2012 |
| WO | WO 2012/054825 | 4/2012 |
| WO | WO 2012/082841 | 6/2012 |
| WO | WO-2012079000 A1 | 6/2012 |
| WO | WO-2012099973 A2 | 7/2012 |
| WO | WO-2012129514 A1 | 9/2012 |
| WO | WO 2012/138475 | 10/2012 |
| WO | WO-2013019615 A2 | 2/2013 |
| WO | WO 2013/039889 | 3/2013 |
| WO | WO-2013044225 A1 | 3/2013 |
| WO | WO-2013063419 A2 | 5/2013 |

(56) References Cited

FOREIGN PATENT DOCUMENTS

| | | |
|---|---|---|
| WO | WO-2013067492 A1 | 5/2013 |
| WO | WO-2013071154 A1 | 5/2013 |
| WO | WO-2013088446 A1 | 6/2013 |
| WO | WO-2013093809 A1 | 6/2013 |
| WO | WO-2013112986 A1 | 8/2013 |
| WO | WO-2013123061 A1 | 8/2013 |
| WO | WO-2013126726 A1 | 8/2013 |
| WO | WO 2013/177247 | 11/2013 |
| WO | WO-2013166321 A1 | 11/2013 |
| WO | WO-2014011984 A1 | 1/2014 |
| WO | WO-2014011987 A1 | 1/2014 |
| WO | WO-2014031687 A1 | 2/2014 |
| WO | WO 2014/043441 | 3/2014 |
| WO | WO-2014039523 A1 | 3/2014 |
| WO | WO 2014/055771 | 4/2014 |
| WO | WO-2014055668 A1 | 4/2014 |
| WO | WO-2014068388 A1 | 5/2014 |
| WO | WO 2014/100615 | 6/2014 |
| WO | WO-2014099671 A1 | 6/2014 |
| WO | WO-2014100385 A1 | 6/2014 |
| WO | WO-2014100615 A1 * | 6/2014 ......... A61K 47/6901 |
| WO | WO-2014124143 A1 | 8/2014 |
| WO | WO-2014127261 A1 | 8/2014 |
| WO | WO-2014130635 A1 | 8/2014 |
| WO | WO-2014152177 A1 | 9/2014 |
| WO | WO-2014153002 A1 | 9/2014 |
| WO | WO 2015/057834 | 4/2015 |
| WO | WO 2015/057852 | 4/2015 |
| WO | WO-2015107075 A1 | 7/2015 |
| WO | WO-2015123496 A1 | 8/2015 |
| WO | WO-2015164594 A1 | 10/2015 |
| WO | WO-2015188135 A1 | 12/2015 |
| WO | WO 2016/025322 | 2/2016 |
| WO | WO-2016025322 A1 * | 2/2016 ........... A61K 31/404 |
| WO | WO-2016025454 A2 | 2/2016 |
| WO | WO-2016073755 A2 | 5/2016 |
| WO | WO 2016/102965 | 6/2016 |
| WO | WO-2016098078 A2 | 6/2016 |
| WO | WO 2016/054520 | 7/2016 |
| WO | WO-2016109668 A1 | 7/2016 |
| WO | WO-2016132366 A1 | 8/2016 |
| WO | WO 2016/149665 | 9/2016 |
| WO | WO-2016154621 A1 | 9/2016 |
| WO | WO-2016168766 A1 | 10/2016 |
| WO | WO-2016168769 A1 | 10/2016 |
| WO | WO-2016168773 A2 | 10/2016 |
| WO | WO 2016/201300 | 12/2016 |
| WO | WO-2016210447 A1 | 12/2016 |
| WO | WO 2017/029511 | 2/2017 |
| WO | WO 2017/029512 | 2/2017 |
| WO | WO-2017025638 A1 | 2/2017 |
| WO | WO-2017035362 A1 | 3/2017 |
| WO | WO 2017/068360 | 4/2017 |
| WO | WO 2017/068361 | 4/2017 |
| WO | WO-2017062628 A1 | 4/2017 |
| WO | WO-2017114497 A1 | 7/2017 |
| WO | WO-2017123548 A1 | 7/2017 |
| WO | WO 2017/137758 | 8/2017 |
| WO | WO 2017/137759 | 8/2017 |
| WO | WO-2017136829 A1 | 8/2017 |
| WO | WO-2017143094 A1 | 8/2017 |
| WO | WO-2017143150 A1 | 8/2017 |
| WO | WO 2017/165245 | 9/2017 |
| WO | WO-2017165571 A1 | 9/2017 |
| WO | WO 2017/177149 | 10/2017 |
| WO | WO 2017/180587 | 10/2017 |
| WO | WO-2017177149 A3 | 11/2017 |
| WO | WO 2017/216561 | 12/2017 |
| WO | WO 2017/216562 | 12/2017 |
| WO | WO-2017214167 A1 | 12/2017 |
| WO | WO-2017214170 A2 | 12/2017 |
| WO | WO-2018013797 A1 | 1/2018 |
| WO | WO-2018031694 A1 | 2/2018 |
| WO | WO-2018075794 A1 | 4/2018 |
| WO | WO-2018075807 A1 | 4/2018 |
| WO | WO-2018075813 A1 | 4/2018 |
| WO | WO-2018080541 A1 | 5/2018 |
| WO | WO-2018102761 A1 | 6/2018 |
| WO | WO-2018111763 A1 | 6/2018 |
| WO | WO-2018111834 A1 | 6/2018 |
| WO | WO-2018115146 A1 | 6/2018 |
| WO | WO-2018148224 A1 | 8/2018 |
| WO | WO-2018152451 A1 | 8/2018 |
| WO | WO 2018/160622 | 9/2018 |
| WO | WO-2018165194 A1 | 9/2018 |
| WO | WO-2018165198 A1 | 9/2018 |
| WO | WO-2018170150 A2 | 9/2018 |
| WO | WO-2018175453 A1 | 9/2018 |
| WO | WO-2018213332 A1 | 11/2018 |
| WO | WO-2019028190 A1 | 2/2019 |
| WO | WO-2019033050 A1 | 2/2019 |
| WO | WO-2019144091 A1 | 7/2019 |
| WO | WO-2019144095 A1 | 7/2019 |
| WO | WO-2019156795 A1 | 8/2019 |
| WO | WO-2019165237 A1 | 8/2019 |
| WO | WO-2019210057 A1 | 10/2019 |
| WO | WO-2020033129 A1 | 2/2020 |
| WO | WO-2020033272 A1 | 2/2020 |
| WO | WO-2021007109 A1 | 1/2021 |
| WO | WO-2021055641 A1 | 3/2021 |
| WO | WO-2021076788 A2 | 4/2021 |
| WO | WO-2021154839 A1 | 8/2021 |
| WO | WO-2021158523 A1 | 8/2021 |
| WO | WO-2021158534 A1 | 8/2021 |
| WO | WO-2021178887 A1 | 9/2021 |
| WO | WO-2022015955 A1 | 1/2022 |
| WO | WO-2022109162 A1 | 5/2022 |
| WO | WO-2022164935 A1 | 8/2022 |
| WO | WO-2023240248 A2 | 12/2023 |

OTHER PUBLICATIONS

Kennedy, M. et al., "Optical imaging of metastatic tumors using a folate-targeted fluorescent probe," J. Biomed. Opt., 2003, 8, 636-641.

Fujita, K.et al., "Prolonged disease-free period in patients with advanced epithelial ovarian cancer after adoptive transfer of tumor-infiltrating lymphocytes." Clin. Cancer Res., 1995, 1, 501-507.

Kandalaft, L. et al., "A phase I clinical trial of adoptive transfer of folate receptor-alpha redirected autologous T cells for recurrent ovarian cancer," Journal of Translational Medicine, 2012, 10:157, 10 pages.

Urbanska, K.et al., "A universal strategy for adoptive immunotherapy of cancer through use of a novel T-cell antigen receptor," Cancer Res., 2012, 72, 1844-1852.

Kochenderfer, J. et al., "Eradication of B-lineage cells and regression of lymphoma in a patient treated with autologous T cells genetically engineered to recognize CD19," Blood, 2010, 116, 4099-4102.

Rosenberg, S. A. et al., "Adoptive cell therapy for the treatment of patients with metastatic melanoma," Current Opinion in Immunology, 2009, 21, 233-240.

Ertl, H. C. et al., "Considerations for the clinical application of chimeric antigen receptor T cells: observations from a recombinant DNA advisory committee symposium held Jun. 15, 2010," Cancer Res., 2011, 71, 3175-3181.

Zhao, Y. et al., "A herceptin-based chimeric antigen receptor with modified signaling domains leads to enhanced survival of transduced T lymphocytes and antitumor activity," J. Immunol, 2009, 183, 5563- 5574.

Sadelain, M. et al., "The basic principles of chimeric antigen receptor design," Cancer Discov., 2013, 3, 388-398.

Cartellieri, M. et al., "Chimeric antigen receptor-engineered T cells for immunotherapy of cancer," J. Biomedicine and Biotechnology, 2010, Article ID 956304, 13 pages.

Urba, W.J. et al., "Redirecting T cells," New Engl. J. Med., 2011, 365, 754-757.

Porter, D.L. et al., "Chimeric antigen receptor-modified T cells in chronic lymphoid leukemia," N. Engl. J. Med., 2011, 365, 725-733.

Lamers, C. et al., "Treatment of Metastatic Renal Cell Carcinoma With Autologous T-Lymphocytes Genetically Retargeted Against Carbonic Anhydrase IX: First Clinical Experience," J. Clin. Oncol., 2006, 24, e20-22.

(56) References Cited

OTHER PUBLICATIONS

Kochenderfer, J. et al., "B-cell depletion and remissions of malignancy along with cytokine-associated toxicity in a clinical trial of anti-CD19 chimeric-antigen-receptor-transduced T cells," Blood, 2012, 119, 2709-2720.
Reichert, J. "Day 1, Emerging Disruptive Technologies and Cutting-Edge AnalyticalTechniques," MAbs, 2009, 1, 190-209.
Kularatne, S.A. et al., "Prostate-specific membrane antigen targeted imaging and therapy of prostate cancer using a PSMA inhibitor as a homing ligand," Mol. Pharm., 2009, 6,780-789.
Wayua, C. et al., "Evaluation of a Cholecystokinin 2 Receptor-Targeted Near-Infrared Dye for Fluorescence-Guided Surgery of Cancer," Molecular Pharmaceutics, 2014, 11, 468-476.
Sega, E. et al., "Tumor detection using folate receptor-targeted imaging agents," Cancer Metastasis Rev., 2008, 27, 655-664.
Alvarez-Vallina, L. et al., "Antigen-specific targeting of CD28-mediated T cell co-stimulation using chimeric single-chain antibody variable fragment-CD28 receptors," Eur. J.Immunol, 1996, 26, 2304-2309.
Imai, C. et al., "Chimeric receptors with 4-1BB signaling capacity provoke potent cytotoxicity against acute lymphoblastic leukemia," Leukemia, 2004, 18, 676-684.
Latza, U. et al., "The human OX40 homolog: cDNA structure, expression and chromosomal assignment of the ACT35 antigen," Eur. J. Immunol., 1994, 24, 677-683.
Hutloff, A. et al., "ICOS is an inducible T-cell costimulator structurally and functionally related to CD28," Nature, 1999, 397, 263-266.
Orr, B. et al., "Rapid method for measuring ScFv thermal stability by yeast surface display," Biotechnol Prog., 2003. 19, 631-638.
Kolmar, H. et al., "Alternative binding proteins: biological activity and therapeutic potential of cystine-knot miniproteins," The FEBS Journal, 2008, 275, 26684-26690.
Gross, G. et al., "Expression of immunoglobuling-T-cell receptor chimeric molecules as functional receptors with antibody-type specificity," Proc. Natl. Acad. Sci., 1989, 86, 10024-10028.
Ma, J. et al., "Versatile strategy for controlling the specificity and activity of engineered T cells," Proc. Natl. Acad. Sci., 2016, 113, E450-458.
Rodgers, D. et al., "Switch-mediated activation and retargeting of CAR-T cells for B-cell malignancies," Proc. Natl. Acad. Sci., 2016, 113, E459-468.
Sambrook et al., "Molecular Cloning: A Laboratory Manual", 3rd Edition, Cold Spring Harbor Laboratory Press, (2001).
Altschul, S. et al., "Basic local alignment search tool," J. Mol. Bio., 1990, 215, 403-410.
Bedzyk, WD et al., "Active site structure and antigen binding properties of idiotypically cross-reactive anti-fluorescein monoclonal antibodies," J Biol Chem., 1990, 265, 133-138.
Jung, S. et al., "Selection for improved protein stability by phage display," J. Mol. Biol., 1999, 294, 163-180.
Nieba, L. et al., "Disrupting the hydrophobic patches at the antibody variable/constant domain interface: improved in vivo folding and physical characterization of an engineered scFv fragment," Protein Eng., 1997, 10, 435-444.
UniProtKB—Q07011 (TNR9_HUMAN). Tumor necrosis factor receptor superfamily member 9; 14 pages; retrieved on May 13, 2016 from http://www.uniprot.org/uniprot/Q07011.
UniProtKB—P20963 (CD3Z_HUMAN). T-cell surface glycoprotein CD3 zeta chain; 12 pages; retrieved on May 13, 2016 from http://www.uniprot.org/uniprot/P20963.
UniProtKB—P01732 (CD8A_HUMAN). T-cell surface glycoprotein CD8 alpha chain; 11 pages; retrieved on May 13, 2016 from http://www.uniprot.org/uniprot/P01732.
Wikipedia. "Chimeric antigen receptor"; 9 pages; retrieved on Nov. 13, 2014 from http://en.wikipedia.org/wiki/Chimeric_antigen_receptor.
National Cancer Institute. CAR T-Cell Therapy: Engineering Patients' Immune Cells to Treat Their Cancers, Cancer Research Updates, Updated: Oct. 16, 2014; 5 pages; retrieved Nov. 17, 2014 from http://www.cancer.gov/cancertopics/research-updates/2013/CAR-T-Cells.
"Recent patent applications in chimeric antigen receptors," *Nature Biotechnology* 32(3): 239 (2014).
Kim, M. et al, "Redirection of Genetically Engineered CAR-T cells Using Bifunctional Small Molecules," J. Am. Chem. Soc., 2015, 137, 2832-2835.
Product brochure for the Engineered Autologous Cell Therapy (eACT™) Platform, available from Kite Pharma, retrieved Oct. 25, 2015 from http://www.kitepharma.com/c/products/eact.php.
Pameijer, C.R., et al., "Conversion of a tumor-binding peptide identified by phage display to a functional chimeric T cell antigen receptor," Cancer Gene Ther., 2007, 14, 91-07.
Van Dam, G. et al., "Intraoperative tumor-specific fluorescence imaging in ovarian cancer by folate receptor-a targeting: first in-human results," Nature Medicine, 2011, 17, 1315-1319.
Lu, Y. et al., "Folate-targeted dinitrophenyl hapten immunotherapy: effect of linker chemistry on antitumor activity and allergic potential," Mol. Pharm., 2007, 695-706.
Hutchins, B. et al., "Site-specific coupling and sterically controlled formation of multimeric antibody fab fragments with unnatural amino acids," J. Mol. Biol., 2011, 406, 595-603.
Tamada, et al., "Redirecting Gene-Modified T Cells toward Various Cancer Types Using Tagged Antibodies", Clin. Cancer Res., 2012, 18:6436-6445.
Abken, H. et al. "Chemeric T-Cell Receptors: Highly Specific Tools to Target Cytotoxic T-Lymphocytes to Tumour Cells," Cancer Treatment Reviews (1997); 23:97-112.
Altenschmidt, U. et al. "Adoptive transfer of in vitro-targeted, activated T lymphocytes results in total tumor regression," J. Immunol. (1997); 159:5509-15.
Altenschmidt, U., et al., "Specific cytotoxic T lymphocytes in gene therapy," J. Mol. Med. (1997); 75, 259-266.
Becker, M. L. B., et al., "Expression of a hybrid immunoglobulin-T cell receptor protein in transgenic mice," Cell (1989); 58:911-921.
Bluemel, C., et al., Epitope distance to the target cell membrane and antigen size determine the potency of T cell- mediated lysis by BiTE antibodies specific for a large melanoma suiface antigen. Cancer Immunol Immunother (2010); 59(8): 1197-209.
Bolhuis, R. L. et al. "Preparation for a phase I/II study using autologous gene modified T lymphocytes for treatment of metastatic renal cancer patients.," Adv. Exp. Med. Biol. (1998); 451:547-55.
Brentjens, et al., "Eradication of systemic B-cell tumors by genetically targeted human T lymphocytes co-stimulated by CD80 and interleukin-15," Nat. Med. (2003); 9: 279-286.
Cambier, et al., "Antigen and Fc receptor signaling. The awesome power of the immunoreceptor tyrosine-based activation motif (ITAM)," J Immunol. (Oct. 1, 1995); 155(7):3281-5.
Cameron, B.J., et al., "Identification of a Titin-Derived HLA-A1-Presented Peptide as a Cross-Reactive Target for Engineered MAGE A3-Directed T Cells," Sci Transl Med (Aug. 7, 2013); 5(197): 197ra103 (11 pages).
Chen et al. "Fusion protein linkers: property, design and functionality," Adv Drug Deliv Rev. (2013); 65: 1357-1369 (Epub Sep. 29, 2012).
Colcher, D. et al. "In vivo tumor targeting of a recombinant single-chain antigen-binding protein.," J. Nat. Cancer Inst. (1990); 82:1191-1197.
Cordaro, T. A et al. "Tumor size at the time of adoptive transfer determines whether tumor rejection occurs," Eur. J. Immunol. (2000); 30: 1297-1307.
Dall, Peter et al., "In vivo cervical cancer growth inhibition by genetically engineered cytotoxic T cells." Cancer Immunol. Immunother. (Jan. 2005); 54(1):51-60.
Darcy, P. K. et al., "Expression in cytotoxic T lymphocytes of a single-chain anti-carcinoembryonic antigen antibody. Redirected Fas ligand-mediated lysis of colon carcinoma," Eur. J. Immunol. (1998); 28:1663-72.
Dotti, et al. "Design and development of therapies using chimeric antigen receptor-expressing T cells." Immun Rev (Jan. 2014); 257(1): 107-126.

(56) References Cited

OTHER PUBLICATIONS

Dubrovska, A., et al., "A chemically induced vaccine strategy for prostate cancer," ACS Chem Biol (2011); 6(11): 1223-31.
Eshhar, Z., et al., "Functional expression of chimeric receptor genes in human T cells," J. Immunol. Meth. (2001); 248: 67-76.
Fedorov VD, et al., "PD-1- and CTLA-4-based inhibitory chimeric antigen receptors (iCARs) divert off-target immunotherapy responses," Sci Transl Med. (Dec. 11, 2013); 5(215):215ra172 (12 pages).
Ferrone, S., et al., "How much longer will tumor cells fool the immune system," Immunol. Today (2000); 21: 70-72.
Figini, M, et al., "Conversion of murine antibodies to human antibodies and their optimization for ovarian cancer therapy targeted to the folate receptor," Cancer Immunol Immunother (Apr. 2009); 58(4):531-46 (Epub Aug. 15, 2008).
Gilboa, E., "How tumors escape immune destruction and what we can do about it," Cancer Immunol. Immunother. (1999); 48: 382-385.
Gilham et al., "CAR-T cells and solid tumors: tuning T cells to challenge an inveterate foe," Trends in Molecular Medicine (2012); 18(7): 377-384 (Epub May 19, 2012).
Gilham et al., "Primary polyclonal human T lymphocytes targeted to carcino-embryonic antigens and neural cell adhesion molecule tumor antigens by CD3zeta-based chimeric immune receptors," J. Immunother, (Mar.-Apr. 2002); 25(2): 139-151.
Gillies, S.D. et al., "Targeting Human Cytotoxic T Lymphocytes to Kill Heterologous Epidermal Growth Factor Receptor-Bearing Tumor Cells," The Journal of Immunology (1991); 146(3): 1067-1071.
Gong, M. C., et al., "Prostate-specific membrane antigen (PSMA)-specific monoclonal antibodies in the treatment of prostate and other cancers," Cancer Metastasis Rev. (1999); 18: 483-490.
Gonzalez et al., "Genetic engineering of cytolytic T lymphocytes for adoptive T-cell therapy of neuroblastoma," J Gene Med (2004); 6:704-711.
Goverman, J. et al., "Chimeric immunoglobulin-T cell receptor proteins form functional receptors: implications for T cell receptor complex formation and activation," Cell (1990); 60:929-939.
Gross et al., "Development and study of chimeric immunoglobulin/T cell receptor molecules as functional receptors that endow T cells with antibody-type specificity," Ph.D. Thesis presented to the Feinberg Graduate School, The Wiezmann Institute of Science, Rehovot, Israel (1990); 1-70.
Gross, G. et al., "Endowing T cells with antibody specific using chimeric T cell receptors," Department of Chemical Immunology, Faseb J. (Dec. 1992); 6(15):3370-8.
Gross, G. et al., "Generation of effector T cells expressing chimeric T cell receptor with antibody type-specificity," Transplant. Proc. (1989); 21 (1 Pt 1):127-130.
Heuser, et al., "T-cell activation by recombinant immunoreceptors: impact of the intracellular signalling domain on the stability of receptor expression and antigen-specific activation of grafted T-cells," Gene Therapy (2003); 10: 1408-1419.
Hombach, et al., "Adoptive Immunotherapy with Genetically Engineered T Cells: Modification of the IgG1 Fc 'Spacer' Domain in the Extracellular Moiety of Chimeric Antigen Receptors Avoids 'Off-Target' Activation and Unintended Initiation of an Innate Immune Response," Gene Ther. (Oct. 2010); 17(10):1206-13.
Hwu, et al, "The Genetic Modification of T Cells for Cancer Therapy: An Overview of Laboratory and Clinical Trials," Cancer Detection and Prevention (1994); 18(1):43-50.
Irving, B. A., et al., "The cytoplasmic domain of the T cell receptor zeta chain is sufficient to couple to receptor-associated signal transduction pathways" Cell (1991); 64:891-901.
Jensen, M et al. "CD20 Is a Molecular Target for scFvFc[zeta] Receptor Redirected T Cells: Implications for Cellular Immunotherapy of CD20+ Malignancy," Biology of Blood and Marrow Transplantation (1998); 4:75-83.
Jensen, M. C., et al., Abstract #98: "Targeting Pre-B Acute Lymphoblastic Leukemia With T Cell Clones Engineered to Express a CD19-Specific Chimeric Immunoreceptor," Blood (Nov. 16, 2000); 96(11):26A.

Kim et al., "Protein conjugation with genetically encoded unnatural amino acids," Curr Opin Chem Biol (2013); 17:412-419 (Epub May 9, 2013).
Kochenderfer et al., "Construction and pre-clinical evaluation of an anti-CD19 chimeric antigen receptor," Journal of Immunotherapy (2009); 32(7): 689-702.
Krause, A., et al., "Genetic approaches to sustain the function of tumor-specific T-lymphocytes," Mol. Ther. (2000); 1 (S260): 713.
Kuwana, Y. et al., "Expression of chimeric receptor composed of immunoglobulin-derived V regions and T-cell receptor-derived C regions," Biochem. Biophys. Res. Comm. (1987); 149:960-968.
Lin et al., "Transglutaminase-catalyzed site-specific conjugation of small-molecule probes to proteins in vitro and on the surface of living cells," J. Am. Chem. Soc. (2006); 128:4542-4543.
Lustgarten, J., et al., "Specific Elimination of IgE Production Using T Cell Lines Expressing Chimeric T Cell Receptor Genes," European Journal of Immunology (1995); 25(10):2985-2991.
Ma, Q. et al., "Carcinoembryonic antigen-immunoglobulin Fc fusion protein (CEA-Fc) for identification and activation of anti-CEA immunoglobulin-T-cell receptor-modified T cells, representative of a new class of Ig fusion proteins," Cancer Gene Therapy (2004); 11: 297-306.
Ma, Q., et al., "Genetically engineered T cells as adoptive immunotherapy of cancer," Cancer Chemother Biol Response Modif (2002); 20: 315-41.
Maher, et al., "Human T-lymphocyte cytotoxicity and proliferation directed by a single chimeric TCRzeta/CD28 receptor," Nature Biotechnology (2002); 20: 70-75.
Marincola, F. M., et al., "Escape of human solid tumors from T cell recognition: molecular mechanisms and functional significance," Adv. Immunol. (2000); 74: 181-273.
McGuinness RP, et al., "Anti-tumor activity of human T cells expressing the CC49-zeta chimeric immune receptor," Hum Gene Ther. (Jan. 20, 1999); 10(2):165-73.
Melief, C. J. et al., "Strategies for immunotherapy of cancer," Adv. Immunol. (2000); 75:235-282.
Morgan RA, et al., "Cancer regression in patients after transfer of genetically engineered lymphocytes," Science (Oct. 6, 2006); 314(5796): 126-9.
Morrison, C, "CAR-T Field Booms as Next-Generation Platforms Attract Big Players," Nature Biotechnology (Jun. 2015); 33: 571-72.
Muller T, et al., "Expression of a CD20-specific chimeric antigen receptor enhances cytotoxic activity of NK cells and overcomes NK-resistance of lymphoma and leukemia cells," Cancer Immunol. Immunother. (2008); 57: 411-423.
Oelke et al., "Ex vivo induction and expansion of antigen-specific cytotoxic T cells by HLA-Ig-coated artificial antigen- presenting cells," Nature Medicine (2003); 9(5):619-624.
Paillard, F. "Immunotherapy with T cells bearing chimeric antitumor receptors," Hum. Gene Ther. (1999); 10: 151-153.
Restifo, N.P., et al., "Adoptive immunotherapy for cancer: harnessing the T cell response," Nat Rev Immunol (Mar. 22, 2012); 12(4): 269-81.
Roberts et al., "Chemistry for peptide and protein PEGylation," Advanced Drug Delivery Reviews (2002); 54:459-476.
Romeo, C. at al., "Sequence requirements for induction of cytolysis by the T cell antigen/Fc receptor zeta chain," Cell (1992); 68:889-897.
Romeo, C., et al., "Cellular immunity to HIV activated by CD4 fused to T cell or Fc receptor polypeptides," Cell (1991); 64:1037-1046.
Sadelain et al., "Targeting Tumours with Genetically Enhanced T Lymphocytes," Nat Rev Cancer (Jan. 2003); 3(1): 35-45.
Sadelain, et al., "The promise and potential pitfalls of chimeric antigen receptors," Current Opinion in Immunology (2009); 21: 215-223.
Scholler, J., et al., "Decade-long safety and function of retroviral-modified chimeric antigen receptor T cells," Sci Transl Med (May 2, 2012); 4(132): 132ra53 (7 pages).
Scott, D., et al., "Immunogenicity of biotinylated hapten-avidin complexes," Mol Immunol (1984); 21(11): 1055-60.

(56) References Cited

OTHER PUBLICATIONS

Shirasu, N. et al., "Construction and Molecular Characterization of Human Chimeric T-Cell Antigen Receptors Specific for Carcinoernbryonic Antigen," Anticancer Research (2010); 30:2731-2738.
Stancovski et al., "Targeting of T Lymphocytes to Neu/HER2-Expressing Cells Using Chimeric Single Chain Fv Receptors," J. Immunol. (1993); 151(11):6577-6582.
Stephan et al., "T cell-encoded CD80 and 4-1BBL induce auto- and transcostimulation, resulting in potent tumor rejection," Nature Medicine (Dec. 2007); 13(12): 1440-1449.
Stevens et al., "Generation of Tumor-Specific CTLs from Melanoma Patients by Using Peripheral Blood Stimulated with Allogeneic Melanoma Tumor Cell Lines," J. Immunol (1995); 154:762-771.
Themeli, M., et al., "Generation of tumor-targeted human T lymphocytes from induced pluripotent stem cells for cancer therapy," Nat Biotechnol (2013); 31(10):928-33 (Epub Aug. 11, 2013).
Turatti, F., et al., "Redirected activity of human antitumor chimeric immune receptors is governed by antigen and receptor expression levels and affinity of interaction," J Immunother (2007); 30(7): 684-93.
Uherek, C, et al., "Chimeric antigen receptors for the retargeting of cytotoxic effector cells," J. Hematother. Stem Cell Res. (2001); 10: 523-534.
Uttenthal, B.J., et al., Challenges in T cell receptor gene therapy. J Gene Med (Jun. 2012); 14(6): 386-99.
Weijtens, M. E. et al., "Single chain Ig/gamma gene-redirected human T lymphocytes produce cytokines, specifically lyse tumor cells, and recycle lytic capacity.," J. Immunol. (Jul. 15, 1996); 157(2):836-43.
Wilson, et al. "DAP12 and KAP10 (DAP10)-novel transmembrane adapter proteins of the CD3zeta family," lmmunol Res. (2000); 22(1):21-42.
Wu, et al., "Remote control of therapeutic T cells through a small molecule-gated chimeric receptor," Science (Oct. 16, 2015); 350(6258): 293 and aab4077-1 through aab4077-10 (epub Sep. 24, 2015) (12 pages).
Wu, et al., "An activating immunoreceptor complex formed by NKG2D and DAP10," Science (1999); 285:730-732.
Xu, X.J., et al., "Efficacy and safety of adoptive immunotherapy using anti-CD 19 chimeric antigen receptor transduced T-cells: a systematic review of phase I clinical trials," Leuk Lymphoma (2013); 54(2): 255-60 (Published online: Sep. 8, 2012).
Yee, C., et al., "Prospects for Adoptive T Cell Therapy," Current Opinion in Immunology (1997); 9(5):702-708.
Zhong, et al., "Integrated CD28 and 4-1BB Signals Strongly Potentiate CD8+ T Cell Mediated Eradication of Metastatic Prostate Cancer," Molecular Therapy (Jan. 1, 2006); 13: p. S103, Abstract.
Herron, J.N., et al., "High resolution structures of the 4-4-20 Fab-fluorescein complex in two solvent systems: effects of solvent on structure and antigen-binding affinity". Biophys J, 1994. 67(6): p. 2167-83.
Jung, S, et al. "Improving in vivo folding and stability of a single-chain Fv antibody fragment by loop grafting." Protein Eng. Aug. 1997; 10(8):959-66.
Vaughan, J,et al. "Human antibodies with sub-nanomolar affinities isolated from a large non-immunized phage display library". Nat Biotechnol. Mar. 1996; 14(3):309-14.
Airenne et al., "Recombinant avidin and avidin-fusion proteins", Biomolecular Engineering 16 (1999) 87-92.
Alcover et al., "A soluble form of the human CD8 alpha chain expressed in the baculovirus system: Biochemical characterization and binding to MHC Class I", Molecular Immunology, vol. 30, No. 1, pp. 55-67, 1993.
Ang et al., "Generating a Chimeric Antigen Receptor to Redirect T-Cell Specificity after Infusion", Molecular Therapy vol. 19, Supplement 1, May 2011, S137-S138.
AVD—Avidin precursor, UniProtKB—P02701 (Avid_Chick).

Baba et al., "N-Linked Carbohydrate on Human Leukocyte Antigen-C and Recognition by Natural Killer Cell Inhibitory Receptors", Human Immunology 61, 1202-1218 (2000).
Chang et al., "A Chimeric Receptor with NKG2D Specificity Enhances Natural Killer Cell Activation and Killing of Tumor Cells", Cancer Res 2013;73:1777-1786. Published online Jan. 9, 2013.
Feng et al., "Convergence on a Distinctive Assembly Mechanism by Unrelated Families of Activating Immune Receptors", Immunity, vol. 22, 427-438, Apr. 2005.
Feng et al., "The Assembly of Diverse Immune Receptors Is Focused on a Polar Membrane-Embedded Interaction Site", 2006. PLoS Biol 4(5):e142.
Hege et al., "Systemic T Cell-independent Tumor Immunity after Transplantation of Universal Receptor-modified Bone Marrow into SCID Mice", J. Exp. Med. Volume 184 Dec. 1996 pp. 2261-2269.
Katz et al., "Recognition of HLA-Cw4 but Not HLA-Cw6 by the NK Cell Receptor Killer Cell Ig-Like Receptor Two-Domain Short Tail Number 4", J Immunol 2001; 166:7260-7267.
Linenberger, "CD33-directed therapy with gemtuzumab ozogamicin in acute myeloid leukemia: progress in understanding cytotoxicity and potential mechanisms of drug resistance", Leukemia (2005) 19, 176-182.
Okazaki et al., "PD-1 immunoreceptor inhibits B cell receptormediated signaling by recruiting src homology 2-domain-containing tyrosine phosphatase 2 to phosphotyrosine", PNAS Nov. 20, 2001, vol. 98, No. 24, 13866-13871.
Wikipedia, Avidin, https://en.wikipedia.org/wiki/Avidin, downloaded Aug. 24, 2018.
Wikipedia, Antibody, https://en.wikipedia.org/w/index.php?title=Antibody&oldid=851456273, downloaded Jul. 22, 2018.
Wikipedia, CD8, https://en.wikipedia.org/w/index.php?title=CD8&oldid=840166968, downloaded May 8, 2018.
Wikipedia, CD28, https://en.wikipedia.org/w/index.php?title=CD28&oldid=831459950, downloaded Mar. 20, 2018.
Wikipedia, CD137, https://en.wikipedia.org/w/index.php?title=CD137&oldid=788581779, downloaded Jul. 2, 2017.
Wikipedia, Cholecystokinin B receptor, https://en.wikipedia.org/w/index.php?title=Cholecystokinin_B_receptor&oldid=837355377, downloaded Apr. 20, 2018.
Wikipedia, Cytokine , https://en.wikipedia.org/w/index.php?title=Cytokine&oldid=847147607, downloaded Jun. 23, 2018.
Wikipedia, Fc receptor, https://en.wikipedia.org/w/index.php?title=Fc_receptor&oldid=845940301, downloaded Jun. 15, 2018.
Wikipedia, Folate, https://en.wikipedia.org/w/index.php?title=Folate&oldid=851466622, downloaded Jun. 22, 2018.
Wikipedia, Folate receptor, https://en.wikipedia.org/w/index.php?title=Folate_receptor&oldid=834246297, downloaded Apr. 4, 2018.
Wikipedia, Folate receptor 1, https://en.wikipedia.org/w/index.php?title=Folate_receptor_1&oldid=845790606, downloaded Jun. 14, 2018.
Wikipedia, Folate receptor gamma, https://en.wikipedia.org/w/index.php?title=Folate_receptor_gamma&oldid=621589158, downloaded Aug. 17, 2014.
Wikipedia, FOLR2, https://en.wikipedia.org/w/index.php?title=FOLR2&oldid=798129670, downloaded Aug. 31, 2017.
Wikipedia, Glutamate carboxypeptidase II, https://en.wikipedia.org/w/index.php?title=Glutamate_carboxypeptidase_II&oldid=845231234, downloaded Jun. 10, 2018.
Wikipedia, IL-2 receptor, https://en.wikipedia.org/w/index.php?title=IL-2_receptor&oldid=847173411, downloaded Jun. 23, 2018.
Wikipedia, Interferon, https://en.wikipedia.org/w/index.php?title=Interferon&oldid=848844304, downloaded Jul. 4, 2018.
Wikipedia, Interleukin 2, https://en.wikipedia.org/w/index.php?title=Interleukin_2&oldid=838351127, downloaded Apr. 26, 2018.
Wikipedia, Interleukin 10, https://en.wikipedia.org/w/index.php?title=Interleukin_10&oldid=835415026, downloaded Apr. 8, 2018.
Wikipedia, Interleukin-1 family, https://en.wikipedia.org/w/index.php?title=Interleukin-1_family&oldid=847253010, downloaded Jun. 24, 2018.
Wikipedia, Single-chain variable fragment, https://en.wikipedia.org/w/index.php?title=Single-chain_variable_fragment&oldid=841449115, downloaded May 15, 2018.

(56) References Cited

OTHER PUBLICATIONS

Wikipedia, TNF receptor superfamily, https://en.wikipedia.org/w/index.php?title=TNF_receptor_superfamily&oldid=850804991, downloaded Jul. 18, 2018.

Wikipedia, Transforming growth factor beta superfamily, https://en.wikipedia.org/w/index.php?title=Transforming_growth_factor_beta_superfamily&oldid=850390369, downloaded Jul. 15, 2018.

Arch, R, et al., "4-1BB and Ox40 Are Members of a Tumor Necrosis Factor (TNF)-Nerve Growth Factor Receptor Subfamily That Bind TNF Receptor-Associated Factors and Activate Nuclear Factor kB," Molecular and Cellular Biology (1998); 558-565.

Aruffo, A, et al., "Molecular cloning of a CD28 cDNA by a high-efficiency COS cell expression system," Proc. Nati. Acad. Sci. USA (1987); 84: 8573-8577.

Bauer, A, et al., "Differential signal transduction via T-cell receptor CD3'2, CD3C-,v, and CD3'q2 isoforms," Proc. Nati. Acad. Sci. USA (1991); 88: 3842-3846.

Bejcek, B, et al., "Development and Characterization of Three Recombinant Single Chain Antibody Fragments (scFvs) Directed against the CD19 Antigen1," Cancer Research 55, (1995); 2346-2351.

Boomer, J, et al.,. "An Enigmatic Tail of CD28 Signaling," Washington University School of Medicine (2010); 1-20.

UniProtKB—P10966 (CD8B_HUMAN).

UniProtKB—P10747 (CD28_HUMAN).

Chalupny, J, et al,."T-cell activation molecule 4-1BB binds to extracellular matrix proteins," Proc. Nat!. Acad. Sci. USA (1992); 89: 10360-10364.

Jang, I, et al., "Human 4-1BB (CD137) Signals Are Mediated by TRAF2 and Activate Nuclear Factor-kB," Biochemical and Biophysical Research Communications (1998); 613-620.

Kwon, B, et al., "cDNA sequences of two inducible T-cell genes," cDNA sequences of two inducible T-cell genes (1989); 86: 1963-1967.

Kwon, B, et al., "Expression Characteristics of Two Potential T Cell Mediator Genes," Cellular Immunology (1989); 414-422.

Lee, D, et al., "4-1BB Signaling Activates the T Cell Factor 1 Effector/b-Catenin Pathway with Delayed Kinetics via ERK Signaling and Delayed PI3K/AKT Activation to Promote the Proliferation of CD8+ T Cells," PLOS One (2013); 8: 1-11.

Melero, I, et al., "Amplification of tumor immunity by gene transfer of the co-stimulatory 4-1BB ligand: synergy with the CD28 co-stimulatory pathway," Bristol-Myers Squibb Pharmaceutical Research Institute (1998); 1116-1121.

Nam, K, et al., "Cross-Linking of 4-1BB Activates TCR-Signaling Pathways in CD8 . T Lymphocytes1," The Journal of Immunology; 1898-1905.

Paillasse, M, et al., "Insights into the Cholecystokinin 2 Receptor Binding Site and Processes of Activation," The American Society for Pharmacology and Experimental Therapeutics (2006); 70:1935-1945.

Saoulli, C, et al., "CD28-independent, TRAF2-dependent Costimnlation of Resting T Cells by 4-1BB Ligand," Department of Immunology University of Toronto (1998); 1-67.

Stein, P, et al., "The Cytoplasmic Domain of CD28 Is both Necessary and Sufficient for Costimulation of Interleukin-2 Secretion and Association with Phosphatidylinositol 3'-Kinase," American Society for Microbiology (1994); 14: 3392-3402.

"TNF Superfamily Pathway," ThermoFinder Scientific.

"Tumor necrosis factor receptor superfamily," HUGO Gene Nomenclature Committee.

Wen, T, et al., "4-1BB Ligand-Mediated Costimulation of Human T Cells Induces CD4 and CD8 T Cell Expansion, Cytokine Production, and the Development of Cytolytic Effector Function1," 4897-4906.

Ye, H, et al., "The Structural Basis for the Recognition of Diverse Receptor Sequences by TRAF2," The Weill Medical College and Graduate School of Medical Sciences of Cornell University; v: 321-330.

Tam et al., "Functional, Biophysical, and Structural Characterization of Human IgG1 and IgG4 Fc Variants with Ablated Immune Functionality," Antibodies 2017, 6, 12.

Reddy et al., "Elimination of Fc Receptor-Dependent Effector Functions of a Modified IgG4 Monoclonal Antibody to Human CD4," J Immunol 2000; 164: 1925-1933.

Alexander et al., "Indoleamine 2,3-Dioxygenase Expression in Transplanted NOD Islets Prolongs Graft Survival After Adoptive Transfer of Diabetogenic Splenocytes," Diabetes 2002, vol. 51 pp. 356-365.

Wikipedia, Amino acid, https://en.wikipedia.org/wiki/Amino_acid, downloaded Jul. 30, 2018.

Bauer et al., "Activation of NK Cells and T Cells by NKG2D, a Receptor for Stress-Inducible MICA," Science 1999, vol. 285 pp. 727-729.

Boursier et al., "Evidence for an Extended Structure of the T-cell Co-receptor CD8α as Deduced from the Hydrodynamic Properties of Soluble Forms of the Extracellular Region*," The Journal of Biological Chemistry 1993, vol. 268, No. 3, Issue of Jan. 25, pp. 2013-2020.

Brennan et al., "Carbohydrate Recognition by a Natural Killer Cell Receptor, Ly-49C*," The Journal of Biological Chemistry 1995, vol. 270, No. 17, Issue of Apr. 28, pp. 9691-9694.

Bruhns et al., "Differential Roles of N- and C-Terminal Immunoreceptor Tyrosine-Based Inhibition Motifs During Inhibition of Cell Activation by Killer Cell Inhibitory Receptors," The Journal of Immunology 1999; 162:3168-3175.

Canfield et al., "The Binding Affinity of Human IgG for its High Affinity Fc Receptor Is Determined by Multiple Amino Acids in the CH2 Domain and Is Modulated by the Hinge Region," J. Exp. Med. 1991, vol. 173 pp. 1483-1491.

Wikipedia, CD3 (immunology), https://en.wikipedia.org/wiki/CD3_(immunology), downloaded Jul. 24, 2018.

Receptors, NK Cell Lectin-Like MeSH Descriptor Data 2018, NIH U.S. National Library of Medicine, Jul. 25, 2018.

Cooper et al., "Enhanced antilymphoma efficacy of CD19-redirected influenza MP1-specific CTLs by cotransfer of T cells modified to present influenza MP1," Blood 2005, vol. 105 No. 4 pp. 1622-1631.

Wikipedia, C-type lectin, https://en.wikipedia.org/wiki/C-type_lectin, downloaded Jul. 25, 2018.

Diefenbach et al., "The innate immune response to tumors and its role in the induction of T-cell immunity," Immunological Reviews 2002, vol. 188: 9-21.

Duncan et al., Localization of the binding site for the human high-affinity Fc receptor on IgG, Nature 1998, vol. 332 pp. 563-564.

Frost et al., "In Vitro Evaluation of Avidin Antibody Pretargeting Using $^{211}$At-Labeled and Biotinylated Poly-L-Lysine as Effector Molecule*," Cancer 2010, Cancer Therapy With Antibodies and Immunoconjugates, Supplement to Cancer, pp. 1101-1110.

Hatakeyama et al., "Transmembrane Signaling of Interleukin 2 Receptor," J. Exp. Med. 1987, vol. 166 pp. 362-375.

Hege et al., "Safety, tumor trafficking and immunogenicity of chimeric antigen receptor (CAR)-T cells specific for TAG-72 in colorectal cancer," Journal for Immuno Therapy of Cancer 2017, 5:22.

Hombach et al., "T cell activation by recombinant FcERI γ-chain immune receptors: an extracellular spacer domain impairs antigen-dependent T cell activation but not antigen recognition," Gene Therapy (2000) 7, 1067-1075.

Jena et al., "Redirecting T-cell specificity by introducing a tumor-specific chimeric antigen Receptor," Blood 2010, vol. 116, No. 7, pp. 1035-1044.

Jonnalagadda et al., "Chimeric Antigen Receptors With Mutated IgG4 Fc Spacer Avoid Fc Receptor Binding and Improve T Cell Persistence and Antitumor Efficacy," Molecular Therapy 2015, vol. 23, No. 4, pp. 757-768.

Wikipedia, Killer-cell immunoglobulin-like receptor, https://en.wikipedia.org/wiki/Killer-cell_immunoglobulin-like_receptor, downloaded Jul. 25, 2018.

Wikipedia, KLRA1, https://en.wikipedia.org/wiki/KLRA1, downloaded Jul. 25, 2018.

(56) References Cited

OTHER PUBLICATIONS

Wikipedia, NKG2D, https://en.wikipedia.org/wiki/NKG2D, downloaded Jul. 25, 2018.
Wikipedia, Paratope, https://en.wikipedia.org/wiki/Paratope, downloaded Jul. 25, 2018.
PeproTech, Recombinant Human 4-1BB Receptor, https://www.peprotech.com/recombinant-human-4-1bb-receptor, downloaded Jul. 25, 2018.
Pochitaloff et al., "Human CD28 and CTLA-4 Ig superfamily genes are located on chromosome 2 at bands q33-q34," Abstract. Immunogenetics 1990; 31(3): 198-201.
Pollock et al., Inducible T cell antigen 4-1BB. Analysis of expression and function, J Immunol 1993; 150:771-781.
Protein Lounge, 4-1BB Pathway, http://www.proteinlounge.com/Pathway/4-1BB%20Pathway, downloaded Jul. 25, 2018.
Qin et al., "Incorporation of a hinge domain improves the expansion of chimeric antigen receptor T cells," Journal of Hematology & Oncology (2017) 10:68.
Rai et al., "Expression systems for production of heterologous proteins," Current Science 2001, vol. 80, No. 9, pp. 1121-1128.
Reubi, Jean Claude, "Peptide Receptors as Molecular Targets for Cancer Diagnosis and Therapy," Endocrine Reviews 24(4): 389-427.
Saraswat et al., "DNA as Therapeutics; an Update," Indian J Pharm Sci. Sep.-Oct. 2009; 71(5): 488-498.
Shields et al., "High Resolution Mapping of the Binding Site on Human IgG1 for FcγRI, FcγRII, FcγRIII, and FcRn and Design of IgG1 Variants with Improved Binding to the FcγR*," The Journal of Biological Chemistry 2001, vol. 276, No. 9, Issue of Mar. 2, pp. 6591-6604.
Wikipedia, Single-domain antibody, https://en.wikipedia.org/wiki/Single-domain_antibody, downloaded Jul. 27, 2018.
Wikipedia, Small molecule, https://en.wikipedia.org/wiki/Small_molecule, downloaded Jul. 27, 2018.
Sobota et al., "Binding of IgG-Opsonized Particles to FcγR Is an Active Stage of Phagocytosis That Involves Receptor Clustering and Phosphorylation," The Journal of Immunology 2005; 175:4450-4457.
The LTR Retroviral Promoter; Long Terminal Repeats: The Retroviral Promoter. https://web.stanford.edu/group/nolan/_OldWebsite/tutorials/retcl_3_ltrs.html retrieved Jul. 26, 2018.
An et al., "IgG2m4, an engineered antibody isotype with reduced Fc function," mAbs 2009, Landes Bioscience, 1:6, 572-579.
Foell et al., "CD137-mediated T cell co-stimulation terminates existing autoimmune disease in SLE-prone NZB/NZW F1 mice.," Ann N Y Acad Sci. Apr. 2003; 987:230-5.
Wikipedia, Glycosylation, https://en.wikipedia.org/wiki/Glycosylation, downloaded Jul. 31, 2018.
Kim et al., "Therapeutic Potential of 4-1BB (CD137) as a Regulator for Effector CD8+ T Cells," Journal of Hematotherapy & Stem Cell Research (2001) 10:441-449.
Wang et al., "Current status and perspectives of chimeric antigen receptor modified T cells for cancer treatment," Protein Cell 2017, 8(12):896-925.
Wilkie et al., "Retargeting of Human T Cells to Tumor-Associated MUC1: The Evolution of a Chimeric Antigen Receptor," The Journal of Immunology Apr. 2008, pp. 4901-4909.
Grosenbach et al., "A recombinant vector expressing transgenes for four T-cell costimulatory molecules (OX40L, B7-1, ICAM-1, LFA-3) induces sustained CD4+ and CD8+ T-cell activation, protection from apoptosis, and enhanced cytokine production," Cellular Immunology 222 (2003) 45-57.
Moore et al., "Characterisation of salmon and trout CD8α and CD8β," Molecular Immunology 42 (2005) 1225-1234.
Hunter et al., "Inhibition of Fcγ Receptor-Mediated Phagocytosis by a Nonphagocytic Fcγ Receptor," Blood, vol. 91, No. 5 Mar. 1, 1998: pp 1762-1768.
Swanson et al., "The coordination of signaling during Fc receptor-mediated phagocytosis," Journal of Leukocyte Biology, vol. 76, Dec. 2004, pp. 1093-1103.

Munn et al., "Role of Low-Affinity Fc Receptors in Antibody-dependent Tumor Cell Phagocytosis by Human Monocyte-derived Macrophages," Cancer Research 51, 1117-1123, Feb. 15, 1991.
Cole et al., "The molecular determinants of CD8 co-receptor function", 2012, Immunology, 137, 139-148.
Harper et al., "CTLA-4 and CD28 Activated Lymphocyte Molecules are Closely Related in Both Mouse and Human as to Sequence, Message, Expression, Gene Structure, and Chromosomal Location", The Journal of Immunology, vol. 147, 1037-1044, No. 3, Aug. 1, 1991.
Isakov et al., "PKC-theta-mediated signal delivery from the TCR/CD28 surface receptors", Frontiers in Immunology, T Cell Biology, Aug. 2012, vol. 3, Article 273, pp. 1-12.
Love et al., "ITAM-mediated Signaling by the T-Cell Antigen Receptor", Cold Spring Harb Perspect Biol 2010; 2:a002485.
Medstrand et al., "Long Terminal Repeats Are Used as Alternative Promoters for the Endothelin B Receptor and Apolipoprotein C-I Genes in Humans", The Journal of Biological Chemistry, vol. 276, No. 3, Issue of Jan. 19, pp. 1896-1903, 2001.
Prasad et al., "T-cell antigen CD28 interacts with the lipid kinase phosphatidylinositol 3-kinase by a cytoplasmic Tyr(P)-Met-Xaa-Met motif". Proc. Natl. Acad. Sci. USA, vol. 91, pp. 2834-2838, Mar. 1994.
Definition of "Protein", Concise Dictionary of Biomedicine and Molecular Biology, $2^{nd}$ Edition, Pei-Show Juo, PhD, 2002, p. 903.
Wikipedia, Protein, https://en.wikipedia.org/w/index.php?title=Protein&oldid=861574349, downloaded Oct. 15, 2018.
Riha et al., "CD28 co-signaling in the adaptive immune response" Self/Nonself 1:3, 231-240; Jul./Aug./Sep. 2010.
Riley et al., "The CD28 family: a T-cell rheostat for therapeutic control of T-cell activation", Blood, Jan. 1, 2005, vol. 105, No. 1, pp. 13-21.
Cooper et al., Sequence Listing, Compositions and Methods Related to a Human CD19-Specific Chimeric Antigen Receptor (H-CAR), U.S. Appl. No. 61/020,991, filed Jan. 14, 2008, 5 pages.
Maeda et al., "Tumor vascular permeability and the EPR effect in macromolecular therapeutics: a review," Journal of Controlled Release 65 (2000), pp. 271-284 (14 pages).
"Common Terminology Criteria for Adverse Events (CTCAE)" National Cancer Institute Common Toxicity Criteria version 4.03 (NCI-CTCAE v4.03 (2010) (196 pages).
Abstracts for the 26th Annual Scientific Meeting of the Society for Immunotherapy of Cancer (SITC), J Immunother., vol. 34, No. 9, Nov.-Dec. 2011 (62 pages).
Alonso-Camino et al. "CARbodies: Human Antibodies Against Cell Surface Tumor Antigens Selected From Repertoires Displayed on T Cell Chimeric Antigen Receptors." (2013) Mol Ther Nucl Acids 2, e93 (11 pages).
Altvater, B., et al., "284 (CD244) Signaling by Recombinant Antigen-specific Chimeric Receptors Costimulates Natural Killer Cell Activation to Leukemia and Neuroblastoma Cells", Clin Cancer Res 2009;15(15) Aug. 1, 2009: 4857-66.
Baniyash et al., "The T Cell Antigen Receptor Zeta Chain Is Tyrosine Phosphorylated open Activation" The Journal of Biological Chemistry, vol. 263, No. 34, Issue of Dec. 5, pp. 18225-18230.
Barrett et al., Chimeric Antigen Receptor Therapy for Cancer Annual Review of Medicine vol. 65: 333-347 (2014).
Baum et al. "Retrovirus vectors: toward the plentivirus?" (2006) Molecular Therapy: The Journal of the American Society of Gene Therapy. 13:1050-1063.
Berg et al., "Section 3.2 Primary Structure: Amino Acids Are Linked by Peptide Bonds to Form Polypeptide Chains" Biochemistry, 5th Ed. New York. W.H. Freeman; 2002, pp. 1-16.
Berger, C., et al., Analysis of trans gene-specific immune responses that limit the in vivo persistence of adoptively transferred HSV-TK-modified donor T cells after allogeneic hematopoietic cell transplantation. Blood, 2006. 107(6): p. 2294-302.
Boomer et al., "Cutting Edge: A Double-Mutant Knockin of the CD28 YMNM and PYAP Motifs Reveals a Critical Role for the YMNM Motif in Regulation of T Cell Proliferation and Bcl-x L Expression" The Journal of Immunology. 2014; 192, pp. 3465-3469.

(56) References Cited

OTHER PUBLICATIONS

Brentjens et al., "CD19-targeted T cells rapidly induce molecular remissions in adults with chemotherapy-refractory acute lymphoblastic leukemia." Sci Transl Med. 2013 5(177) ra38 (11 pages).
Bukczynski et al., "Costimulatory ligand 4-1 BBL (CD137L) as an efficient adjuvant of human antiviral cytotoxic T cell responses," Proc. Natl. Acad. Sci. USA, 2004, 101: 1291-1296.
Cannons et al., "4-1BB ligand induces cell division, sustains survival, and enhances effector function of CD4 and CD8 T cells with similar efficacy," J Immunol. Aug 2001, 167(3): 1313-1324.
Carlens et al. "Ex vivo T lymphocyte expansion for retroviral transduction: influence of serum-free media on variations in cell expansion rates and lymphocyte subset distribution." (2000) Exp Hematol 28(10): 1137-46.
Cavalieri et al. "Human T lymphocytes transduced by lentiviral vectors in the absence of TCR activation maintain an intact immune competence." (2003) Blood. 102(2): 497-505.
Chalupny et al., "T-cell activation molecule 4-1BB binds to extracellular matrix proteins," Proc. Natl. Acad. Sci., USA. 89: 103360-10364 (Nov. 1992).
Cheadle et al, "Chimeric antigen receptors for T-cell based therapy" Methods Mol Biol. 2012; 907:645-66.
Cho C. "Rapid identification of cytokine release syndrome after haploidentical PBSC transplantation and successful therapy with tocilizumab." Bone Marrow Transplant. Dec. 2016:51(12):1620-1621, Epub Sep. 26, 2016.
Cho et al., "Macromolecular versus small-molecule therapeutics: drug discovery, development and clinical considerations" TIBTECH, vol. 14, May 1996, pp. 153-158.
Cohen et al. "Recognition of fresh human tumor by human peripheral blood lymphocytes transduced with a bicistronic retroviral vector encoding a murine anti-p53 TCR" (2005) J Immunol. 175:5799-5808.
Cooper et al. "T-cell clones can be rendered specific for CD19: toward the selective augmentation of the graft-versus-B-lineage leukemia effec" (2003) Blood. 101(4): 1637-1644.
Cooper et al., Sequence Listing, Compositions and Methods Related to a Human CD19-Specific Chimeric Antigen Receptor (H-CAR), U.S. Appl. No. 61/020,991, filed Jan. 14, 2008, 5 pages.
Croft, M., "The role of TNF superfamily members in T-cell function and diseases" Nature Reviews, Immunology, vol. 9, Apr. 2009, pp. 271-285.
Davila M. L. ET AL: "Efficacy and toxicity management of 19-28z CAR T cell therapy in B cell acute lymphoblastic leukemia" Sci Transl Med. Feb. 19, 2014;6(224):224-25.
Davila Marco L. et al: "CD19 Targeted T Cells for Hematologie Malignancies—Clinical Experience to Date", Cancer Journal, vol. 21, no. 6, Jan. 1, 2015 (Jan. 1, 2015), pp. 470-474.
Debelouchina et al., "A molecular engineering toolbox for the structural biologist" Quarterly Reviews of Biophysics, 2017, 50, e7, pp. 1-41.
Frecha et al. "Advances in the field of lentivector-based transduction of T and B lymphocytes for gene therapy" (2010) Molecular Therapy: The Journal of the American Society of Gene Therapy, 18:1748-1757.
Gargett, T., et al., GD2-specific CART Cells Undergo Potent Activation and Deletion Following Antigen Encounter but can be Protected From Activation-induced Cell Death by PD-1 Blockade. Mol Ther, 2016. 24(6): p. 1135-49.
Greenfield, E. A, Nguyen, K. A & Kuchroo, V.K. CD28/B7 co-stimulation: a review. Crit. Rev. Immunol. 18, 389-41 8 (1998).
Griffiths et al., "The Nature of DNA" Modern Genetic Analysis. New York: W.H. Freeman: 1999, pp. 1-11.
Grupp Stephan A.: Advances in T-cell therapy for All, Best Practice & Research Clinical Haematology, vol. 27, No. 3-4, Sep. 1, 2014 (Sep. 1, 2014), pp. 222-228.
Gruss et al., "Tumor Necrosis Factor Ligand Superfamily: Involvement in the Pathology of Malignant Lymphomas" Blood, vol. 85, No. 12, Jun. 15, 1995, pp. 3378-3404.
Guinn et al., "4-1BBL Cooperates with B7-1 and B7-2 in Converting a B Cell Lymphoma Cell Line into a Long- Lasting Antitumor Vaccine," The Journal of Immunology 162:5003-5010 (1999).
Habib-Agahi,H., Phan,T.T. and Searle,P.F. Co-stimulation with 4-1BB ligand allows extended T-cell proliferation, synergizes with CD80/CD86 and can reactivate anergic T cells Int. Immunol. 19 (12), 1383-1394 (2007).
Hackett et al. "A transposon and transposase system for human application" (2010) Molecular Therapy: The Journal of the American Society of Gene Therapy. 18:674-683.
Hanson, H. L. et al. Eradication of established tumors by CD8+ T cell adoptive immunotherapy. Immunity 13, 265-276 (2000).
Haynes, Nicole M., Marie B. Snook, Joseph A. Trapani, Loretta Cerruti, Stephen M. Jane, Mark J. Smyth and Philip K. Darcy "Redirecting Mouse CTL Against Colon Carcinoma: Superior Signaling Efficacy of Single-Chain Variable Domain Chimeras Containing TCR-zeta vs FeepsilonRI-gamma" J Immunol 2001; 166:182-187 (Haynes 2001).
Huang, J., et al., Modulation by IL-2 of CD70 and CD27 expression on CD8+ T cells: importance for the therapeutic effectiveness of cell transfer immunotherapy J. Immunol. 176 (12), 7726-7735 (2006).
Hughes M. S. et al., Transfer of a TCR gene derived from a patient with a marked antitumor response conveys highly active T-cell effector functions. Hum Gene Ther Apr. 2005; 16(4):457-72).
Imai, K., et al., "Comparing Antibody and Small-Molecule Therapies for Cancer"; https://www.medscape.com/viewarticle/550008 (26 pages).
Janeway et al., "Appendix I. Immunologists' Toolbox" Immunobiology: The Immune System in Health and Disease. 5th ed. New York: Garland Science; 2001 (101 pages).
Janeway et al., "The structure of a typical antibody molecule" Immunobiology: The Immune System in Health and Disease. 5th Ed. New York: Garland Science; 2001, pp. 1-11.
Jensen, M.C., et al., Antitransgene rejection responses contribute to attenuated persistence of adoptively transferred CD20/CD19-specific chimeric antigen receptor redirected T cells in humans. Biol Blood Marrow Transplant, 2010. 16(9): p. 1245-56.
Kagoya, Y., et al., Transient stimulation expands superior antitumor T cells for adoptive therapy. JCI Insight, 2017. 2(2): p. e89580 (13 pages).
Kang, S. et al: "Therapeutic uses of anti-interleukin-6 receptor antibody", International Immunology, vol . 27, No. 1, Aug. 20, 2014 (Aug. 20, 2014), pp. 21-29.
Kariv et al., Analysis of the Site of Interaction of CD28 with Its Counterreceptors CD80 and CD86 and Correlation with Function, 157 J. Immunol. 29-38 (1996).
Kintzing et al., "Emerging Strategies for Developing Next-Generation Protein Therapeutics for Cancer Treatment" Trends in Pharmacological Sciences, vol. 37, No. 12, Dec. 2016, pp. 993-1008.
Klotz et al., "Macromolecule-Small Molecule Interactions. Strong Binding by Intramolecularly Cross-Linked Polylysine" Biochemistry. vol. 10, No. 6, Mar. 16, 1971, pp. 923-926.
Kochenderfer et al., "Treating B-cell cancer with T cells expressing anti-CD19 chimeric antigen receptors" 2013, Nature Reviews Clinical Oncology, 10, 267-276 (2013).
Lafage-Pochitaloff M, Costello R, Conez D, Simonetti J, Mannoni P, Mawas C, Olive D. "Human CD28 and CTLA-4 Ig superfamily genes are located on chromosome 2 at bands q33-q34" Immunogenetics 1190;31(3):198-201.
Lee D. W. et al: "Current concepts in the diagnosis and management of cytokine release syndrome" Blood. Jul. 10, 2014;124(2):188-95. doi: 10.1182/blood-2014-05-552729. Epub May 29, 2014.
Lee, Blood 2015 126:1048. Erratum to Lee D. W. et al: "Current concepts in the diagnosis and management of cytokine release syndrome" Blood. Jul. 10, 2014;124(2):188-95. doi: 10.1182/blood-2014-05-552729. Epub May 29, 2014.
Lee, Blood 2016 128:1533 Erratum to Lee D. W. et al: "Current concepts in the diagnosis and management of cytokine release syndrome" Blood. Jul. 10, 2014;124(2):188-95. doi: 10.1182/blood-2014-05-552729. Epub May 29, 2014.
Liebowitz, D. N., Lee, K. P. & June, C. H. Co-stimulatory approaches to adoptive immunotherapy. Curr. Opin. Oncol. 10, 533-541 (1998).

(56) References Cited

OTHER PUBLICATIONS

Lodish et al., "Heirarchical Structure of Proteins" Molecular Cell Biology. 4th Ed. New York: W.H. Freeman; 2000. pp. 1-25
Long, A.H., et al., 4-1BB costimulation ameliorates T cell exhaustion induced by tonic signaling of chimeric antigen receptors. Nat Med, 2015. 21(6): p. 581-90.
Lueders et al., "The Long Terminal Repeat of an Endogenous Intracisternal A—Particle Gene Functions as a Promoter When Introduced into Eucaryotic Cells by Transfection" Molecular and Cellular Biology, vol. 4, No. 10, Oct. 1984, pp. 2128-2135.
Maude Shannon L. et al. "Chimeric Antigen Receptor T Cells for Sustained Remissions in Leukemia" N Engl J Med. Oct. 16, 2014;371(16):1507-17.
Maude Shannon L. et al. "Managing Cytokine Release Syndrome Associated With Novel T Cell-Engaging Therapies" Cancer J. Mar.-Apr. 2014;20(2):119-22.
Maus et al., "Ex vivo expansion of polyclonal and antigen-specific cytotoxic T lymphocytes by artificial APCs expressing ligands for the T-cell receptor, CD28 and 4-1BB," Nature Biotechnology, Nature Publishing Group, New York, NY, US, vol. 20, No. 2, Feb. 1, 2002, pp. 143-148.
Maus, M.V., et al., T cells expressing chimeric antigen receptors can cause anaphylaxis in humans. Cancer Immunol Res. 2013. 1(1): p. 26-31.
Mooney et al., "Concise Review: Neural Stem Cell-Mediated Targeted Cancer Therapies" Stem Cells Translational Medicine, 2018, pp. 740-747.
Mungra et al., "Targeted human cytolytic fusion proteins at the cutting edge: harnessing the apoptosis-inducing properties of human enzymes for the selective elimination of tumor cells" Oncotarget, vol. 10, No. 8, 2019, pp. 897-915.
Oelsner, S., et al., "Continuously expanding CAR NK-92 cells display selective cytotoxicity against B-cell leukemia and lymphoma", Cytotherapy, 2017; 19: 235-249.
Pages et al., "Two Distinct Intracytoplasmic Regions of the T-cell Adhesion Molecule CD28 Participate in Phosphatidylinositol 3-Kinase Association"The Journal of Biological Chemistry, vol. 271, No. 16, Apr. 19, 1996, pp. 9403-9409.
Park et al., "Treating cancer with genetically engineered T cells" Trends Biotechnol. Nov. 29, 2011(11): 550-557.
Parkhurst et al. "Characterization of genetically modified T-cell receptors that recognize the CEA:691-699 peptide in the context of HLA-A2.1 on human colorectal cancer cells" (2009) Clin Cancer Res. Jan. 1, 2009;15(1):169-80.
Patel Jaina M et al: "Cancer CARtography: charting out a new approach to cancer immunotherapy", Immunotherapy. 2014:6(6):675-8.
Porter DL, et al. "Chimeric antigen receptor T cells persist and induce sustained remissions in relapsed refractory chronic lymphocytic leukemia". Science translational medicine. 2015;7(303):303-39. doi: 10. 1 126/scitranslmed.aac5415. PubMed PMID: 26333935.
Redmond et al., "The role of OX40-mediated co-stimulation in T cell activation and survival," Crit. Rev. Immunol. 2009, 29(3): 187-201.
Riviere, I., Gallardo, H. F., Hagani, A B. & Sadelain, M. Retroviral-mediated gene transfer in primary murine and human T-lymphocytes. Mol. Biotechnol. 15, 133-142 (2000).
Rosenberg "Cell transfer immunotherapy for metastatic solid cancer—what clinicians need to know" (2011) Nat Rev Clin Oncol. 8(10):577-85).
Rosenberg SA, Restifo N P, Yang J C, Morgan RA, Dudley M E. Adoptive cell transfer: a clinical path to effective cancer immunotherapy. Nat Rev Cancer. Apr. 2008; 8(4):299-308.
Rotz Seth J. et al. "Severe cytokine release syndrome in a patient receiving PD-1-directed therapy" Pediatr Blood Cancer. Dec. 2017;64(12), Epub May 24, 2017 (4 pages).
Rueckert S, et al., "A monoclonal antibody as an effective therapeutic agent in breast cancer: trastuzumab" Expert Opin Biol Ther. Jun. 2005:5(6):853-66.

Schonfeld, K, et al., "Selective Inhibition of Tumor Growth by Clonal NK Cells Expressing an Erb82/HER2-Specific Chimeric Antigen Receptor", Mol. Ther., vol. 23 No. 2, 330-338 Feb. 2015.
Schreiber, S.L., "Organic synthesis toward small-molecule probes and drugs" PNAS, vol. 108, No. 17, Apr. 26, 2011, pp. 6699-6702.
Sentman "Challenges of creating effective chineric antigen receptors for cancer therapy" Immunotherapy. Aug. 2013;5(8):783-5.
Serghides et al., "Evaluation of OX40 Ligand as a Costimulator of Human Antiviral Memory CD8 T Cell Responses: Comparison with B7.1 and 4-1BBL," The Journal of Immunology 175:6368-6377 (2005).
Stein et al., "The Cytoplasmic Domain of CD28 Is both Necessary and Sufficient for Costimulation of Interleukin-2 Secretion and Association with Phosphatidylinositol 3'-Kinase," Molecular And Cellular Biology, (May 1994) 14(5):3392-3402.
Suhoski, M.M., et al., Engineering artificial antigen-presenting cells to express a diverse array of co-stimulatory molecules, Mol Ther, 2007. 15(5): p. 981-8.
Tamada (2013) Correction: Redirecting Gene-Modified T Cells toward Various Cancer Types Using Tagged Antibodies—Feb. 14, 2013.
Tamada, K. et al: Redirecting Gene-Modified T Cells toward Various Cancer Types Using Tagged Antibodies, Clinical Cancer Research, vol. 18, No. 23, Oct. 2, 2012 (Oct. 2, 2012), pp. 6436-6445.
Tanaka, Toshio et al. "Immunotherapeutic implications of IL-6 blockade for cytokine storm." Immunotherapy. Jul. 2016;8(8):959-70.
Teachey D. T. ET AL. "Cytokine release syndrome after blinatumomab treatment related to abnormal macrophage activation and ameliorated with cytokine-directed therapy" Blood. Jun. 27, 2013;121(26):5154-7. doi: 10.1182/blood-2013-02-485623. Epub May 15, 2013.
Tsukahara et al. "CD19 target-engineered T-cells accumulate at tumor lesions in human B-cell lymphoma xenograft mouse models" (2013) Biochem Biophys Res Common 438(1): 84-9. Epub Jul. 17, 2013.
Turtle et al., "Engineered T cells for anti-cancer therapy" Curr. Opin. Immunol., Oct. 2012; 24(5): 633-39. Epub Jul. 18, 2012.
UniProtKB—O43914, "TYRO protein tyrosine kinase-binding protein", pp. 1-15.
UniProtKB—P02701, AVidin Precursor—Gallus Chicken.
Urbanska, K., et al., "A Universal Immune Receptor Expressed by T Cells for the Targeting of Diverse and Multiple Tumor Associated Antigens" In Abstracts for the 26th Annual Scientific Meeting of the Society for Immunotherapy of Cancer (SITC), J Immunother, vol. 34, No. 9, Nov.-Dec. 2011 (62 pages), p. 381.
Verdine et al., "The Challenge of Drugging Undruggable Targets in Cancer: Lessons Learned from Targeting BCL-2 Family Members" Clin. Cancer Res. vol. 13, No. 24, Dec. 15, 2007, pp. 7264-7270.
Verhoeyen et al. "Lentiviral vector gene transfer into human T cells" (2009) Methods Mol Biol. 506: 97-114.
Wang et al. "Phenotypic and functional attributes of lentivirus-modified CD19-specific human CD8+ central memory T cells manufactured at clinical scale" (2012) J Immunother. 35(9):689-701.
Weissman et al., "Molecular cloning and chromosomal localization of the human T-cell receptor zeta chain: Distinction from the molecular CD3 complex" Proc. Natl. Acad. Sci. vol. 85, Dec. 1988, pp. 9709-9713.
Weissman et al., "Role of the zeta chain in the expression of the T cell antigen receptor: genetic reconstitution studies" The EMBO Journal, vol. 8, No. 12. 1989, pp. 3651-3656.
Wesolowski, J, et al., "Single domain antibodies: promising experimental and therapeutic tools in infection and immunity", Med Microbiol Immunol (2009) 198:157-174.
Wikipedia, Avidin, (2018) retrieved from https://en.wikipedia.org/w/index.php?title=Avidin&oldid=849308130.
Wu et al., "Adoptive T-cell therapy using autologous tumor-infiltrating lymphocytes for metastatic melanoma: current status and future outlook" Cancer, Mar. 18, 2012(2): 160-75.

(56) References Cited

OTHER PUBLICATIONS

Xu et al., "Cytokine release syndrome in cancer immunotherapy with chimeric antigen receptor engineered T cells" Cancer Lett. Feb. 28, 2014;343(2):172-8. Epub Oct. 16, 2013.
Zhang, H., et al., 4-IBB is superior to CD28 costimulation for generating CD8+ cytotoxic lymphocytes for adoptive immunotherapy. J Immunol, 2007. 179(7): p. 4910-8.
Zheng et al., "Arming Tumor-Reactive T Cells with Costimulator B7-1 Enhances Therapeutic Efficacy of the T Cells," Cancer Research, 2006, vol. 66, No. 13, pp. 6793-6799.
Lamers et al., "Immune responses to transgene and retroviral vector in patients treated with ex vivo-engineered T cells," Blood (2011) 117(1): 72-82.
Barocas et al., "A population-based study of renal cell carcinoma and prostate cancer in the same patients," BJU International, (2006) 97(1): 33-36.
Zhang et al., "Phase I Escalating-Dose Trial of CAR-T Therapy Targeting CEA+ Metastatic Colorectal Cancers," Molecular Therapy (2017), 25(5): 1248-1258.
Gargalionis et al, "The molecular rationale fo Src inhibition in colorectal carcinomas," Int. J. Cancer, 134:2019-2029 (2013).
Karachaliou et al., "Common Co-activation of AXL and CDCPI in EGFR-mutation-positive Non-smallcell Lung Cancer Associated with Poor Prognosis," EBioMedicine (2017) https://doi.org/10/1016/j.ebiom.2018.02.001.
PCT Search Report and Written Opinion prepared for PCT/US2017/026618, completed Aug. 30, 2017.
Rodgers, David T., et al., "Switch-mediated Activation and Retargeting of CAR-T Cells for B-cell Malignancies," Jan. 12, 2016, www.pnas.org/cgi/doi/10.1073/pnas.1524155113, pp. E459-E468.
Tamada, Koji, et al., "Redirecting Gene-Modified T Cells Toward Various Cancer Types Using Tagged Antibodies," 2012, American Association of Cancer Research, pp. 1-35.
Peng-Cheng, "Evaluation of a Carbonic Anhydrase IX-Targeted near-Infrared Dye for Fluorescence-Guided Surgery of Hypoxic Tumors," Mol. Pharmaceutics, 13:1618-1625 (2016).
Betancur et al., "Nonpeptide antagonists of neuropeptide receptors: tools for research and therapy," Trends Pharmacol Sci. 18(10): 372-386 (1997).
Hong, Soon-Sun et al., "A Novel Small-Molecule Inhibitor Targeting the IL-6 Receptor β Subunit, Glycoprotein 130," J Immunol 2015; 195:237-245; Prepublished online May 29, 2015;doi: 10.4049/jimmunol.1402908http://www.jimmunol.org/content/195/1/237.
Magee, M et al., "Challenges to chimeric antigen receptor (CAR)-T cell therapy for cancer," Discovery Medicine 18(100):265-271 (2014).
Marofi et al., "CAR T cells in solid tumors: challenges and opportunities," Stem Cell Research & Therapy 12:81, pp. 1-16 (2012).
Maus et al., "Antibody-modified T cells: CARs take the front seat for hematologic malignancies," BLOOD 123(17):2626-2635 (2014).
Miguel Muñoz, Rafael Coveñas,"Substance P," Encyclopedia of Endocrine Diseases (Second Edition), vol. 1, pp. 571-578 (2018).
Van Der Stegen et al., "The pharmacology of second- generation chimeric antigen receptors." Nature reviews Drug Discovery 14(7):499-509 (2015).
Farkas A, et al., "Proarrhythmic effects of intravenous quinidine, amiodarone, D-sotalol, and almokalant in the anesthetized rabbit model of torsade de pointes", Journal of Cardiovascular Pharmacology, Feb. 2002, vol. 39(2), pp. 287-297.
GenBank: AMZ04818.1, Zah, E. et al., dated Apr. 24, 2016, 6 pages.
Ren et al., "Safety Strategies of Genetically Engineered T Cells in Cancer Immunotherapy", Current Pharmaceutical Design, 2018, vol. 24(1), pp. 78-83.
Zah, E., et al., "T Cells Expressing CD19/CD20 Bispecific Chimeric Antigen Receptors Prevent Antigen Escape by Malignant B Cells," Cancer Immunology Research, Jun. 2016, vol. 4 (6), pp. 498-508.
Abate-Daga, et al., "Abstracts for the 25th Annual Scientific Meeting of the International Society for Biological Therapy of Cancer," Journal of Immunotherapy (2010); 33(8): 859-920.
Abken, H., et al., "Tuning tumor-specific T-cell activation: a matter of costimulation?" TRENDS in Immunology vol. 23 No. 5, May 2002: 240-45.
An, Z., et al., "IgG2m4, an engineered antibody isotype with reduced Fc function", MAbs (2009); 1(6): 572-579.
Barber, et al., "Chimeric NKG2D expressing T cells eliminate immunosuppression and activate immunity within the ovarian tumor microenvironment," J. Immunol. (2009); 183:6939-6947.
Barber, et al., Chimeric NKG2D Receptor-Expressing T Cells as an Immunotherapy for Multiple Myeloma, Exp Hematol. (Oct. 2008); 36(10)1318-28.
Barber, et al., "Immunotherapy with chimeric NKG2D receptors leads to long-term tumor-free survival and development of host antitumor immunity in murine ovarian cancer," J. immunol 180:72-78 (2008).
Barber, et al., J Immunol. (Aug. 1, 2014); 193(3): 1513, pp. 1-2: (Erratum to Barber et al. "Immunotherapy with chimeric NKG2D receptors leads to long-term tumor-free survival and development of host antitumor immunity in murine ovarian cancer," J. Immunol. (2008); 180:72-78).
Berger et al., "Safety of targeting ROR1 in primates with chimeric antigen receptor modified T cells," Cancer Immunology Research, 3(2):206-216 (2015).
BLAST Search page for "P20334[209-256]" (2 pages), retrieved from http://www.uniprot.org/blasV? about=P20334[209-256] &key= Topological %20domain on Oct. 14, 2016.
Boder et al., "Directed evolution of antibody fragments with monovalent femtomolar antigen-binding affinity," Proc Natl Acad Sci U S A 97(20):10701-10705 (2000).
Boulassel et al., "Immunotherapy for B-Cell Neoplasms using T Cells expressing Chimeric Antigen Receptors: From antigen choice to clinical implementation," Sultan Qaboos Univ Med J 12(3):273-285 (2012).
Brentjens et al., "Treatment of chronic lymphocytic leukemia with genetically targeted autologous T cells: case report of an unforeseen adverse event in a phase I clinical trial," Mol Ther 18(4):666-668 (2010).
Bridgeman, J.S., et al., "Structural and biophysical determinants of alpha beta T-cell antigen recognition," Immunology (Jan. 2012); 135(1 ): 9-18 (First published: Dec. 7, 2011 ).
Camerini, D, et al., "The T cell activation antigen CD27 is a member of the nerve growth factor/tumor necrosis factor receptor gene family," The Journal of Immunology (1991); 3165-3169.
Carpenito C., et al., Control of large, established tumor xenografts with genetically retargeted human T cells containing CD28 and CD137 domains. Proc Natl Acad Sci U S A. Mar. 3, 2009;106(9):3360-5. doi: 10.1073/pnas.0813101106. Epub Feb. 11, 2009. PMID: 19211796; PMCID: PMC2651342.
Carpenter, R. O., et al. "B-cell Maturation Antigen is a Promising Target for Adoptive T-cell Therapy of Multiple Myeloma," Clinical Cancer Research, 2013, vol. 19(8), pp. 2048-2060.
"Chain A, 4m5.3 Anti-Fluorescein Single Chain Antibody Fragment (Scfv)" (4 pages), retrieved from https://www.ncbi.nlm.nih.gov/protein/62738392?report=genbank&log$=protalign&blast_rank=I &RID=UWAEY60801 Ron Oct. 12, 2016.
Chen, et al. "Chimeric antigen receptor (CAR)-directed adoptive immunotherapy: a new era m targeted cancer therapy," Stem Cell Investig. (Jan. 18, 2014); 1:2 (2 pages).
Cheng et al., "Hapten-directed targeting to single-chain antibody receptors," Cancer Gene Therapy, 11(5):380-388 (2004).
Chothia, et al., "Conformations of immunoglobulin hypervariable regions," Nature, Dec. 28, 1989, vol. 342, pp. 877-883.
Cianciulli, A. et al., "Folic Acid Is Able to Polarize the Inflammatory Response in LPS Activated Microglia by Regulating Multiple Signaling Pathways", Mediators of Inflammation, 2016, 10 pages.
Clay, et al., "Efficient transfer of a tumor antigen-reactive TCR to human peripheral blood lymphocytes confers anti- tumor reactivity," J. Immunol. (1999); 163:507-153.
Cooper, "Test-driving CARs," Blood (Sep. 15, 2008); 112(6):2172-3.
Co-pending U.S. Appl. No. 61/891,347, inventors Cao; Yu et al., filed Oct. 15, 2013.

(56) References Cited

OTHER PUBLICATIONS

Dai, et al., "Chimeric Antigen Receptors Modified T-Cells for Cancer Therapy," J Natl Cancer Inst (2016); 108(7): djv439 (14 pages) (First published online Jan. 27, 2016).

Davila et al., "CD19 CAR-targeted T cells induce long-term remission and B Cell Aplasia in an immunocompetent mouse model of B cell acute lymphoblastic leukemia," PLOS One 8(4) e61338 (2013), 14 pages.

Davila ML, et al., "How do CARs work?: Early insights from recent clinical studies targeting CD19," Oncoimmunology (Dec. 2012 I); 1(9):1577-1583.

Deng et al., "Antitumor activity of NKG2D CAR-T cells against human colorectal cancer cells in vitro and in vivo," Am J Cancer Res 9(5)945-958 (2019).

Eshhar, Z., et al., "Specific activation and targeting of cytotoxic lymphocytes through chimeric single chains consisting of antibody-binding domains and the gamma or zeta subunits of the immunoglobulin and T-cell receptors," Proc. Natl. Acad. Sci. USA (1993); 90: 720-724.

Eshhar, et al., "Design of Cytotoxic T Lymphocytes with Antibody-Type Specificity against Tumor Cells Using Chimeric TcR," Journal of Cellular Biochemistry, Supplement 14B, UCLA Symposia on Molecular & Cellular Biology, Abstracts, 19th Annual Meeting, Jan. 27-Feb. 8, 1990, p. 70.

Eshhar, Z., et al., "Chimeric T cell receptor which incorporates the anti-tumour specificity of a monoclonal antibody with the cytolytic activity of T cells: a model system for immunotherapeutical approach," Br J Cancer. Suppl. (Jul. 1990); 10: 27-29.

Extended European Search Report issued by the European Patent office for Application No. 18761400.3, dated Sep. 24, 2020, 7 pages.

Extended European Search Report issued by the European Patent Office for Application No. 19204092.1, dated Mar. 16, 2020, 8 pages.

Extended European Search Report issued by the European Patent Office for Application No. 19740881.8, dated Oct. 10, 2021, 9 pages.

Extended European Search report issued by the European Patent Office for Application No. 19741309.9, dated Oct. 5, 2021, 12 pages.

Extended European Search Report issued by the European Patent Office for Application No. 19757681.2, dated Nov. 25, 2021, 9 pages.

Extended European Search report issued by the European Patent Office for Application No. 23169858.0, dated Oct. 30, 2023, 9 pages.

Extended European Search Report issued by the European Patent Office for Appliction No. EP17779919, dated Nov. 6, 2019, 7 pages.

Fang, R.H., et al., "Lipid-insertion Enables Targeting Functionalization of Erythrocyte Membrane-cloaked Nanoparticles," Nanoscale, Oct. 2013, vol. 5(19), pp. 8884-8888.

FDA Approval Letter dated Apr. 23, 2014, for Biologics License Application for SYLVANT™ (siltuximab), 12 pages.

FDA Approval Letter dated Jan. 8, 2010, for Biologics License Application for Acternra (tocilizumab), 9 pages.

Figini, M, et al., "Panning phage antibody libraries on cells: isolation of human Fab fragments against ovarian carcinoma using guided selection," Cancer Res (Mar. 1, 1998); 58(5):991-996.

Finney et al., "Activation of resting human primary T cells with chimeric receptors: costimulation from CD28, inducible costimulator, CD134, and CD137 in series with signals from the TCR zeta chain," J. Immunol., 172(1):104-113, Jan. 2004.

Finney et al., "Chimeric Receptors Providing Both Primary and Costimulatory Signaling in T Cells from a Single Gene Product," J Immunol161, 2791-2797 (1998).

Fitzer-Attas et al., "Harnessing Syk family tyrosine kinases as signaling domains for chimeric single chain of the variable domain receptors: optimal design for T cell activation," J. Immunol., 160(1): 145-54, Jan. 1998.

Friedmann-Morvinski, D., et al., "Redirected primary T cells harboring a chimeric receptor require co stimulation for their antigen-specific activation," Blood (2005); 105(8): 3087-3093.

Gade et al., "Targeted elimination of prostate cancer by genetically directed human T lymphocytes," Cancer Res. (2005); 65:9080-9088.

Gill et al., "Preclinical targeting of human acute myeloid leukemia and myeloablation using chimeric antigen receptor-modified T cells," Blood (2014); 123(15): 2343-54 (pub online Mar. 4, 2014).

Gong, et al., "Cancer Patient T Cells Genetically Targeted to Prostate Specific Membrane Antigen Specifically Lyse Prostate Cancer Cells and Release Cytokines in Response to Prostate-Specific Membrane Antigen," Neoplasia (1999); 1:123-7.

Grada et al., "TanCAR: a novel bispecific chimeric antigen receptor for cancer immunotherapy," Molecular Therapy- Nucleic Acids (2013): 2(7): Article No. e1 05 (internal pp. 1-11) (e-pub. Jul. 9, 2013).

Griffioen, M., et al., "Retroviral transfer of human CD20 as a suicide gene for adoptive T-cell therapy," Haematologica (2009); 94(9): 1316-20.

Grosenbach et al., "A recombinant vector expressing transgenes for four T -cell costimulatory molecules (OX40L, B7-1, ICAM-1, LFA-3) induces sustained CD4+ and CDS+ T-cell activation, protection from apoptosis, and enhanced cytokine production," Cellular Immunology 222 (2003) 45-57.

Gross et al., "Chimaeric T-cell receptors specific to a B-lymphoma idiotype: a model for tumour immunotherapy," Biochem. Soc. Trans. (Nov. 1995); 23(4):1079-82.

Grupp, S.A. et al., "Chimeric antigen receptor-modified T cells for acute lymphoid leukemia", N Engl J Med. (2013); 368(16): 1509-1518.

Gu et al., "Abstract LB-187: New methods for controlling Car T cell-mediated cytokine storms : Cancer Research", Proceedings: AACR Annual Meeting 2017, (Jul. 1, 2017), Retrieved from the Internet Sep. 28, 2021: URL:https://cancerres.aacrjournals.org/content/77/13 Supplement/LB-187, 4 pages.

Hansen et al., "Description of an Ectothermic TCR Coreceptor, CD8 a, in Rainbow Trout," J. Immunol., 164, 3132-3139, 2000.

Helen E Heslop: "Safer CARS", Molecular Therapy, vol. 18, No. 4, Apr. 1, 2010, 2 pages.

Heslop, "Genetic engineering of T-cell receptors: TCR takes to titin," Blood (Aug. 8, 2013); 122(6):853-4.

Ho, et al., "Adoptive Immunotherapy: Engineering T Cell Responses as Biologic Weapons for Tumor Mass Destruction," Cancer Cell (May 2003); 3:431-7.

Hombach, et al., J Immunol (2004); 173: 695: (Erratum to Hombach, et al., Tumor-specific T cell activation by recombinant immunoreceptors: CD3 zeta signaling and CD28 costimulation are simultaneously required for efficient IL.

Hombach, et al., "Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule," J Immunol. (2001); 167:6123-6131.

Honegger et al., "A mutation designed to alter crystal packing permits structural analysis of a tight-binding fluorescein-scFv complex," Protein Science 14(10): 2537-2549 (2005).

Hudecek et al., "Receptor affinity and extracellular domain modifications affect tumor recognition by ROR1-specific chimeric antigen receptor T-cells," Clin Cancer Res. 19(12):3153-3164 (2013).

Hunter et al., "Inhibition of Fcy Receptor-Mediated Phagocytosis by a Nonphagocytic Fcy Receptor," Blood, vol. 91, No. 5 Mar. 1, 1998: pp. 1762-1768.

Hwu, P., et al., "In Vivo Antitumor Activity of T Cells Redirected with Chimeric Antibody/T-Cell Receptor Genes," Cancer Research (Aug. 1, 1995); 55: 3369-3373.

Hwu, P. et al., "Lysis of Ovarian Cancer Cells by Human Lymphocytes Redirected with a Chimeric Gene Composed of an Antibody Variable Region and the Fc Receptor gamma-Chain," The Journal of Experimental Medicine (1993); 178, 361-366.

International Search Report and Written Opinion dated Mar. 27, 2019 for PCT/US2019/014478, 8 pages.

(56) References Cited

OTHER PUBLICATIONS

International Search Report issued in Appl. No. PCT/US2019/014472 (Apr. 26, 2019), 15 pages.
Israeli, R. S., et al., "Expression of the prostate-specific membrane antigen," Cancer Res. (1994); 54, 1807-1811.
Jensen, M. C., et al., "Human T lymphocyte genetic modification with naked DNA," Molecular Therapy (2000); 1:49-55.
Johnson et al., "Kabat database and its applications: 30 years after the first variability plot," Nucleic Acids Res., 28(1): 214-218 (2000).
Johnson, L. A. et al., "Gene therapy with human and mouse T-cell receptors mediates cancer regression and targets normal tissues expressing cognate antigen," Blood , vol. 114, No. 3, pp. 535-546 (Jul. 2009).
Junghans RP, "Is it safer CARs that we need, or safer rules of the road?," Mol Ther. (Oct. 2010); 18(10):1742-3.
Kabat et al., Abstract, Sequence of Proteins of Immunological Interest, US Public Health Services, NIH, Bethesda, MD, Publication No. 91-3242, 3 pages, (1991).
Kalos et al., "T Cells with Chimeric Antigen Receptors Have Potent Antitumor Effects and Can Establish Memory in Patients with Advanced Leukemia," Sci. Transl. Med. (Aug. 10, 2011) 3(95)1-21.
Kanduluru et al., "Design, Synthesis, and Evaluation of a Neurokinin-1 Receptor-Targeted Near-IR Dye for Fluorescence-Guided Surgery of Neuroendocrine Cancers," Bioconjugate Chem. 27, 2157-2165 (2016).
Kenderian, et al.; "CD33-specific chimeric antigen receptor T cells exhibit potent preclinical activity against human acute myeloid leukemia," Leukemia (Aug. 2015); 29(8): 1637-47 (Epub Feb. 27, 2015).
Kershaw et al., "Gene-Engineered T Cells as a Superior Adjuvant Therapy for Metastatic Cancer," The Journal of Immunology 173(3): 2143-2150 (2004).
Kershaw, M. H. et al., "A Phase I Study on Adoptive Immunotherapy Using Gene-Modified T Cells for Ovarian Cancer," Clin Cancer Res, 12(20):6106-6115 (Oct. 2006).
Kim et al., "NMR Structural Studies of Interactions of a Small, Nonpeptidyl Tpo Mimic with the Thrombopoietin Receptor Extracellular Juxtamembrane and Transmembrane Domains," J Biol Chem (2007) 282(19)14253-14261.
Kochenderfer, J.N., et al., "Adoptive transfer of syngeneic T cells transduced with a chimeric antigen receptor that recognizes murine CD19 can eradicate lymphoma and normal B cells.," Blood (2010); 116(19):3875-3886.
Kowolik, C et al., "CD28 costimulation provided through a CD19-specific chimeric antigen receptor enhances in vivo persistence and antitumor efficacy of adoptively transferred T cells", Cancer Res. (2006); 66(22): 10995-11004.
Kowolik, et al., "CD28-costimulation provided through a CD-19-specific chimeric immunoreceptor enhances in vivo persistence and anti-tumor efficacy of adoptively transferred T cells," Blood 106(11): 1278, 4 pages (2005) (Retrieved from http://www.bloodjournal.org/contentU106/11/1278).
Kozak, M. et al., "At least six nucleotides preceding the AUG initiator codon enhance translation in mammalian cells," Journal of Molecular Biology, vol. 196(4):947-950 (1987).
Kranz et al., "Partial elucidation of an anti-hapten repertoire in BALB/c mice comparative characterization of several monoclonal Anti-Fluorescyl antibodies," Mol Immunol (1981) 18(10):889-898.
Krause et al., "Antigen-dependent CD28 Signaling Selectively Enhances Survival and Proliferation in Genetically Modified Activated Human Primary T Lymphocytes," J. Exp. Med. 188(4):619-626 (1998).
Kunik et al., "Paratome: an online tool for systematic identification of antigen-binding regions in antibodies based on sequence or structure," Nucl Acids Res. 40:W521-W524 (2012).
Laroche et al., "Characterization of a Recombinant Single-chain Molecule Comprising the Variable Domains of a Monoclonal Antibody Specific for Human Fibrin Fragment D-dimer*," The Journal of Biological Chemistry 1991, vol. 266, No. 25, Issue of September 5, pp. 16343-16349.
Le et al. "FDA Approval Summary: Tocilizumab for Treatment of Chimeric Antigen Receptor T Cell-Induced Severe or Life-Threatening Cytokine Release Syndrome," The Oncologist 23:943-947 (2018).
Lee et al., "Use of a Single CAR T Cell and Several Bispecific Adapters Facilitates Eradication of Multiple Antigenically Different Solid Tumors," Cancer Res 79:387-396 (2019).
Lefranc, MP et al., "IMGT unique numbering for immunoglobulin and T cell receptor variable domains and Ig superfamily V-like domains," Developmental & Comparative Immunology, Jan. 2003, 27(1), pp. 55-77.
Letourneur et al. "T-cell and basophil activation through the cytoplasmic tail of T-cell-receptor zeta family proteins" Proc. Natl. Acad. Sci USA (1991); 88:8905-8909.
Li et al., "CAIX-specific CAR-T Cells and Sunitinib Show Synergistic Effects Against Metastatic Renal Cancer Models," Journal of Immunotherapy 4316-4328 (2020).
Linette et al., "Cardiovascular toxicity and titin cross-reactivity of affinity-enhanced T cells in myeloma and melanoma," Blood (Aug. 8, 2013); 122(6): 863-71 (Epub Jun. 14, 2013).
Liou et al., "A chimeric mouse-human antibody that retains specificity for HIV gp 120 and mediates the lysis of HIV-infected cells," J Immunol 1989; 143: 3967-3975.
Liu et al., "Monoclonal Antibodies to the Extracellular Domain of Prostate-Specific Membrane Antigen Also React With Tumor Vascular Endothelium," Cancer Res. (1997); 57(17): 3629-3634.
Lowin-Kropf et al., "Cytoskeletal Polarization of T Cells Is Regulated by an Immunoreceptor Tyrosine-based Activation Motif-dependent Mechanism," The Journal of Cell Biology 1998, vol. 140, No. 4, pp. 861-871.
Lu et al., "Preclinical Evaluation of Bispecific Adaptor Molecule Controlled Folate Receptor CAR-T Cell Therapy With Special Focus on Pediatric Malignancies", Frontiers in Oncology, vol. 9, pp. 1-20 (2019).
Lu et al., "Strategy to prevent drug-related hypersensitivity in folate-targeted hapten immunotherapy of cancer," AAPS J 11(3):628-638 (2009).
Ma et al., "Targeting of antigens to B lymphocytes via CD19 as a means for tumor vaccine development," Journal of Immunology 190(11):5588-5599 (2013).
Maher, J., Immunotherapy of malignant disease using chimeric antigen receptor engrafted T cells. International Scholarly Research Notices Oncology, 2012:278093 (2012).
Makabe et al., "Thermodynamic consequences of mutations in Vernier zone residues of a humanized anti-human epidermal growth factor receptor murine antibody," Journal of Biological Chemistry, 283(2):1156-1166 (2008).
Manual pCDH Vectors (System Biosciences) (21 pages), Nov. 18, 2013.
Martin et al., "Modeling antibody hypervariable loops: a combined algorithm," Proc Natl Acad Sci (USA), 86:9268-9272 (1989).
Maus, et al., "Zoom Zoom: racing CARs for multiple myeloma," Clin Cancer Res. (Apr. 15, 2013); 19(8):1917-9 (Epub Feb. 26, 2013.).
Midelfort, KS, et al., "Substantial Energetic Improvement with Minimal Structural Perturbation in a High Affinity Mutant Antibody," J. Mol Biol. 343:685-701, 2004.
Milone et al., "Chimeric receptors containing CD137 signal transduction domains mediate enhanced survival of T cells and increased antileukemic efficacy in vivo", Mol Ther. Aug. 2009; 17(8): 1453-64. Epub Apr. 21, 2009.
Molecular Cloning a Laboratory Manual, 4th Edition, Cold Spring Harbor Laboratory Press, (2012) Green and Sambrook, TOC, 34 pages (2012).
Moore et al., "Application of dual affinity retargeting molecules to achieve optimal redirected T-cell killing of B-cell lymphoma," Blood, The Journal of the American Society of Hematology, Apr. 2011, 117(17), pp. 4542-4551.
Moore et al., "Characterisation of salmon and trout CD8a and CD8I3," Molecular Immunology 42 (2005) 1225-1234.

(56) References Cited

OTHER PUBLICATIONS

Moretta et al., "Activating Receptors and Coreceptors Involved in Human Natural Killer Cell-Mediated Cytolysis," Annu. Rev. Immunol. 2001. 19:197-223.

Morgan RA et al., "Case Report of a Serious Adverse Event Following the Administration of T Cells Transduced With a Chimeric Antigen Receptor Recognizing Erbb2," Molecular Therapy 18(4):843-851 (2010).

Moritz, D. et al., "Cytotoxic T lymphocytes with a grafted recognition specificity for ERBB2-expressing tumor cells," Proc Natl Acad Sci U S A. May 10, 1994; 91(10): 4318-4322.

Munn et al., "Role of Low-Affinity Fe Receptors in Antibody-dependent Tumor Cell Phagocytosis by Human Monocyte-derived Macrophages," Cancer Research 51, 1117-1123, Feb. 15, 1991.

Nelson, Aaron L., "Antibody fragments," mAbs 2010, Landes Bioscience, vol. 2, Issue 1, pp. 77-83.

Nolan K F, et al., "Bypassing immunization: optimized design of 'designer T cells' against carcinoembryonic antigen (CEA)-expressing tumors, and lack of suppression by soluble CEA," Clinical Cancer Research (Dec. 1999); 5(12): 3928-3941.

Patel et al., "T -cell killing of heterogenous tumor or viral targets with bispecific chimeric immune receptors," Cancer Gene Therapy (2000); 7(8): 1127-1134.

PCT Search Report and Written Opinion prepared for PCT/US2018/020095, completed Jul. 17, 2018, 12 pages.

Pierce, et al., "Computational Design of the Affinity and Specificity of a Therapeutic T Cell Receptor" PLOS Computational Biology (Feb. 13, 2014); 10(2): e1003478 (11 pages).

Pinto et al., "Molecular cloning and characterization of sea bass (*Dicentrarchus labrax* L.) CD8α," Veterinary Immunology and Immunopathology, 110, 169-177, 2006.

Pizarro, J.C., et al., "Structural and functional characterization of a monoclonal antibody specific for the preSI region of hepatitis B virus," FEBS letters (2001); 509: 463-468.

Pule et al., "Virus-specific T cells engineered to coexpress tumor-specific receptors: persistence and antitumor activity in individuals with neuroblastoma," Nat. Med. (2008); 14: 1264-1270.

Rabu et al., "Production of Recombinant Human Trimeric CD137L (4-1BBL), Cross-linking is Essential to its T Cell Co-Stimulation Activity," The Journal of Biological Chemistry vol. 280, No. 50, pp. 41472-41481, Dec. 16, 2005.

Rader, "DARTs take aim at BiTEs," Blood (Apr. 28, 2011); 117(17):4403-4.

Roberts, et al., "Antigen-specific cytolysis by neutrophils and NK cells expressing chimeric immune receptors bearing zeta or gamma signaling domains," J. Immunol. (1998); 161:375-84.

Rossi, et al., "2730 Phase 1 Biomarker Analysis of the ZUMA-1 (KTE-CI9-1 01) Study: A Phase 1-2 Multi-Center Study Evaluating the Safety and Efficacy of Anti-CD19 Cart Cells (KTEC19) in Subjects with Refractory Aggressive Non-Hodgkin Lymphoma (NHL)," American Society of Hematology (2015) (https://ash.confex.com/ash/20 15/webprogramscheduler/Paper80339. html) (2 pages) (presentation date Dec. 6, 2015).

Samudrala et al., "Ab Initio Protein Structure Prediction Using a Combined Hierarchical Approach," PROTEINS, Structure, Function and Genetics Suppl., 3:194-198 (1999).

Sang et al., "The research development of Chimeric Antigen Receptor T-cells in hematological malignancies," Practical Oncology Journal, vol. 30, No. 5, (Oct. 28, 2016), pp. 473-476.

Schutsky, K, et al., "Rigorous optimization and validation of potent RNA CAR T cell therapy for the treatment of common epithelial cancers expressing folate receptor," Oncotarget (Oct. 6, 2015); 6(30):28911-28.

Schwesinger et al., "Unbinding forces of single antibody-antigen complexes correlate with their thermal dissociation rates," PNAS (2000) 97(18), 9972-9977.

Shishkin A.M., Development of a method of adoptive immunotherapy of cancer-embryonic antigen positive human tumors, Moscow, FGBU "Russian Scientific Center of radiology and nuclear medicine," 2015, 23 pages including English Summary.

Song, DG, et al., "A fully human chimeric antigen receptor with potent activity against cancer cells but reduced risk for off-tumor toxicity," Oncotarget (Aug. 28, 2015);6(25):21533-46.

Song, DG, et al., "CD27 costimulation augments the survival and antitumor activity of redirected human T cells in vivo," Blood (Jan. 19, 2012); 119(3):696-706 (Epub Nov. 23, 2011).

Song et al., "In vivo persistence, tumor localization and anti-tumor activity of CAR engineered T cells is enhanced by costimulatory signaling through CD137 (4-IBB)," Cancer Research (2011); 71:4617-27.

Stephan, M. et al., "T cell-encoded CD80 and 4-1BBL induce auto- and transcostimulation, resulting in potent tumor rejection", Nat Med. (2007); 13(12): 1440-1449.

Stone, J.D., et al., "A sensitivity scale for targeting T cells with chimeric antigen receptors (CARs) and bispecific T-cell Engagers (BITEs)," Oncoimmunology (Sep. 2012); 1(6): 863-873.

Sun et al., "Immunotherapy with CAR-Modified T cells: toxicities and overcoming strategies," Journal of Immunology Research, 2018:1-10 (2018).

Swanson et al., "The coordination of signaling during Fe receptor-mediated phagocytosis," Journal of Leukocyte Biology, vol. 76, Dec. 2004, pp. 1093-1103.

Tan et al., "Influence of the hinge region on complement activation, C1q binding, and segmental flexibility in chimeric human immunoglobulins," Proc. Natl. Acad. Sci. USA 87:162-166, (1990).

Terakura et al., "Generation of CD19-chimeric antigen receptor modified CD8+ T cells derived from virus-specific central memory T cells," Blood 119(1):72-82 (2012) e-pub Oct. 26, 2011.

Till et al., "Adoptive immunotherapy for indolent non-Hodgkin lymphoma and mantle cell lymphoma using genetically modified autologous CD20-specific T cells," Blood 112(6): 2261-2271 (2008).

Traversari et al., "The potential immunogenicity of the TK suicide gene does not prevent full clinical benefit associated with the use of TK-transduced donor lymphocytes in HSCT for hematologic malignancies," Blood 109(11):4708-4715 (2007).

Uherek et al., "Retargeting of natural killer-cell cytolytic activity to ErbB2 expressing cancer cells results in efficient and selective tumor cell destruction," Blood (2002); 100: 1265-1273.

"UniProtKB—P24161 (CD3Z_MOUSE)" (12 pages), retrieved from http://www.uniprot.org/uniproVP24161 on Oct. 14, 2016.

Urbanska, K. et al., "Development of a novel universal immune receptor for antigen targeting: To Infinity and beyond," Oncoimmunology (Aug. 2012 I); 1(5): p. 777-779.

U.S. Appl. No. 61/473,409, inventor Morgan; Richard, filed Apr. 8, 2011.

U.S. Appl. No. 61/701,056, inventor Robbins; Paul, filed Sep. 14, 2012.

U.S. Appl. No. 61/891,347, inventor Cao:Yu, filed Oct. 15, 2013.

U.S. Appl. No. 61/895,704, inventor Cao:Yu, filed Oct. 25, 2013.

U.S. Appl. No. 62/009,054, inventor Young:Travis, filed Jun. 6, 2014.

U.S. Appl. No. 62/009,056, inventor Cao:Yu, filed Jun. 6, 2014.

U.S. Appl. No. 62/030,514, inventor Wang; Feng, filed Jul. 29, 2014.

U.S. Appl. No. 62/030,526, inventor Wang; Feng, filed Jul. 29, 2014.

U.S. Appl. No. 62/059,752, inventor Kim:Chanhyuk, filed Oct. 3, 2014.

U.S. Appl. No. 62/108,947, inventor Kim:Chanhyuk, filed Jan. 28, 2015.

U.S. Appl. No. 62/148,063, inventor Young: Travis, filed Apr. 15, 2015.

U.S. Appl. No. 62/148,070, inventor Kim:Chanhyuk, filed Apr. 15, 2015.

U.S. Appl. No. 62/253,465, inventor Kim:Chanhyuk, filed Nov. 10, 2015.

U.S. Appl. No. 62/253,467, inventor Young:Travis, filed Nov. 10, 2015.

Van Blitterswijk et al., "Anticancer mechanisms and clinical application of alkylphospholipids," Biochimica et Biophysica Acta (2013) 1831(3)663-674.

(56) References Cited

OTHER PUBLICATIONS

Van Der Luit et al., "A new class of anticancer alkylphospholipids uses lipid rafts as membrane gateways to induce apoptosis in lymphoma cells," Mol Cancer Ther (2007) 6(8)2337-2345.

Van Rhijn I. V., et al., "Human Autoreactive T Cells Recognize CD1band Phospholipids," Proceedings of the National Academy of Sciences, Nov. 30, 2015, vol. 113(2), pp. 380-385.

Webpage, COVID-19 Treatment Guidelines—Interleukin-6 Inhibitors, dated Sep. 26, 2022, 5 pages, retrieved online on Oct. 7, 2022 at https://www.covid19treatmentguidelines.nih.gov/therapies/immunomodulators/interleukin-6-inhibitors/.

Wikipedia, Killer-cell immunoglobulin-like receptor, https://en.wikipedia.org/wiki/Killer-cell immunoglobulin-like receptor, downloaded Jul. 25, 2018, 9 pages, undated.

Wikipedia, KLRAI, https://en.wikipedia.org/wiki/KLRAI, downloaded Jul. 25, 2018, 2 pages, undated.

Wikipedia, NKG2D, https://en.wikipedia.org/wiki/NKG2D, downloaded Jul. 25, 2018, 8 pages, undated.

Wikipedia, Paratope, https://en.wikipedia.org/wiki/Paratope, downloaded Jul. 25, 2018, 1 page.

Wilkie et al., "Retargeting of Human T Cells to Tumor-Associated MUC1: The Evolution of a Chimeric Antigen Receptor," The Journal of Immunology Apr. 2008, pp. 4901-4909.

WO2010025177—Sequence Listing (Mar. 4, 2010), 45 pages.

Zacchetti, A, "Antitumor effects of a human dimeric antibody fragment 131I-AFRA-DFM5.3 in a mouse model for ovarian cancer," J Nucl Med (Dec. 2011); 52(12):1938-46 (Epub Nov. 8, 2011).

Zarour, "Reversing T-cell dysfunction and exhaustion in cancer," Clinical Cancer Research, 22(8):1856-1864 (2016).

Zhang, et al., "Chimeric NKG2D modified T cells inhibit systemic T-cell lymphoma growth in a manner involving multiple cytokines and cytotoxic pathways," Cancer Res. (2007); 67(22): 11029-36.

Zhang, et al., "Generation of antitumor responses by genetic modification of primary human T cells with a chimeric NKG2D receptor," Cancer Res. (2006); 66(11):5927-33.

Zhang, T. (2005). Chimeric NK-receptor-bearing T cells mediate antitumor immunotherapy. Blood 106, 1544-1551.

Zheng, F. et al., "Relationship between levels of serum folate and inflammatory cytokines in hypertension cases." Zhongguo Redai Yixue (2015), 15(5), 521-524.

Zhong X-S., et al., "Chimeric Antigen Receptors Combining 4-1BB and CD28 Signaling Domains Augment PI3kinase/AKT/Bcl-XL Activation and CD8+ T Cell- mediated Tumor Eradication," Molecular Therapy, Feb. 2010, 18(2):413-420.

"Canadian Application Serial No. 3,019,835, Non-Final Office Action mailed Jun. 1, 2023", 4 pgs.

"European Application Serial No. 17779919.4, Communication Pursuant to Article 94(3) EPC mailed Jun. 17, 2024", 6 pgs.

"Indian Application Serial No. 201817041934, Hearing Notice mailed May 3, 2024", 4 pgs.

"International Application Serial No. PCT/US2017/026618, International Preliminary Report on Patentability mailed Oct. 18, 2018", 9 pgs.

"Japanese Application Serial No. 2023-081216, Notification of Reasons for Refusal mailed Jul. 9, 2024", w English translation, 4 pgs.

"Indian Application Serial No. 201817041934, Response filed Jul. 25, 2024 to Hearing Notice mailed May 3, 2024", 21 pgs.

\* cited by examiner

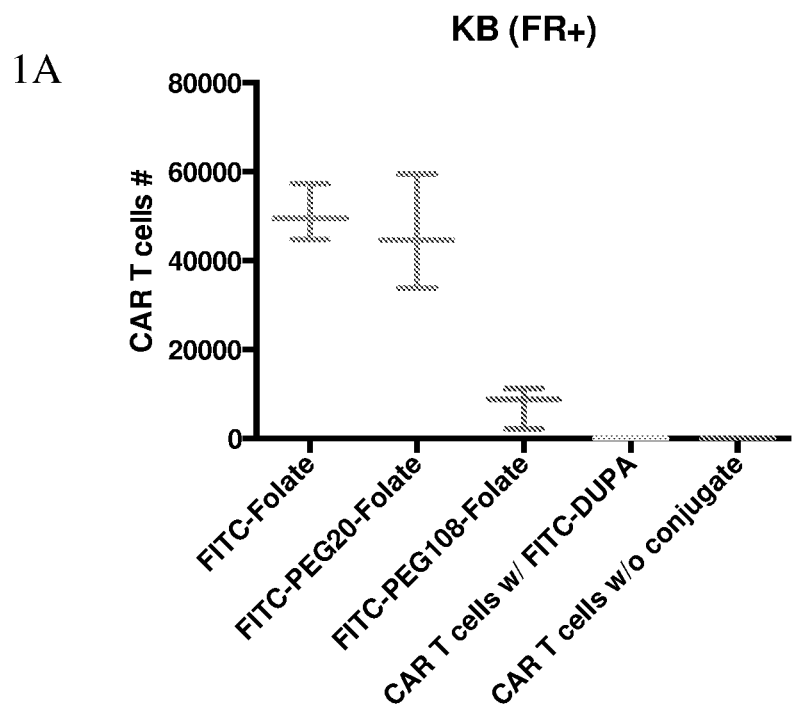
FIGURES 1A-B

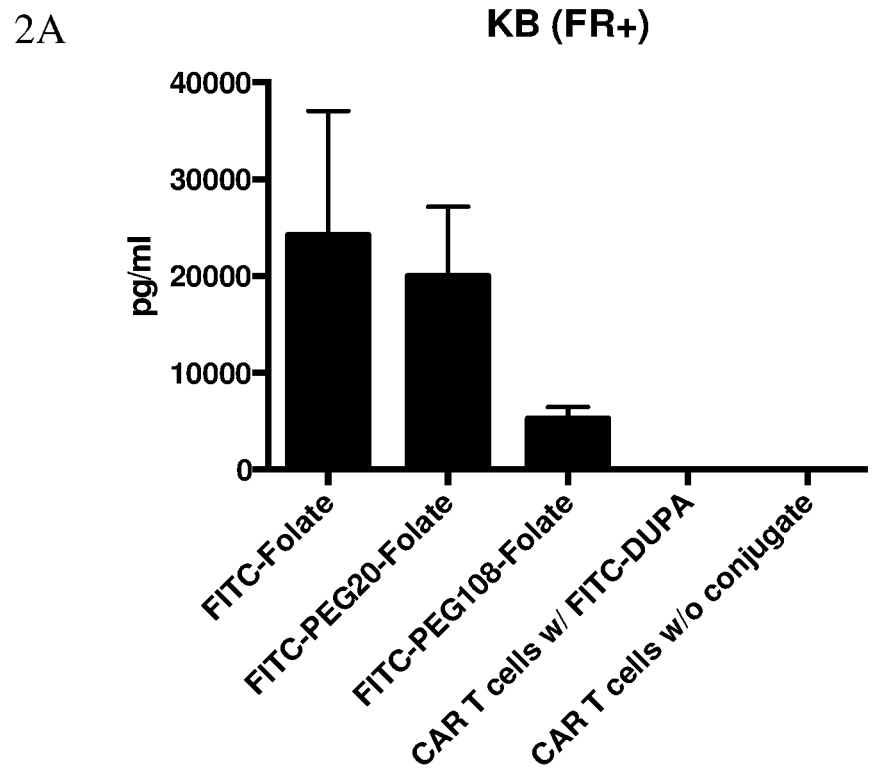
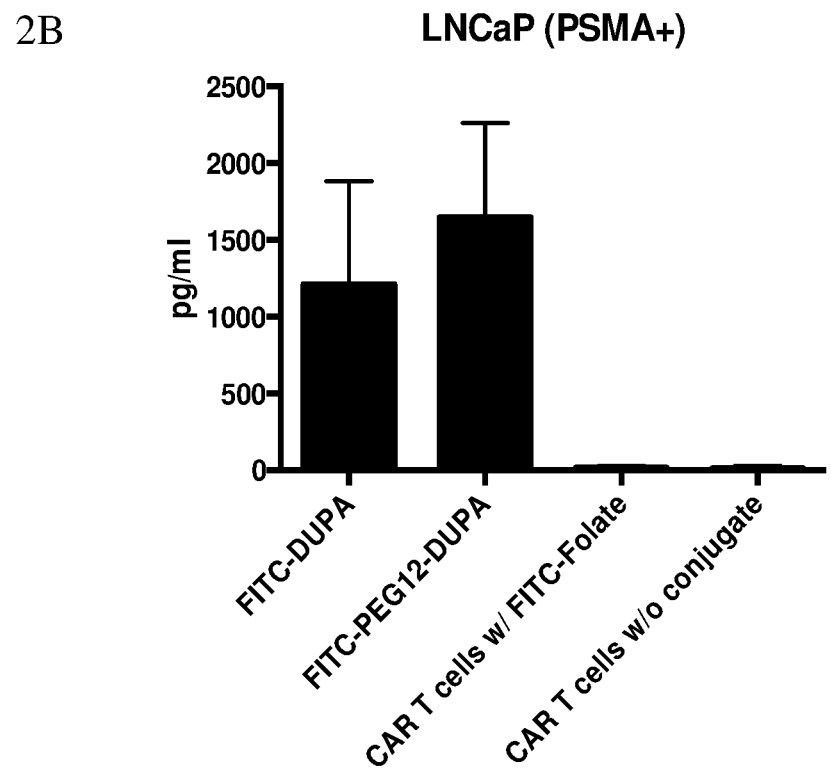
FIGURES 2A-F continued

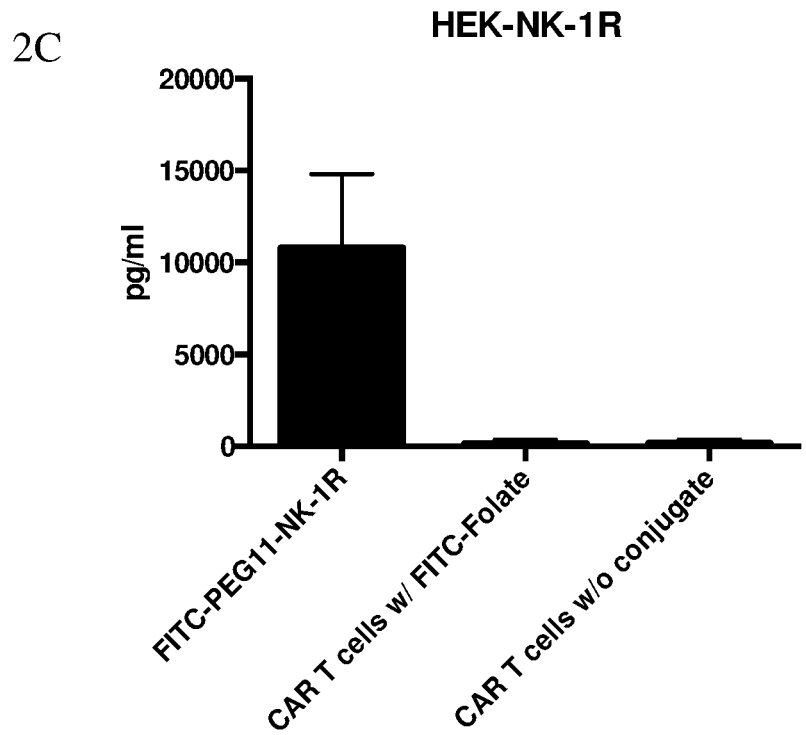
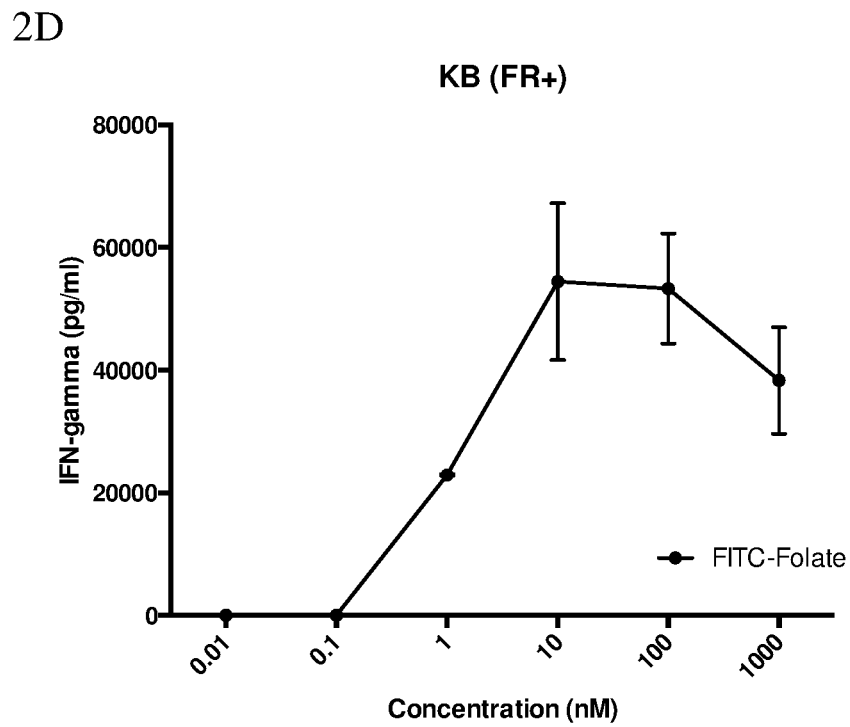
FIGURES 2A-F continued

2E
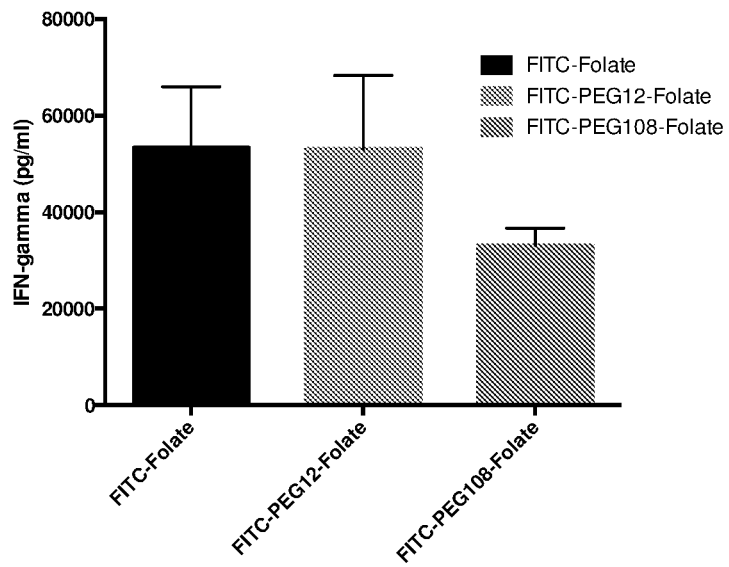
2F
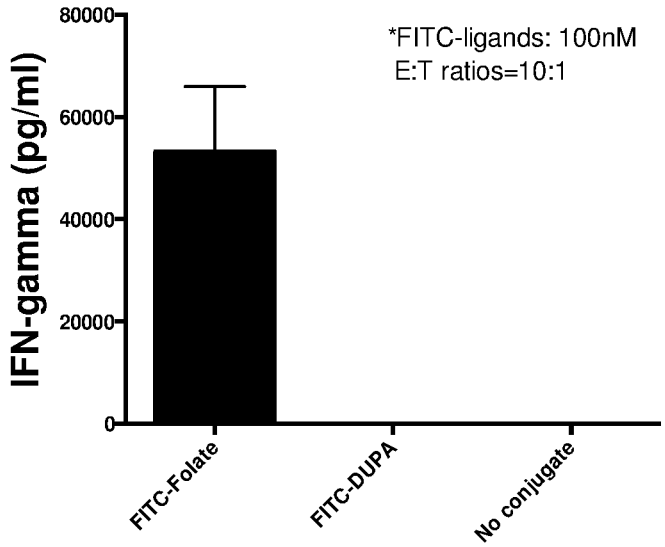
FIGURES 2A-F

3A
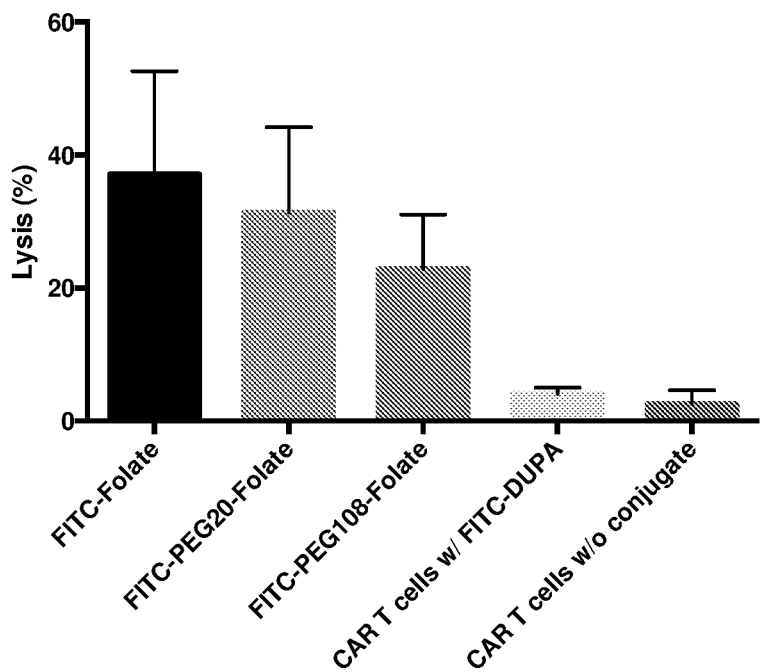
3B
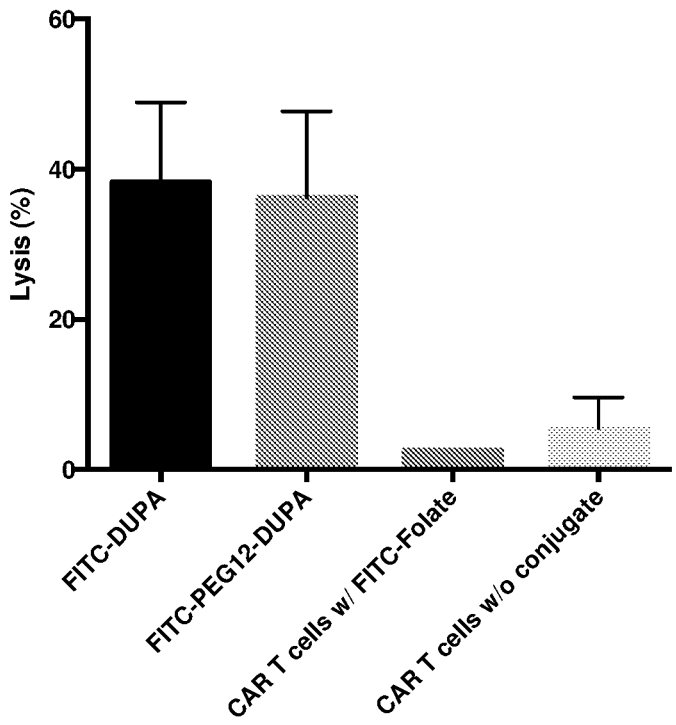
FIGURES 3A-F continued

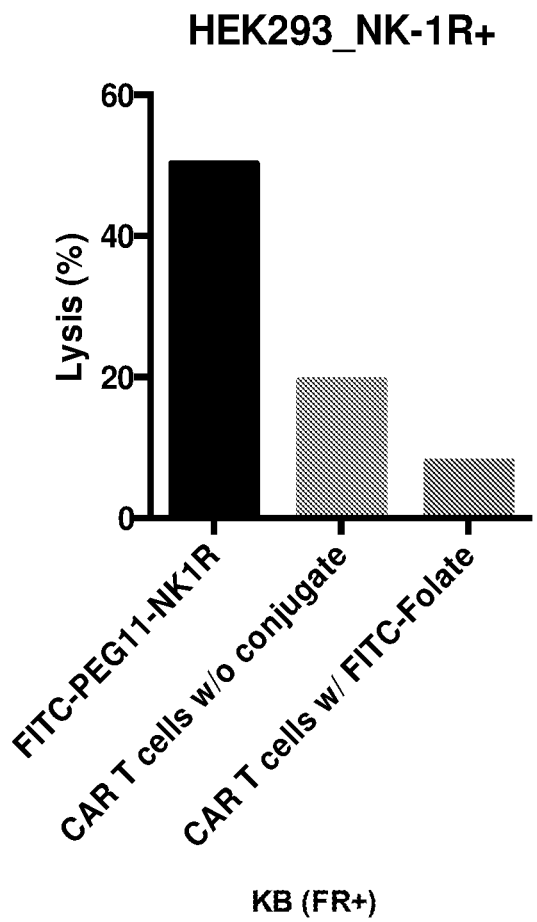
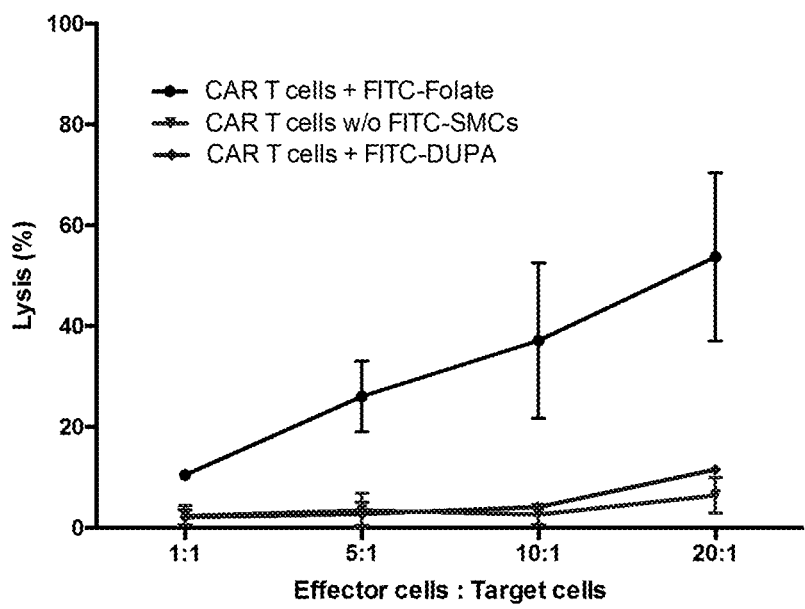
FIGURES 3A-F continued

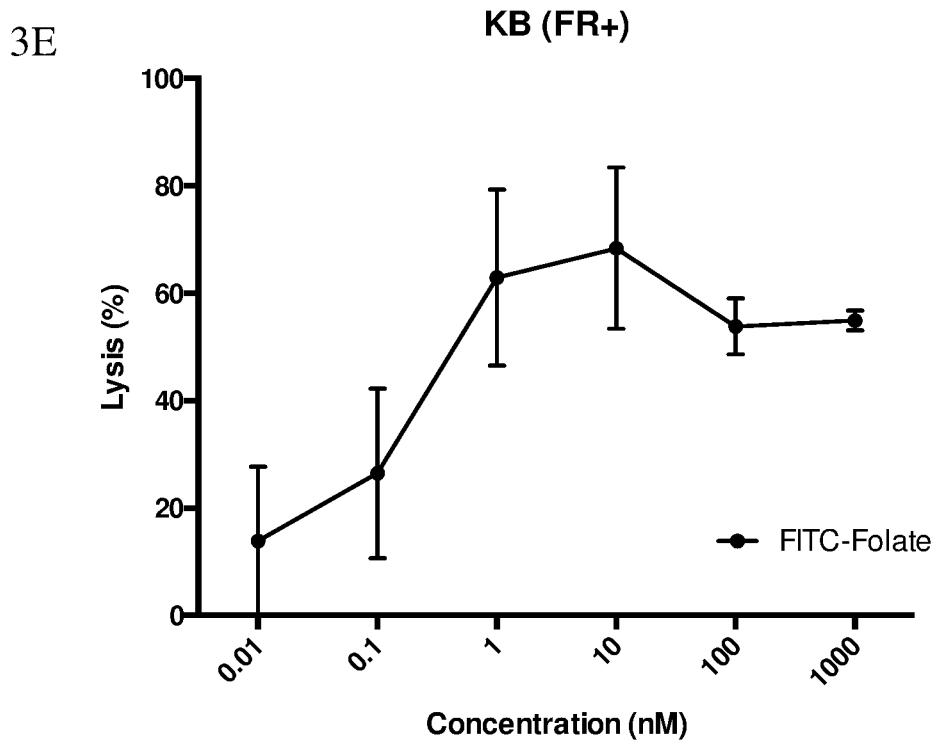
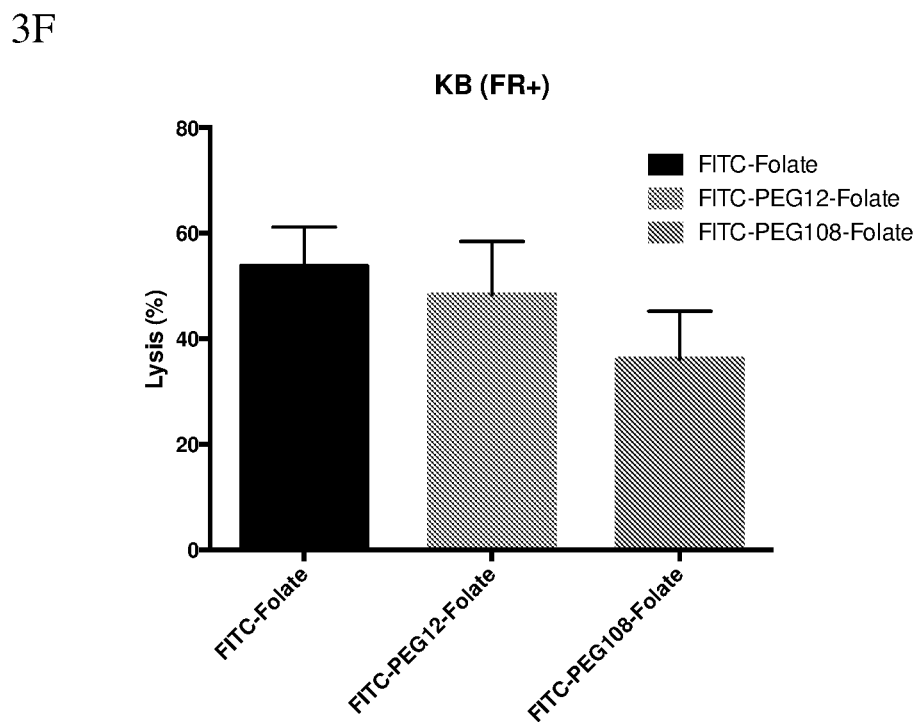
FIGURES 3A-F

4A  Tumor antigen FRα level
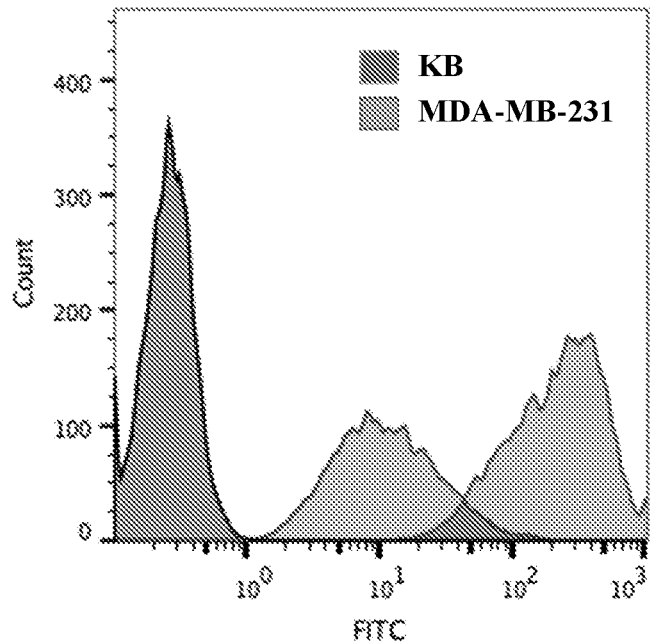
4B  CAR-T cell activation (IFN-γ production):
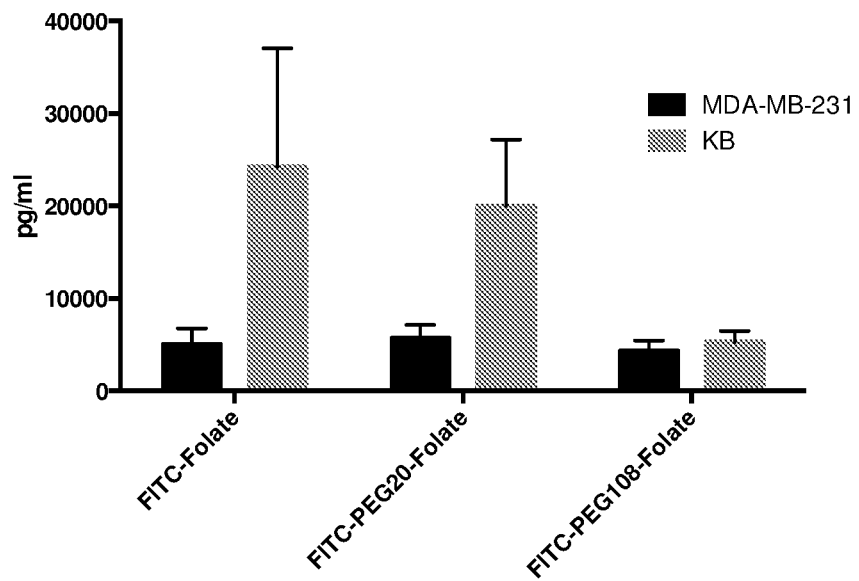
FIGURES 4A-B

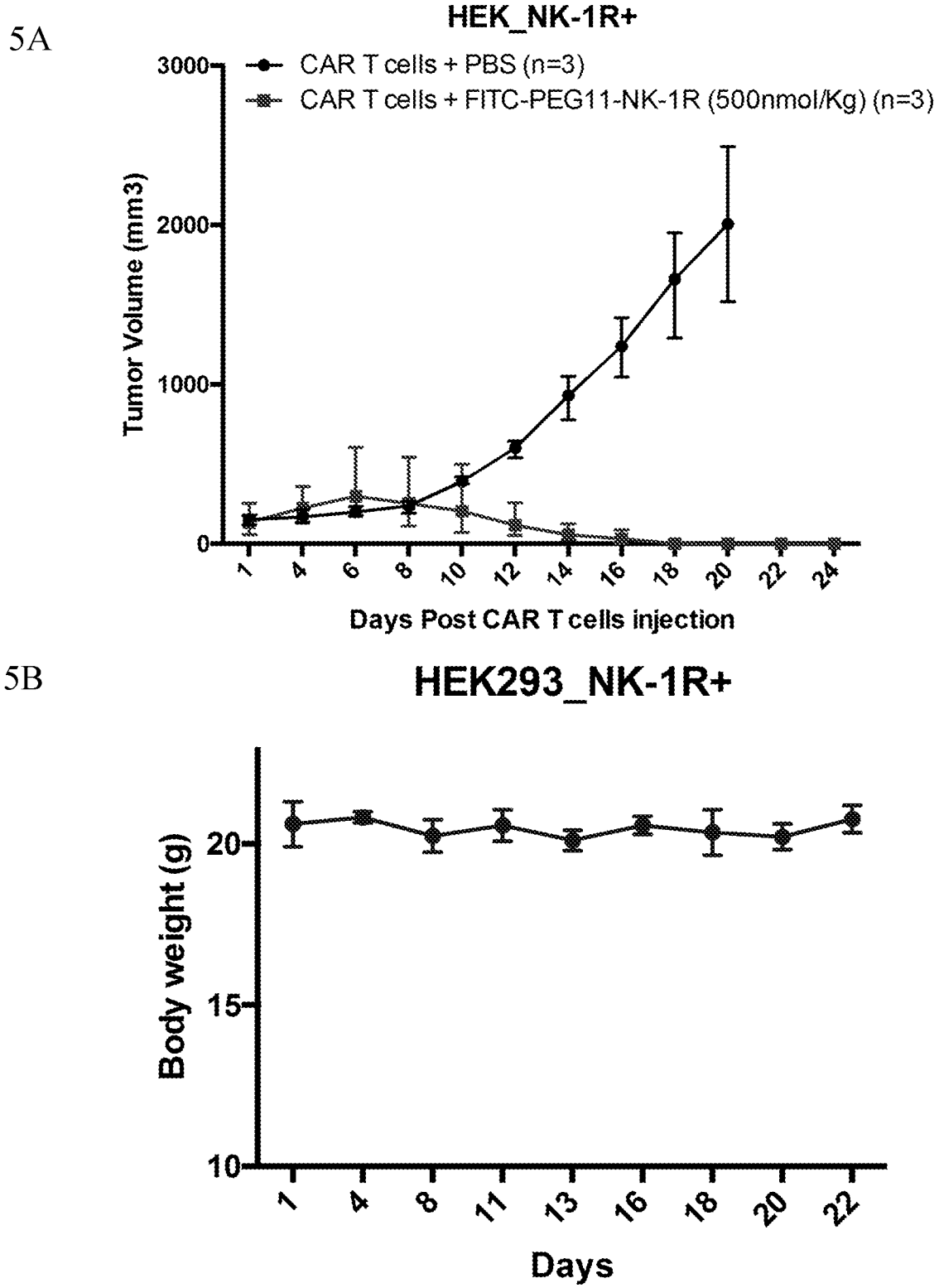
FIGURES 5 A-C continued

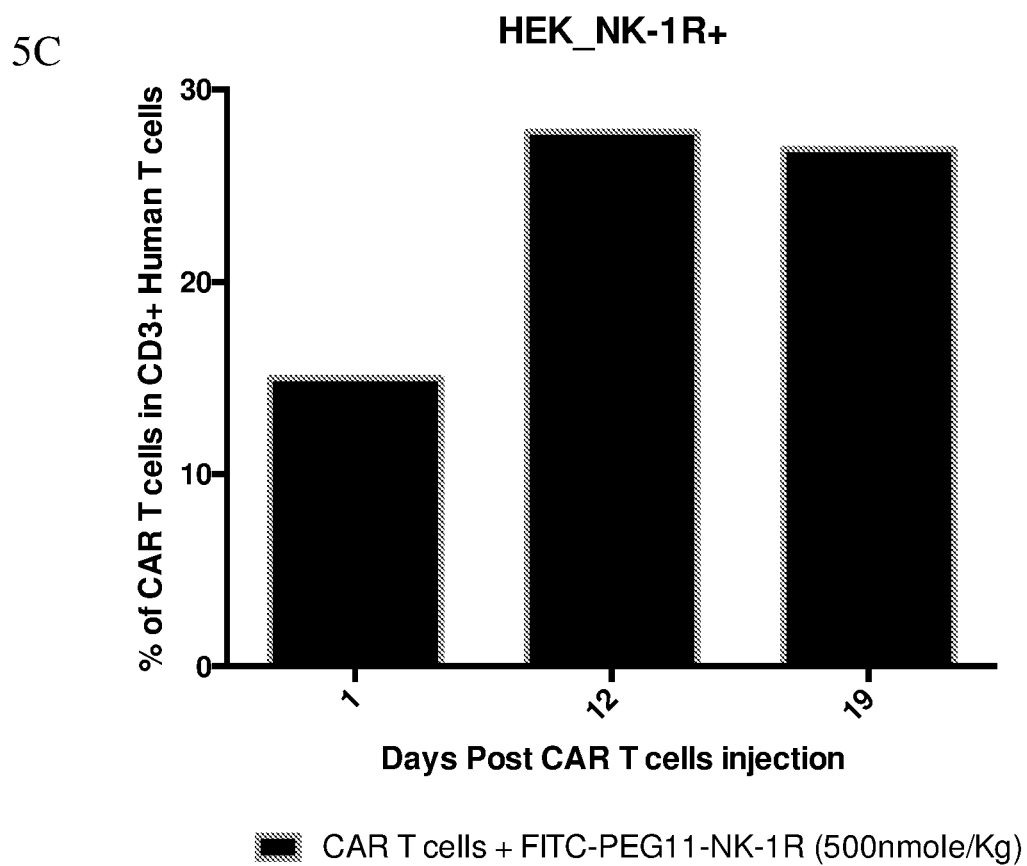
FIGURES 5 A-C

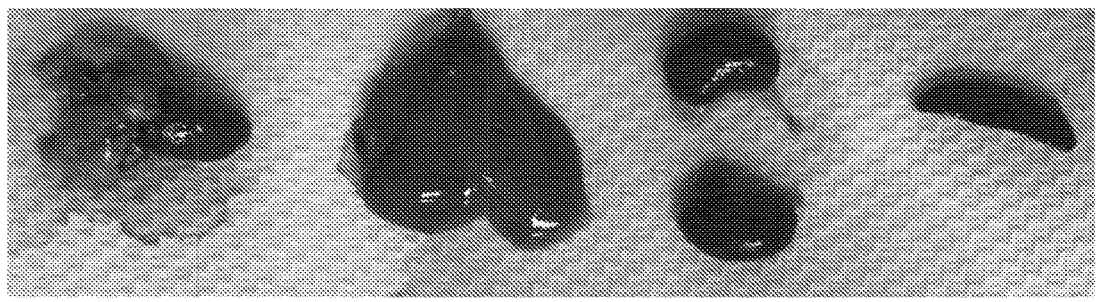
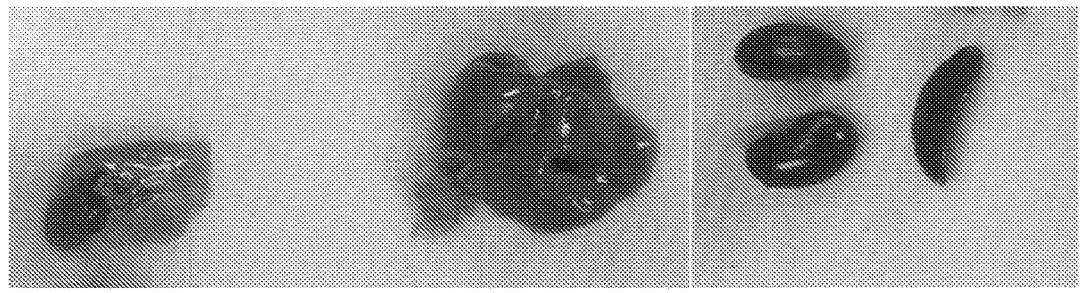
FIGURES 6 A-B

7A
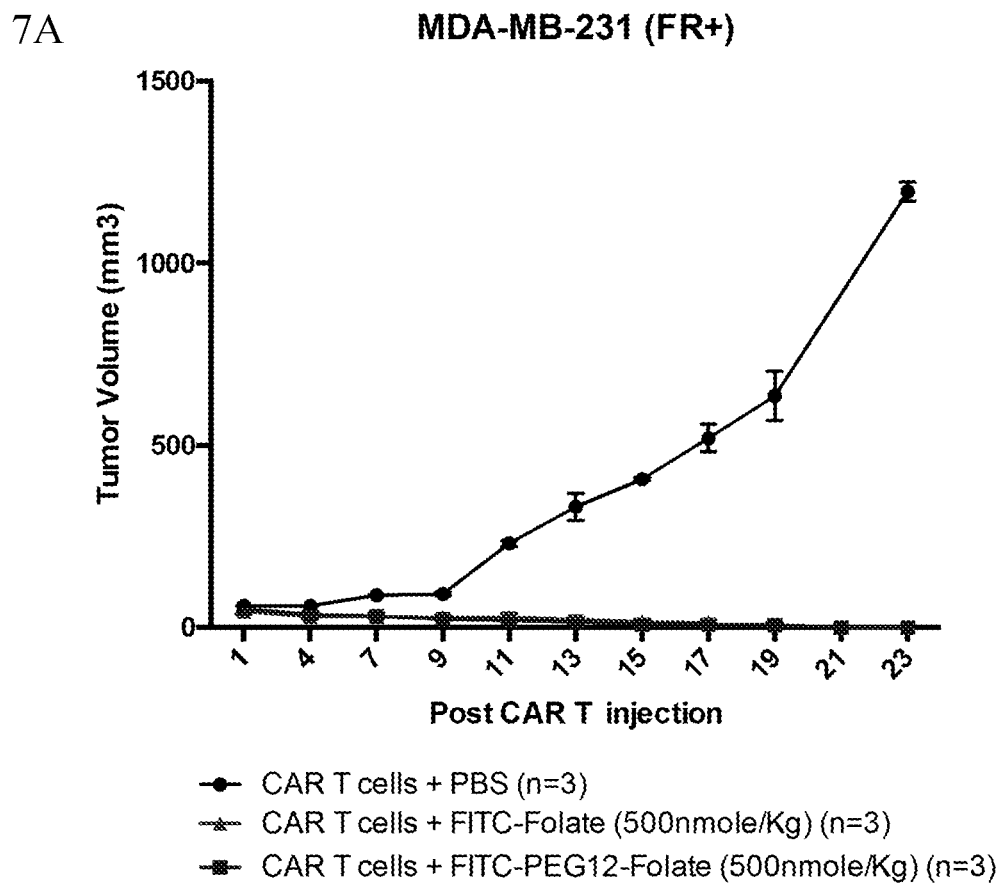
7B
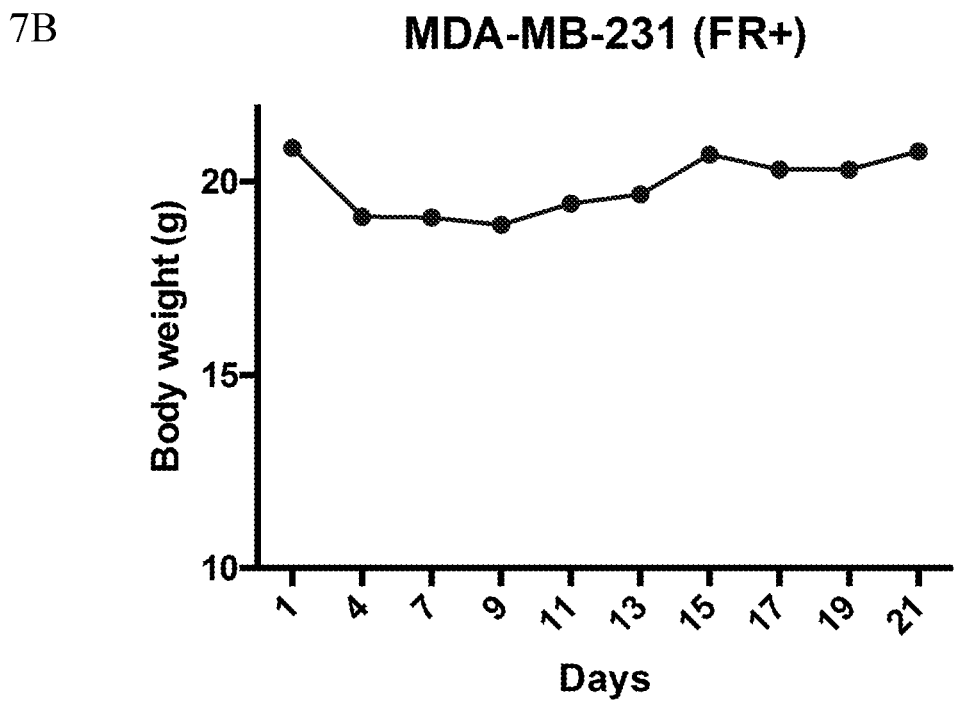
FIGURES 7 A-C continued

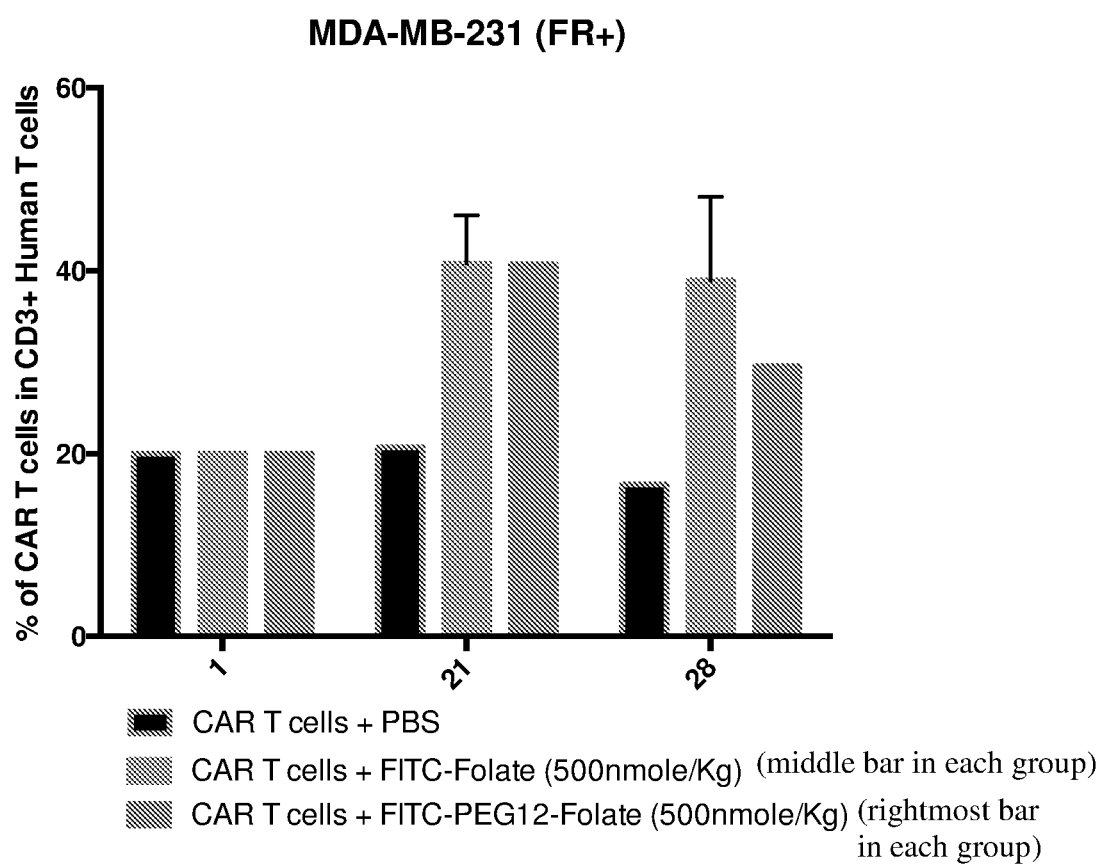
FIGURES 7 A-C

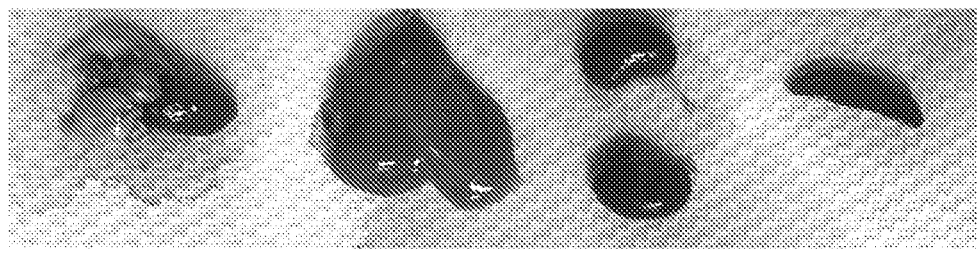
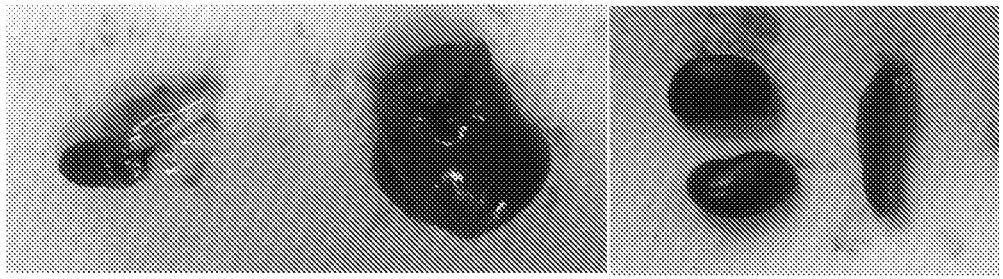
FIGURES 8 A-B

|  | No treatment | HEK-NK1R (NK1R+) (CR) | MDA-MB-231 (FR+) (CR) |
|---|---|---|---|
| WBC ($10^9$/L) | 10.36 | 7.38 | 3.25 |
| Lymphocyte ($10^9$/L) | 0.50 | 1.23 | 0.27 |
| Monocyte ($10^9$/L) | 1.06 | 0.92 | 0.18 |
| Neutrophil ($10^9$/L) | 8.80 | 5.23 | 2.80 |
| Lymphocyte (%) | 4.8 | 16.7 | 8.3 |
| Monocyte (%) | 10.2 | 12.5 | 5.6 |
| Neutrophil (%) | 85.0 | 70.8 | 86.1 |

| FITC-PEG12-Folate dosing | no dosing control | 250 nmoles/kg body weight | 500 nmoles/kg body weight |
|---|---|---|---|
| WBC ($10^9$/L) | 10.36 | 21.07 | 74.17 |
| Lymphocyte ($10^9$/L) | 0.50 | 0.77 | 4.73 |
| Monocyte ($10^9$/L) | 1.06 | 1.19 | 8.96 |
| Neutrophil ($10^9$/L) | 8.80 | 19.11 | 60.48 |

FIGURE 13

14A <Sequence of CAR4-1BBZ>
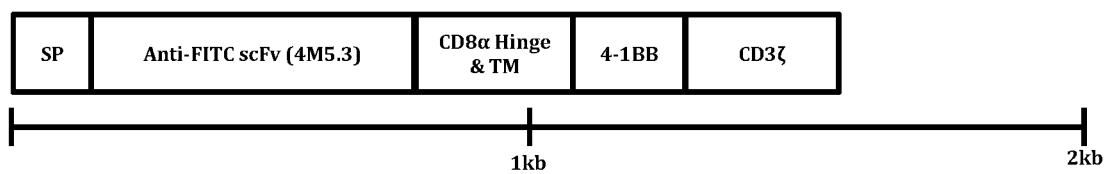
14B
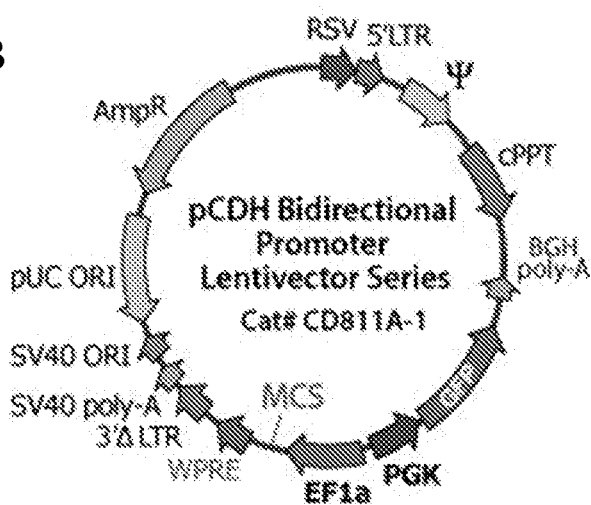
FIGURES 14 A-B

15A 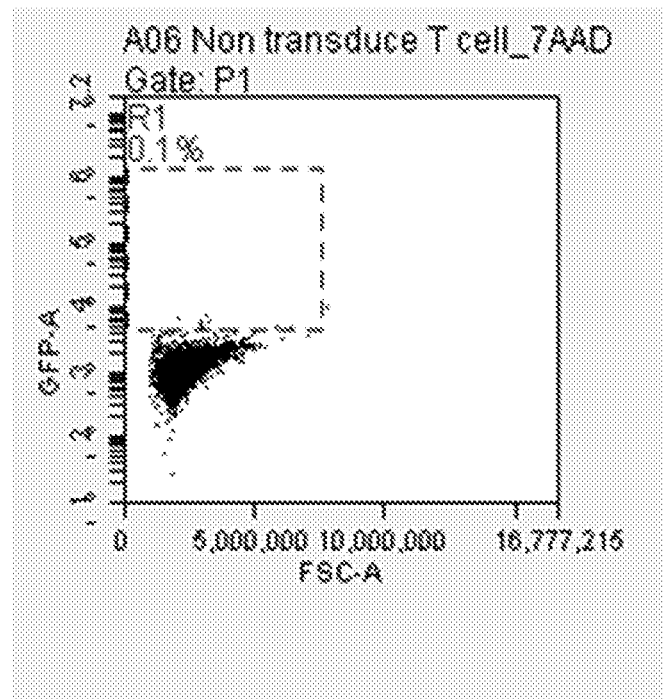
15B 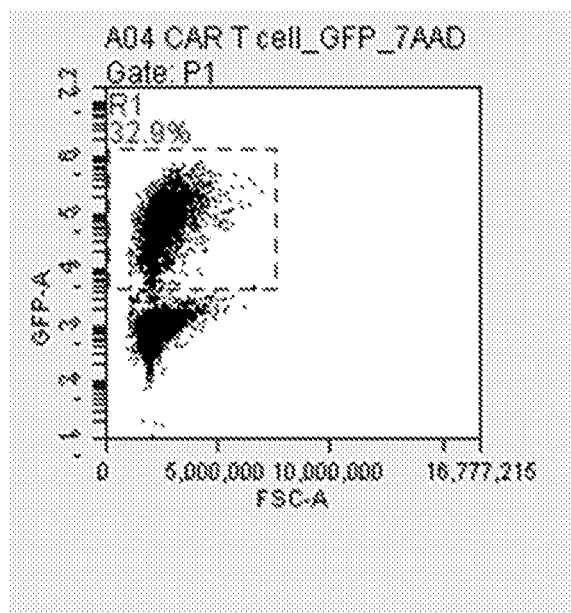
FIGURES 15 A-B

16A
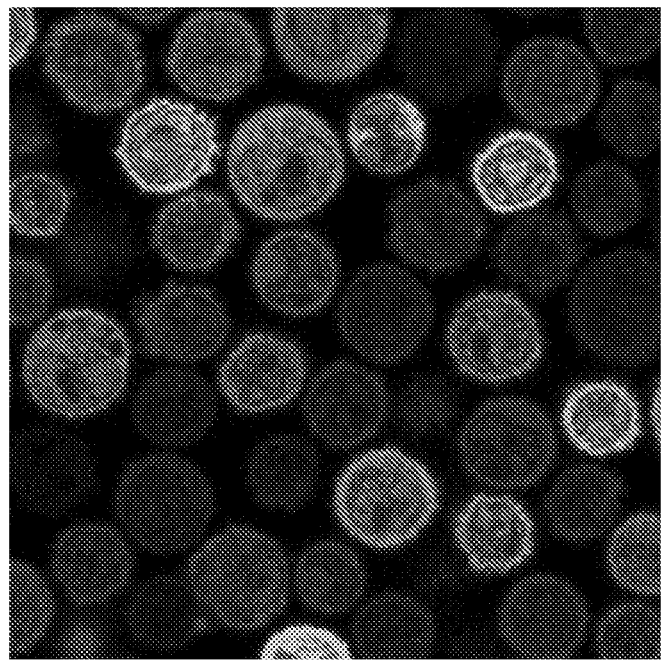
16B
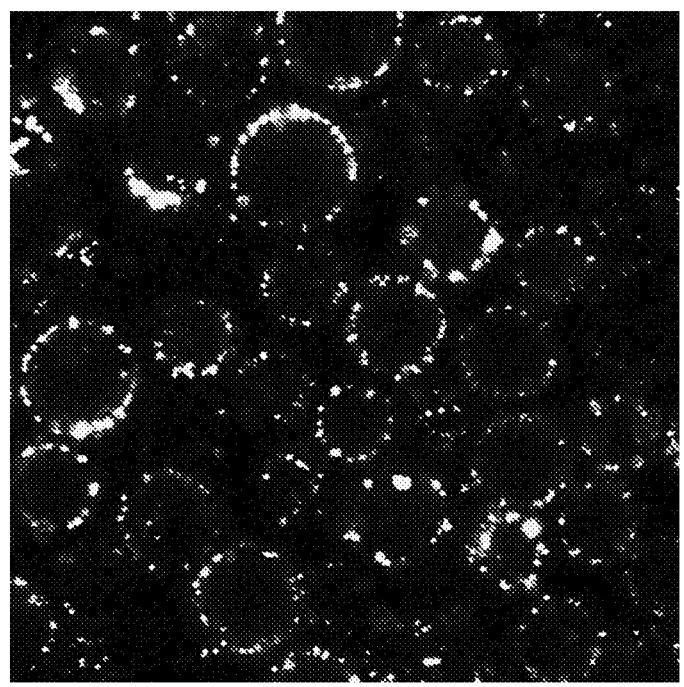
FIGURES 16 A-B

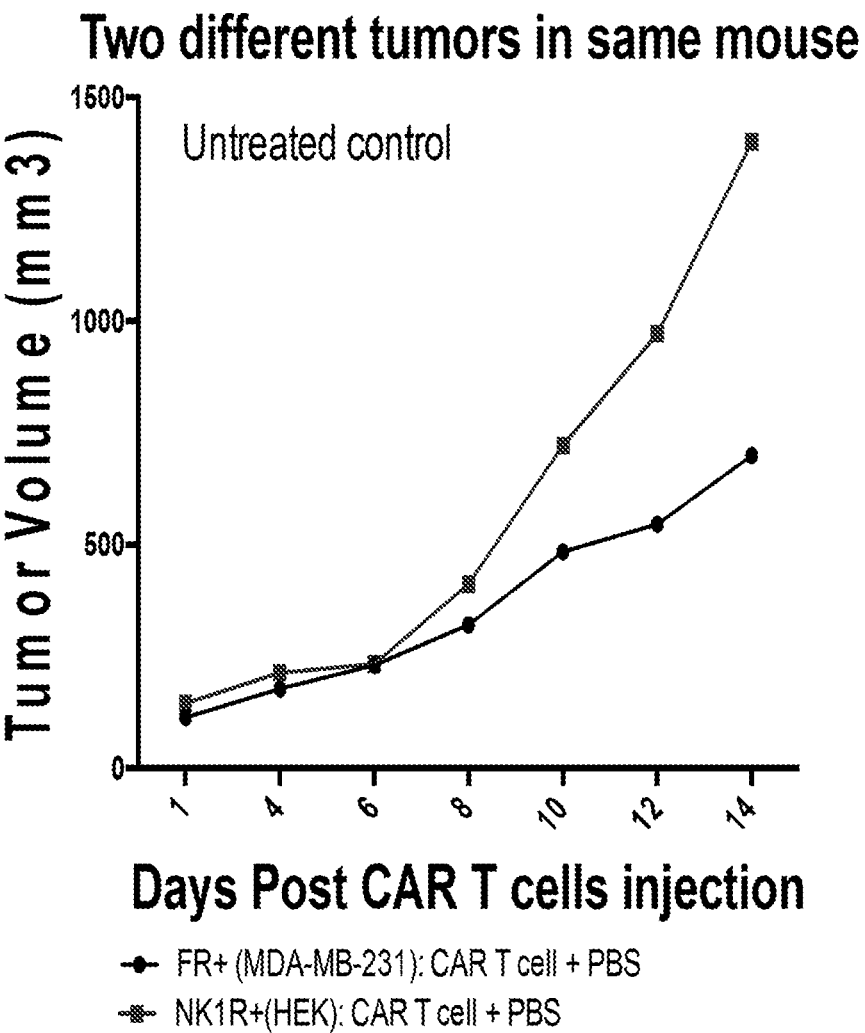
FIGURES 19A-C continued

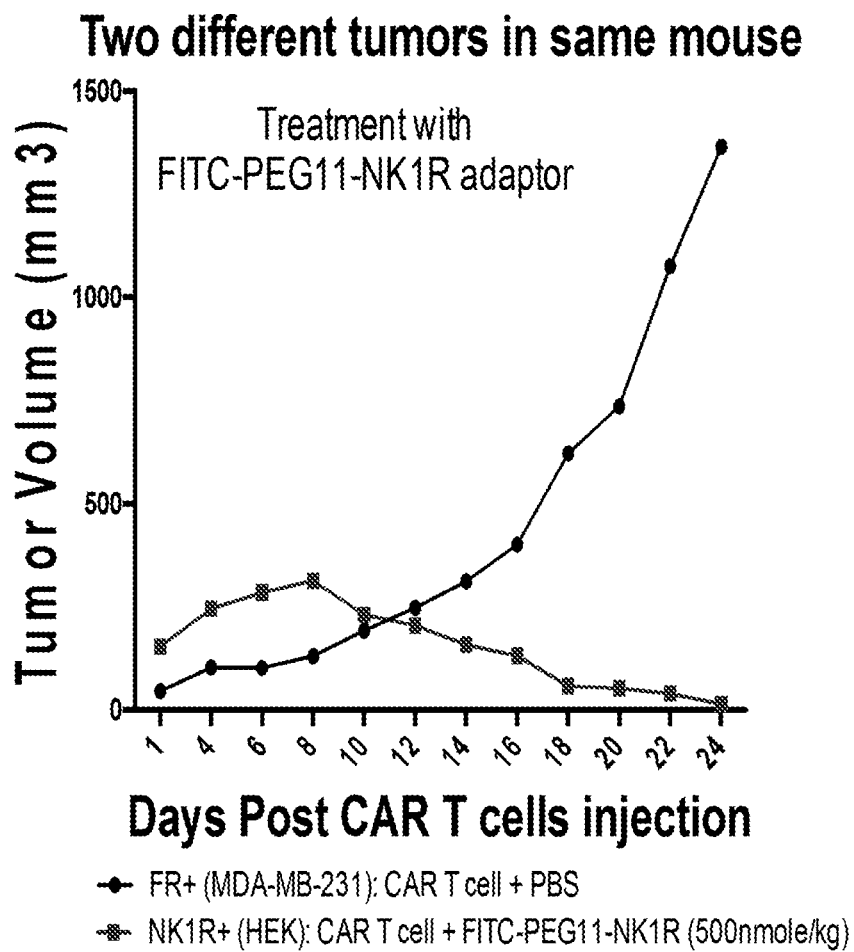
FIGURES 19A-C continued

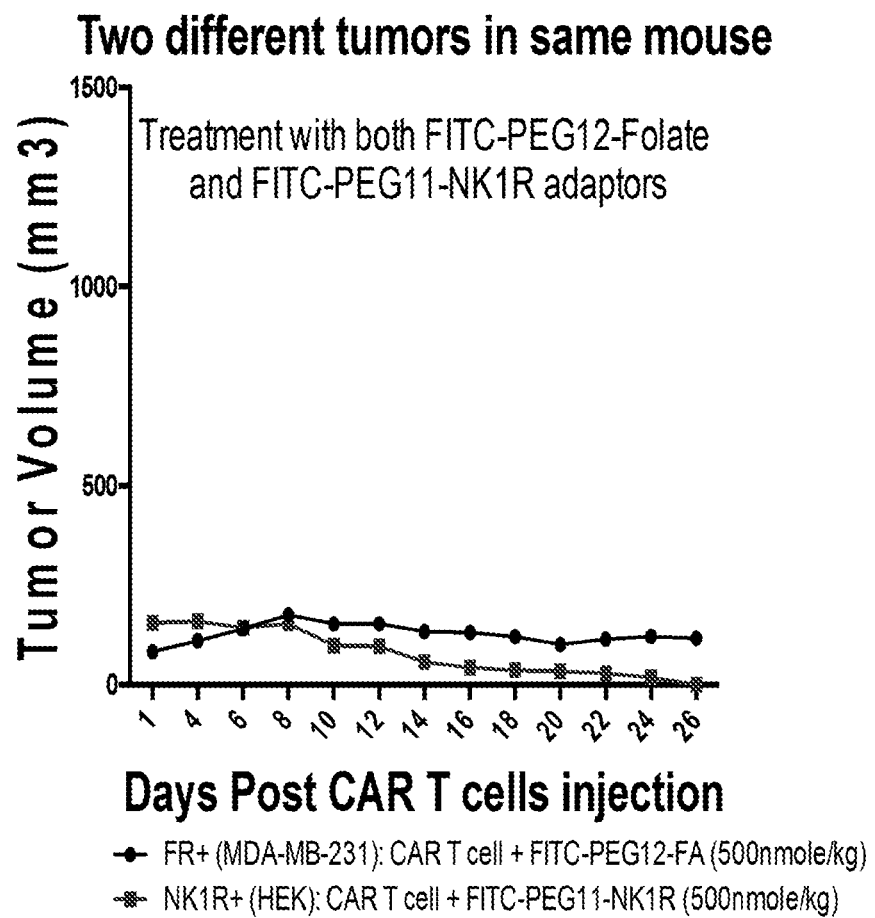
FIGURES 19A-C

SEQUENCE LISTING

```
<160> NUMBER OF SEQ ID NOS: 4

<210> SEQ ID NO 1
<211> LENGTH: 1554
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggccttac cagtgaccgc cttgctcctg ccgctggcct tgctgctcca cgccgccagg      60
ccggatgtcg tgatgaccca gacccccctc agcctcccag tgtccctcgg tgaccaggct     120
tctattagtt gcagatccag ccagtccctc gtgcactcta acgtaatac  ctacctgaga     180 tggtatctcc agaagcccgg acagagccct aaggtgctga tctacaaagt ctccaaccgg     240
gtgtctggag tccctgaccg cttctcaggg agcggttccg gcaccgactt caccctgaag     300
atcaaccggg tggaggccga agacctcggc gtctatttct gctctcagag tacacatgtg     360
ccctggacct tcggcggagg gaccaagctg gagatcaaaa gctccgcaga cgatgccaag     420
aaagatgccg ctaagaaaga cgatgctaag aaagacgatg caaagaaaga cggtggcgtg     480
aagctggatg aaaccggagg aggtctcgtc cagccaggag gagccatgaa gctgagttgc     540
gtgaccagcg gattcacctt tgggcactac tggatgaact gggtgcgaca gtccccagag     600 aagggctcg aatgggtcgc tcagttcagg aacaaaccct acaattatga gacatactat      660
tcagacagcg tgaagggcag gtttactatc agtagagacg attccaaatc tagcgtgtac     720
ctgcagatga acaatctcag ggtcgaagat acaggcatct actattgcac aggggcatcc     780
tatggtatgg agtatctcgg tcaggggaca agcgtcacag tcagtttcgt gccggtcttc     840
ctgccagcga gcccaccac gacgccagcg ccgcgaccac caacaccggc gcccaccatc     900
gcgtcgcagc ccctgtccct gcgcccagag gcgtgccggc cagcggcggg gggcgcagtg     960
cacacgaggg ggctggactt cgcctgtgat atctacatct gggcgccctt ggccgggact    1020
tgtggggtcc ttctcctgtc actggttatc acccttact  gcaaccacag gaaccgtttc    1080
tctgttgtta aacggggcag aaagaaactc ctgtatatat tcaaacaacc atttatgaga    1140
ccagtacaaa ctactcaaga ggaagatggc tgtagctgcc gatttccaga agaagaagaa    1200
ggaggatgtg aactgagagt gaagttcagc aggagcgcag acgcccccgc gtaccagcag    1260
ggccagaacc agctctataa cgagctcaat ctaggacgaa gagaggagta cgatgttttg    1320
gacaagagac gtggccggga ccctgagatg ggggaaagc cgagaaggaa gaaccctcag    1380
gaaggcctgt acaatgaact gcagaaagat aagatggcgg aggcctacag tgagattggg    1440
```

-continued

```
atgaaaggcg agcgccggag gggcaagggg cacgatggcc tttaccaggg tctcagtaca      1500
gccaccaagg acacctacga cgcccttcac atgcaggccc tgccccctcg ctaa            1554
```

<210> SEQ ID NO 2
<211> LENGTH: 517
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Ala Leu Pro Val Thr Ala Leu Leu Pro Leu Ala Leu Leu Leu
1               5                   10                  15

His Ala Ala Arg Pro Asp Val Val Met Thr Gln Thr Pro Leu Ser Leu
                20                  25                  30

Pro Val Ser Leu Gly Asp Gln Ala Ser Ile Ser Cys Arg Ser Ser Gln
            35                  40                  45

Ser Leu Val His Ser Asn Gly Asn Thr Tyr Leu Arg Trp Tyr Leu Gln
        50                  55                  60

Lys Pro Gly Gln Ser Pro Lys Val Leu Ile Tyr Lys Val Ser Asn Arg
65                  70                  75                  80

Val Ser Gly Val Pro Asp Arg Phe Ser Gly Ser Gly Ser Gly Thr Asp
                85                  90                  95

Phe Thr Leu Lys Ile Asn Arg Val Glu Ala Glu Asp Leu Gly Val Tyr
            100                 105                 110

Phe Cys Ser Gln Ser Thr His Val Pro Trp Thr Phe Gly Gly Gly Thr
        115                 120                 125

Lys Leu Glu Ile Lys Ser Ser Ala Asp Asp Ala Lys Lys Asp Ala Ala
    130                 135                 140

Lys Lys Asp Asp Ala Lys Lys Asp Ala Lys Lys Asp Gly Gly Val
145                 150                 155                 160

Lys Leu Asp Glu Thr Gly Gly Gly Leu Val Gln Pro Gly Gly Ala Met
                165                 170                 175

Lys Leu Ser Cys Val Thr Ser Gly Phe Thr Phe Gly His Tyr Trp Met
            180                 185                 190

Asn Trp Val Arg Gln Ser Pro Glu Lys Gly Leu Glu Trp Val Ala Gln
        195                 200                 205

Phe Arg Asn Lys Pro Tyr Asn Tyr Glu Thr Tyr Tyr Ser Asp Ser Val
    210                 215                 220

Lys Gly Arg Phe Thr Ile Ser Arg Asp Asp Ser Lys Ser Ser Val Tyr
225                 230                 235                 240

Leu Gln Met Asn Asn Leu Arg Val Glu Asp Thr Gly Ile Tyr Tyr Cys
                245                 250                 255

Thr Gly Ala Ser Tyr Gly Met Glu Tyr Leu Gly Gln Gly Thr Ser Val
            260                 265                 270

Thr Val Ser Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
                325                 330                 335

Leu Ala Gly Thr Cys Gly Val Leu Leu Leu Ser Leu Val Ile Thr Leu
```

```
                340                 345                 350
Tyr Cys Asn His Arg Asn Arg Phe Ser Val Val Lys Arg Gly Arg Lys
        355                 360                 365
Lys Leu Leu Tyr Ile Phe Lys Gln Pro Phe Met Arg Pro Val Gln Thr
    370                 375                 380
Thr Gln Glu Glu Asp Gly Cys Ser Cys Arg Phe Pro Glu Glu Glu Glu
385                 390                 395                 400
Gly Gly Cys Glu Leu Arg Val Lys Phe Ser Arg Ser Ala Asp Ala Pro
                405                 410                 415
Ala Tyr Gln Gln Gly Gln Asn Gln Leu Tyr Asn Glu Leu Asn Leu Gly
            420                 425                 430
Arg Arg Glu Glu Tyr Asp Val Leu Asp Lys Arg Arg Gly Arg Asp Pro
        435                 440                 445
Glu Met Gly Gly Lys Pro Arg Arg Lys Asn Pro Gln Glu Gly Leu Tyr
    450                 455                 460
Asn Glu Leu Gln Lys Asp Lys Met Ala Glu Ala Tyr Ser Glu Ile Gly
465                 470                 475                 480
Met Lys Gly Glu Arg Arg Arg Gly Lys Gly His Asp Gly Leu Tyr Gln
                485                 490                 495
Gly Leu Ser Thr Ala Thr Lys Asp Thr Tyr Asp Ala Leu His Met Gln
            500                 505                 510
Ala Leu Pro Pro Arg
        515

<210> SEQ ID NO 3
<211> LENGTH: 1560
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gccaccatgg ccttaccagt gaccgccttg ctcctgccgc tggccttgct gctccacgcc      60
gccaggccgg atgtcgtgat gacccagacc cccctcagcc tcccagtgtc cctcggtgac     120
caggcttcta ttagttgcag atccagccag tccctcgtgc actctaacgg taatacctac     180
ctgagatggt atctccagaa gcccggacag agccctaagg tgctgatcta caaagtctcc     240
aaccgggtgt ctggagtccc tgaccgcttc tcagggagcg gttccggcac cgacttcacc     300
ctgaagatca accgggtgga ggccgaagac ctcggcgtct atttctgctc tcagagtaca     360
catgtgccct ggaccttcgg cggagggacc aagctggaga tcaaaagctc cgcagacgat     420
gccaagaaag atgccgctaa gaaagacgat gctaagaaag acgatgcaaa gaaagacggt     480
ggcgtgaagc tggatgaaac cggaggaggt ctcgtccagc aggaggagc catgaagctg     540 agttgcgtga ccagcggatt caccttcgg cactactgga tgaactgggt gcgacagtcc     600
ccagagaagg ggctcgaatg ggtcgctcag ttcaggaaca aaccctacaa ttatgagaca     660
tactattcag acagcgtgaa gggcaggttt actatcagta gagacgattc aaatctagc     720 gtgtacctgc agatgaacaa tctcagggtc gaagatacag gcatctacta ttgcacaggg     780
gcatcctatg gtatggagta tctcggtcag gggacaagcg tcacagtcag tttcgtgccg     840
gtcttcctgc cagcgaagcc caccacgacg ccagcgccgc gaccaccaac accggcgccc     900
```

-continued

```
accatcgcgt cgcagcccct gtccctgcgc ccagaggcgt gccggccagc ggcgggggc    960 gcagtgcaca cgagggggct ggacttcgcc tgtgatatct acatctgggc gcccttggcc   1020
gggacttgtg gggtccttct cctgtcactg gttatcaccc tttactgcaa ccacaggaac   1080
cgtttctctg ttgttaaacg gggcagaaag aaactcctgt atatattcaa acaaccattt   1140
atgagaccag tacaaactac tcaagaggaa gatggctgta gctgccgatt ccagaagaa    1200 gaagaaggag gatgtgaact gagagtgaag ttcagcagga gcgcagacgc ccccgcgtac   1260
cagcagggcc agaaccagct ctataacgag ctcaatctag gacgaagaga ggagtacgat   1320
gttttggaca gagacgtgg ccgggaccct gagatggggg gaaagccgag aaggaagaac    1380
cctcaggaag gcctgtacaa tgaactgcag aaagataaga tggcggaggc ctacagtgag   1440
attgggatga aggcgagcg ccggagggc aaggggcacg atggccttta ccagggtctc     1500
agtacagcca ccaaggacac ctacgacgcc cttcacatgc aggccctgcc ccctcgctaa   1560
```

<210> SEQ ID NO 4
<211> LENGTH: 519
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Ala Thr Met Ala Leu Pro Val Thr Ala Leu Leu Leu Pro Leu Ala Leu
1               5                   10                  15

Leu Leu His Ala Ala Arg Pro Asp Val Val Met Thr Gln Thr Pro Leu
                20                  25                  30

Ser Leu Pro Val Ser Leu Gly Asp Gln Ala Ser Ile Ser Cys Arg Ser
            35                  40                  45

Ser Gln Ser Leu Val His Ser Asn Gly Asn Thr Tyr Leu Arg Trp Tyr
        50                  55                  60

Leu Gln Lys Pro Gly Gln Ser Pro Lys Val Leu Ile Tyr Lys Val Ser
65                  70                  75                  80

Asn Arg Val Ser Gly Val Pro Asp Arg Phe Ser Gly Ser Gly Ser Gly
                85                  90                  95

Thr Asp Phe Thr Leu Lys Ile Asn Arg Val Glu Ala Glu Asp Leu Gly
            100                 105                 110

Val Tyr Phe Cys Ser Gln Ser Thr His Val Pro Trp Thr Phe Gly Gly
        115                 120                 125

Gly Thr Lys Leu Glu Ile Lys Ser Ser Ala Asp Asp Ala Lys Lys Asp
    130                 135                 140

Ala Ala Lys Lys Asp Asp Ala Lys Lys Asp Ala Lys Lys Asp Gly
145                 150                 155                 160

Gly Val Lys Leu Asp Glu Thr Gly Gly Gly Leu Val Gln Pro Gly Gly
                165                 170                 175

Ala Met Lys Leu Ser Cys Val Thr Ser Gly Phe Thr Phe Gly His Tyr
            180                 185                 190
```

```
Trp Met Asn Trp Val Arg Gln Ser Pro Glu Lys Gly Leu Glu Trp Val
        195                 200                 205

Ala Gln Phe Arg Asn Lys Pro Tyr Asn Tyr Glu Thr Tyr Tyr Ser Asp
    210                 215                 220

Ser Val Lys Gly Arg Phe Thr Ile Ser Arg Asp Asp Ser Lys Ser Ser
225                 230                 235                 240

Val Tyr Leu Gln Met Asn Asn Leu Arg Val Glu Asp Thr Gly Ile Tyr
            245                 250                 255

Tyr Cys Thr Gly Ala Ser Tyr Gly Met Glu Tyr Leu Gly Gln Gly Thr
        260                 265                 270

Ser Val Thr Val Ser Phe Val Pro Val Phe Leu Pro Ala Lys Pro Thr
    275                 280                 285

Thr Thr Pro Ala Pro Arg Pro Pro Thr Pro Ala Pro Thr Ile Ala Ser
290                 295                 300

Gln Pro Leu Ser Leu Arg Pro Glu Ala Cys Arg Pro Ala Ala Gly Gly
305                 310                 315                 320

Ala Val His Thr Arg Gly Leu Asp Phe Ala Cys Asp Ile Tyr Ile Trp
            325                 330                 335

Ala Pro Leu Ala Gly Thr Cys Gly Val Leu Leu Leu Ser Leu Val Ile
        340                 345                 350

Thr Leu Tyr Cys Asn His Arg Asn Arg Phe Ser Val Val Lys Arg Gly
    355                 360                 365

Arg Lys Lys Leu Leu Tyr Ile Phe Lys Gln Pro Phe Met Arg Pro Val
370                 375                 380

Gln Thr Thr Gln Glu Glu Asp Gly Cys Ser Cys Arg Phe Pro Glu Glu
385                 390                 395                 400

Glu Glu Gly Gly Cys Glu Leu Arg Val Lys Phe Ser Arg Ser Ala Asp
            405                 410                 415

Ala Pro Ala Tyr Gln Gln Gly Gln Asn Gln Leu Tyr Asn Glu Leu Asn
        420                 425                 430

Leu Gly Arg Arg Glu Glu Tyr Asp Val Leu Asp Lys Arg Arg Gly Arg
    435                 440                 445

Asp Pro Glu Met Gly Gly Lys Pro Arg Arg Lys Asn Pro Gln Glu Gly
450                 455                 460

Leu Tyr Asn Glu Leu Gln Lys Asp Lys Met Ala Glu Ala Tyr Ser Glu
465                 470                 475                 480

Ile Gly Met Lys Gly Glu Arg Arg Arg Gly Lys Gly His Asp Gly Leu
            485                 490                 495

Tyr Gln Gly Leu Ser Thr Ala Thr Lys Asp Thr Tyr Asp Ala Leu His
        500                 505                 510

Met Gln Ala Leu Pro Pro Arg
    515
```

METHODS AND COMPOSITIONS FOR CAR T CELL THERAPY

CROSS REFERENCE TO RELATED APPLICATIONS

This application is a U.S. national stage application under 35 U.S.C. § 371(b) of International Application No. PCT/US2017/026618 filed Apr. 7, 2017, which claims priority under 35 U.S.C. § 119(e) to U.S. Provisional Application Ser. No. 62/320,183, filed Apr. 8, 2016 and U.S. Provisional Application Ser. No. 62/323,971, filed Apr. 18, 2016, all of which are incorporated herein by reference in their entirety.

TECHNICAL FIELD

The present disclosure relates to methods of treating a patient with a cancer by administering to the patient a composition comprising CAR T cells and administering to the patient a small molecule linked to a targeting moiety by a linker. The disclosure also relates to compositions for use in such methods.

BACKGROUND

Immunotherapy based on adoptive transfer of lymphocytes (e.g., T cells) into a patient is a valuable therapy in the treatment of cancer and other diseases. Many important advancements have been made in the development of immunotherapies based on adoptive transfer of lymphocytes. Among the many different types of immunotherapeutic agents, one of the most promising of the immunotherapeutic agents being developed is T cells expressing chimeric antigen receptors (CAR T cells). The chimeric antigen receptor (CAR) is a genetically engineered receptor that is designed to target a specific antigen, for example, a tumor antigen. This targeting can result in cytotoxicity against the tumor, for example, such that CAR T cells expressing CARs can target and kill tumors via the specific tumor antigens.

First generation CARs are composed of a recognition region, e.g., a single chain fragment variable (scFv) region derived from an antibody for recognition and binding to the antigen expressed by the tumor, and an activation signaling domain, e.g., the CD3ζ chain of T cells can serve as a T cell activation signal in CARs. Although CAR T cells have shown positive results in vitro, they have had limited success in eliminating disease (e.g., cancer) in clinical trials. One problem has been the inability to prolong activation and expand the CAR T cell population in vivo.

To address this problem, a co-stimulation domain (e.g. CD137, CD28 or CD134) has been included in second generation CARs to achieve prolonged activation of T cells in vivo. Addition of a co-stimulation domain enhances the in vivo proliferation and survival of T cells containing CARs, and initial clinical data have shown that such constructs are promising therapeutic agents in the treatment of diseases, such as cancer.

Although improvements have been made in CAR T cell therapies, several problems remain. First, 'off-target' toxicity may occur due to normal cells that express the antigen targeted by the CAR T cells (e.g., a tumor-associated antigen). Second, unregulated CAR T cell activation may be found where the rapid and uncontrolled elimination of diseased cells (e.g., cancer cells) by CAR T cells induces a constellation of metabolic disturbances, called tumor lysis syndrome, in the case where a tumor is being treated, or cytokine release syndrome (CRS), which can be fatal to patients. Tumor lysis syndrome and CRS can result due to administered CAR T cells that cannot be easily regulated, and are activated uncontrollably. Accordingly, although CAR T cells show great promise as a tool in the treatment of diseases, such as cancer, additional CAR T cell therapies are needed that provide reduced off-target toxicity, and more precise control of CAR T cell activation.

SUMMARY OF THE INVENTION

The present inventors have discovered methods of reducing off-target toxicity, and more precisely controlling CAR T cell activation, providing important advancements in CAR T cell therapy. In the various embodiments described herein, a small molecule ligand linked to a targeting moiety by a linker is used as a bridge between the cancer and the CAR T cells directing the CAR T cells to the cancer for amelioration of the cancer. In one embodiment, the "small molecule ligand" can be, for example, a folate, DUPA, an NK-1R ligand, a CAIX ligand, a ligand of gamma glutamyl transpeptidase, or a CCK2R ligand, each of which is a small molecule ligand that binds specifically to cancer cells (i.e., the receptor for these ligands is overexpressed on cancers compared to normal tissues).

In one embodiment, the "small molecule ligand" is linked to a "targeting moiety" that binds to the CAR expressed by CAR T cells. In various embodiments, the "targeting moiety" can be selected, for example, from 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester (PFP), tetrafluorophenyl ester (TFP), a knottin, a centyrin, and a DARPin.

The "targeting moiety" binds to the recognition region of the genetically engineered CAR expressed by CAR T cells. Accordingly, the recognition region of the CAR (e.g., a single chain fragment variable region (scFv) of an antibody) is directed to the "targeted moiety." Thus, the small molecule ligand linked to a targeting moiety by a linker acts as a 'bridge' between the cancer and the CAR T cells directing the CAR T cells to the cancer for amelioration of the cancer.

In one illustrative embodiment, the inventors have discovered that varying the dose of the small molecule ligand linked to a targeting moiety by a linker (i.e., the bridge), can result in the ability to control CRS in vivo. In another embodiment, the inventors have discovered that varying the linker in the small molecule ligand linked to a targeting moiety (the bridge) can control CRS in vivo upon CAR T cell activation. In yet another embodiment, combinations of these methods can be used for precise control of CAR T cell activation and cytokine release in vivo. In another embodiment, affinity of the small molecule ligand for its receptor on the cancer can be altered to control CAR T cell activation, or to achieve specificity for the cancer avoiding toxicity towards normal tissues.

In one embodiment, a method of treatment of a cancer is provided. The method comprises i) administering to a patient a first dose of a compound, or a pharmaceutically acceptable salt thereof, wherein the compound comprises a small molecule ligand linked to a targeting moiety by a linker, ii) administering to the patient a CAR T cell composition wherein the CAR T cell comprises a CAR directed to the targeting moiety, ii) administering to the patient a second dose of the compound, or the pharmaceutically acceptable salt thereof, wherein the second dose is different than the first dose, and treating the patient to ameliorate the cancer.

In another embodiment, a method of treatment of a cancer is provided. The method comprises i) administering to the patient a first conjugate, or a pharmaceutically acceptable salt thereof, ii) administering to the patient a CAR T cell composition wherein the CAR T cell comprises a CAR directed to the targeting moiety, iii) administering to the patient a second conjugate, or a pharmaceutically acceptable salt thereof, wherein the first and the second conjugate each comprise a small molecule ligand linked to a targeting moiety by a linker and wherein the first conjugate and the second conjugate are different, and iv) treating the patient to ameliorate the cancer.

In yet another embodiment, a method of treatment of a cancer is provided. The method comprises i) administering to a patient a first dose of a first conjugate, or a pharmaceutically acceptable salt thereof, ii) administering to the patient a CAR T cell composition wherein the CAR T cell comprises a CAR directed to the targeting moiety, ii) administering to the patient a second dose of a second conjugate, or a pharmaceutically acceptable salt thereof, wherein the first conjugate and the second conjugate each comprise a small molecule ligand linked to a targeting moiety, wherein the first conjugate and the second conjugate are different, and wherein the first dose and the second dose are different, and iv) treating the patient to ameliorate the cancer.

In yet another illustrative embodiment, a CAR T cell comprising a nucleic acid comprising SEQ ID NO:1 is provided. In another aspect, a CAR T cell comprising a polypeptide comprising SEQ ID NO:2 is provided. In another embodiment, an isolated nucleic acid comprising SEQ ID NO:1 and encoding a chimeric antigen receptor is provided. In still another embodiment, a chimeric antigen receptor polypeptide comprising SEQ ID NO:2 is provided. In another aspect, a vector comprising SEQ ID NO:1 is provided. In another illustrative embodiment, a vector is provided comprising SEQ ID NO:1 wherein the vector is a lentiviral vector.

Several embodiments are also described by the following enumerated clauses:

1. A method of treatment of a cancer, the method comprising
   i) administering to a patient a first dose of a compound, or a pharmaceutically acceptable salt thereof, wherein the compound comprises a small molecule ligand linked to a targeting moiety by a linker;
   ii) administering to the patient a CAR T cell composition wherein the CAR T cell comprises a CAR directed to the targeting moiety;
   ii) administering to the patient a second dose of the compound, or the pharmaceutically acceptable salt thereof, wherein the second dose is different than the first dose; and
   iv) treating the patient to ameliorate the cancer.
2. A method of treatment of a cancer, the method comprising
   i) administering to the patient a first conjugate, or a pharmaceutically acceptable salt thereof;
   ii) administering to the patient a CAR T cell composition wherein the CAR T cell comprises a CAR directed to the targeting moiety;
   iii) administering to the patient a second conjugate, or a pharmaceutically acceptable salt thereof,
   wherein the first and the second conjugate each comprise a small molecule ligand linked to a targeting moiety by a linker and wherein the first conjugate and the second conjugate are different; and
   iv) treating the patient to ameliorate the cancer.
3. A method of treatment of a cancer, the method comprising
   i) administering to a patient a first dose of a first conjugate, or a pharmaceutically acceptable salt thereof;
   ii) administering to the patient a CAR T cell composition wherein the CAR T cell comprises a CAR directed to the targeting moiety;
   ii) administering to the patient a second dose of a second conjugate, or a pharmaceutically acceptable salt thereof,
   wherein the first conjugate and the second conjugate each comprise a small molecule ligand linked to a targeting moiety, wherein the first conjugate and the second conjugate are different, and wherein the first dose and the second dose are different; and
   iv) treating the patient to ameliorate the cancer.
4. The method of clause 2 or 3 wherein the linker in the first conjugate, or the pharmaceutically acceptable salt thereof, and the linker in the second conjugate, or the pharmaceutically acceptable salt thereof, are different.
5. The method of clause 2 or 3 wherein the linker in the first conjugate, or the pharmaceutically acceptable salt thereof, and the linker in the second conjugate, or the pharmaceutically acceptable salt thereof, are the same.
6. The method of any one of clauses 2 to 5 wherein the ligand in the first conjugate, or the pharmaceutically acceptable salt thereof, and the ligand in the second conjugate, or the pharmaceutically acceptable salt thereof, are different.
7. The method of any one of clauses 2 to 5 wherein the ligand in the first conjugate, or the pharmaceutically acceptable salt thereof, and the ligand in the second conjugate, or the pharmaceutically acceptable salt thereof, are the same.
8. The method of any one of clauses 2 to 7 wherein the targeting moiety in the first conjugate, or the pharmaceutically acceptable salt thereof, and the targeting moiety in the second conjugate, or the pharmaceutically acceptable salt thereof, are different.
9. The method of any one of clauses 2 to 7 wherein the targeting moiety in the first conjugate, or the pharmaceutically acceptable salt thereof, and the targeting moiety in the second conjugate, or the pharmaceutically acceptable salt thereof, are the same.
10. The method of any one of clauses 1 to 9 wherein the ligand is selected from a folate, DUPA, an NK-1R ligand, a CAIX ligand, a ligand of gamma glutamyl transpeptidase, and a CCK2R ligand.
11. The method of clause 10 wherein the ligand is a folate.
12. The method of clause 10 wherein the ligand is an NK-1R ligand.
13. The method of clause 10 wherein the ligand is DUPA.
14. The method of clause 10 wherein the ligand is a CCK2R ligand.
15. The method of clause 10 wherein the ligand is a ligand of gamma glutamyl transpeptidase.
16. The method of any one of clauses 1 to 15 wherein the targeting moiety is selected from 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester (PFP), tetrafluorophenyl ester (TFP), a knottin, a centyrin, and a DARPin.
17. The method of clause 16 wherein the targeting moiety is FITC.
18. The method of clause 16 wherein the targeting moiety is DNP.
19. The method of clause 16 wherein the targeting moiety is TNP.
20. The method of any one of clauses 1 to 19 wherein the linker comprises polyethylene glycol (PEG), polyproline, a hydrophilic amino acid, a sugar, an unnatural peptidoglycan, a polyvinylpyrrolidone, and/or pluronic F-127.
21. The method of clause 20 wherein the linker comprises PEG.
22. The method of any one of clauses 1 to 21 wherein the compound, or the pharmaceutically acceptable salt thereof, the first conjugate, or the pharmaceutically acceptable salt thereof, or the second conjugate or the pharmaceutically acceptable salt thereof, has the formula

B-L-T, wherein B represents the small molecule ligand, L represents the linker, and T represents the targeting moiety, and wherein L comprises a structure having the formula

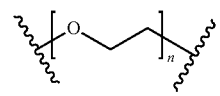

wherein n is an integer from 0 to 200.
23. The method of clause 22 wherein n is an integer from 0 to 150.
24. The method of clause 22 wherein n is an integer from 0 to 110.
25. The method of clause 22 wherein n is an integer from 0 to 20.
26. The method of clause 22 wherein n is an integer from 15 to 20.
27. The method of clause 22 wherein n is an integer from 15 to 110.
28. The method of any one of clauses 1 to 27 wherein the linker comprises PEG and the targeting moiety is FITC, or a pharmaceutically acceptable salt thereof.
29. The method of any one of clauses 1 to 28 wherein the dose of the compound, or the pharmaceutically acceptable salt thereof, the first conjugate, or the pharmaceutically acceptable salt thereof, or the second conjugate, or the pharmaceutically acceptable salt thereof, is about 10 nmol/kg to about 3000 nmol/kg of patient body weight.
30. The method of any one of clauses 1 to 29 wherein the dose of the compound, or the pharmaceutically acceptable salt thereof, the first conjugate, or the pharmaceutically acceptable salt thereof, or the second conjugate, or the pharmaceutically acceptable salt thereof, is about 50 nmol/kg to about 2000 nmol/kg of patient body weight.
31. The method of any one of clauses 1 to 30 wherein the dose of the compound, or the pharmaceutically acceptable salt thereof, the first conjugate, or the pharmaceutically acceptable salt thereof, or the second conjugate, or the pharmaceutically acceptable salt thereof, is about 100 nmol/kg to about 1000 nmol/kg of patient body weight.
32. The method of any one of clauses 1 to 31 wherein the dose of the compound, or the pharmaceutically acceptable salt thereof, the first conjugate, or the pharmaceutically acceptable salt thereof, or the second conjugate, or the pharmaceutically acceptable salt thereof, is about 100 nmol/kg to about 600 nmol/kg of patient body weight.
33. The method of any one of clauses 1 to 32 wherein the dose of the compound, or the pharmaceutically accept-able salt thereof, the first conjugate, or the pharmaceutically acceptable salt thereof, or the second conjugate, or the pharmaceutically acceptable salt thereof, is about 200 nmol/kg to about 500 nmol/kg of patient body weight.
34. The method of any one of clauses 1 to 33 wherein the dose of the compound, or the pharmaceutically acceptable salt thereof, the first conjugate, or the pharmaceutically acceptable salt thereof, or the second conjugate, or the pharmaceutically acceptable salt thereof, is about 250 nmol/kg to about 500 nmol/kg of patient body weight.
35. The method of any one of clauses 1 to 34 wherein the cancer is selected from lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, cancer of the urethra, prostate cancer, chronic leukemia, acute leukemia, lymphocytic lymphoma, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.
36. The method of any one of clauses 1 to 11 or 16 to 35 wherein the cancer is a folate receptor expressing cancer.
37. The method of clause 35 wherein the cancer is an endometrial cancer.
38. The method of clause 35 wherein the cancer is a non-small cell lung cancer.
39. The method of clause 35 wherein the cancer is an ovarian cancer.
40. The method of clause 35 wherein the cancer is a triple negative breast cancer.
41. The method of any one of clauses 1 to 40 wherein the CAR has a recognition region and the recognition region is a single chain fragment variable (scFv) region of an antibody.
42. The method of any one of clauses 1 to 11, 16 to 17, or 20 to 41 wherein the CAR has a recognition region and the recognition region of the CAR is a single chain fragment variable (scFv) region of an anti-FITC antibody.
43. The method of any one of clauses 1 to 42 wherein the CAR has a co-stimulation domain and the co-stimulation domain is selected from CD28, CD137 (4-1BB), CD134 (OX40), and CD278 (ICOS).
44. The method of any one of clauses 1 to 43 wherein the CAR has an activation signaling domain and the activation signaling domain is a T cell CD3ζ chain or an Fc receptor γ.
45. The method of any one of clauses 1 to 11, 16 to 17, or 20 to 41 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

46. The method of any one of clauses 1 to 45 wherein multiple doses of the compound, or the pharmaceutically acceptable salt thereof, the first conjugate, or the pharmaceutically acceptable salt thereof, or the second conjugate, or the pharmaceutically acceptable salt thereof, and the CAR T cell composition are administered.

47. The method of any one of clauses 1 to 46 wherein the patient is imaged prior to administration of the compound, or the pharmaceutically acceptable salt thereof, the first conjugate, or the pharmaceutically acceptable salt thereof, or the second conjugate, or the pharmaceutically acceptable salt thereof, or prior to administration of the CAR T cell composition.

48. The method of any one of clauses 1 to 47 wherein the compound, or the pharmaceutically acceptable salt thereof, the first conjugate, or the pharmaceutically acceptable salt thereof, or the second conjugate, or the pharmaceutically acceptable salt thereof, is not an antibody, and does not comprise a fragment of an antibody.

49. The method of any one of clauses 1 to 48 wherein the targeting moiety is not a peptide epitope.

50. The method of any one of clauses 1 to 49 wherein cytokine release resulting in 'off-target' toxicity in the patient does not occur and wherein CAR T cell toxicity to the cancer occurs.

51. The method of any one of clauses 1 to 50 wherein 'off-target' tissue toxicity does not occur in the patient and wherein CAR T cell toxicity to the cancer occurs.

52. The method of any one of clauses 1 to 51 wherein the cancer comprises a tumor, wherein tumor size is reduced in the patient, and wherein 'off-target' toxicity does not occur.

53. A CAR T cell comprising a nucleic acid comprising SEQ ID NO:1.

54. A CAR T cell comprising a polypeptide comprising SEQ ID NO:2.

55. An isolated nucleic acid comprising SEQ ID NO:1 and encoding a chimeric antigen receptor.

56. A chimeric antigen receptor polypeptide comprising SEQ ID NO:2.

57. A vector comprising SEQ ID NO:1.

58. The vector of clause 57 wherein the vector is a lentiviral vector.

59. The method, CAR T cell, isolated nucleic acid encoding a chimeric antigen receptor (CAR), or chimeric antigen receptor polypeptide of any one of clauses 1 to 56 wherein the CAR comprises human amino acid sequences.

60. The method, CAR T cell, isolated nucleic acid encoding a chimeric antigen receptor (CAR), or chimeric antigen receptor polypeptide of any one of clauses 1 to 56 wherein the CAR consists of human amino acid sequences.

61. A kit comprising at least two different types of bridges wherein the bridges comprise a small molecule ligand linked to a targeting moiety wherein the ligand in the at least two different types of bridges is different and wherein the ligand is selected from a folate, DUPA, a CAIX ligand, an NK-1R ligand, a ligand of gamma glutamyl transpeptidase, and a CCK2R ligand.

62. The kit of clause 61 wherein the ligand in at least one of the bridges is an NK-1R ligand.

63. The kit of clause 61 wherein the ligand in at least one of the bridges is a ligand of gamma glutamyl transpeptidase.

64. The kit of clause 61 wherein the ligand in at least one of the bridges is a folate.

65. The kit of any one of clauses 61 to 64 wherein the bridge has the formula

B-L-T, wherein B represents the small molecule ligand, L represents the linker, and T represents the targeting moiety, and wherein L comprises a structure having the formula

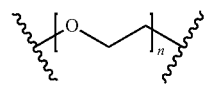

wherein n is an integer from 0 to 200.

66. The kit of clause 65 wherein n is an integer from 0 to 150.

67. The kit of clause 65 wherein n is an integer from 0 to 110.

68. The kit of clause 65 wherein n is an integer from 0 to 20.

69. The kit of clause 65 wherein n is an integer from 15 to 20.

70. The kit of clause 65 wherein n is an integer from 15 to 110.

71. The method of any one of clauses 1 to 10, 16 to 52, or 59 to 60, or the kit of any one of clauses 61 to 70 wherein the ligand is a CAIX ligand.

72. A conjugate of the formula

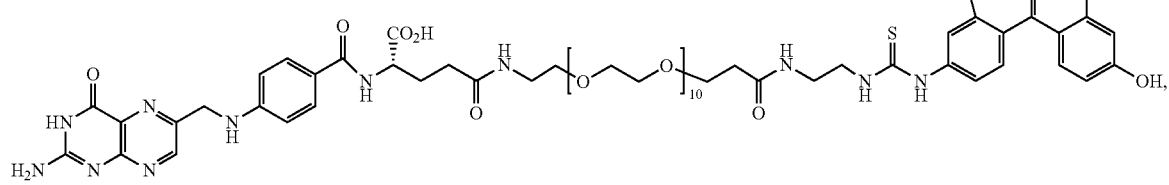

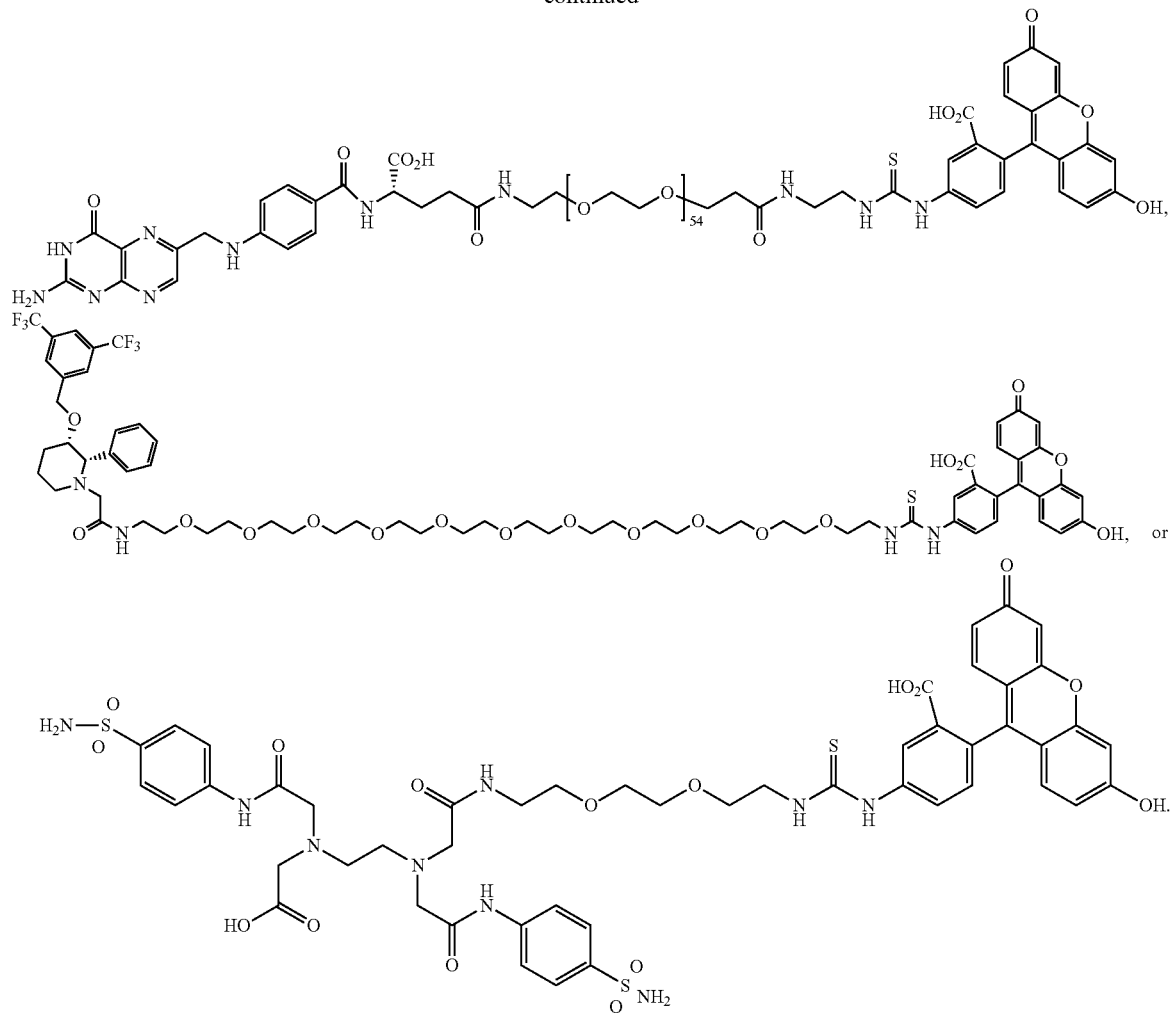

BRIEF DESCRIPTION OF THE DRAWINGS

FIGS. 1A-B show CAR T cell proliferation using FITC-small molecule conjugates in different cell types with a (CAR T cell):target cell (cancer cell) ratio of 5:1. FIG. 1A shows CAR T cell proliferation in KB (FR+) cells. FIG. 1B shows CAR T cell proliferation in HEK293 (NK1R+) cells.

FIGS. 2A-F show inflammatory cytokine IFN-γ production by CAR T cells with FITC-small molecule conjugates in different cell types. FIG. 2A shows inflammatory cytokine IFN-γ production in KB (FR+) cells. FIG. 2B shows inflammatory cytokine IFN-γ production in LNCaP (PSMA+) cells. FIG. 2C shows inflammatory cytokine IFN-γ production in HEK293 (NK1R+) cells. FIG. 2D shows inflammatory cytokine IFN-γ production in KB (FR+) cells with different concentrations of FITC-Folate. FIG. 2E shows inflammatory cytokine IFN-γ production in KB (FR+) cells with different conjugates. FIG. 2F shows inflammatory cytokine IFN-γ production in KB (FR+) cells with different conjugates.

FIGS. 3A-F show in vitro toxicity of tumor cells treated with FITC-small molecule conjugates in different cell types. FIG. 3A shows in vitro toxicity in KB (FR+) cells. FIG. 3B shows in vitro toxicity in LNCaP (PSMA+) cells. FIG. 3C shows in vitro toxicity in HEK293 (NK1R+) cells. FIG. 3D shows in vitro toxicity in KB (FR+) cells as a function of different E:T (Effector cells:Target cells) ratios. FIG. 3E shows in vitro toxicity in KB (FR+) cells as a function of FITC-Folate concentration. FIG. 3F shows in vitro toxicity in KB (FR+) cells with different conjugates.

FIGS. 4A-B show activation of CAR T cells is correlated with the expression level of the tumor antigen on cancer cells. FIG. 4A shows tumor antigen FRα level. The highest peak is for KB (FR+) cells. FIG. 4B shows CAR T cell activation using FITC-small molecule conjugates as measured by IFN-γ production in MDA-MB-231 and KB cells.

FIGS. 5A-C show HEK293 (NK1R+) tumor xenografts and a CAR T cell therapy comprising treating CAR T cells with either a FITC-PEG11-NK1 conjugate or no conjugate. FIG. 5A shows tumor volume measured over 24 days. FIG. 5B shows the body weight measured over 22 days of therapy. FIG. 5C shows the percentage of CAR T cells in CD3+ human T cells post CAR T cell injection along with FITC-PEG11-NK1.

FIGS. 6A-B show harvested organs from exemplary mice of the models used in FIGS. 5A-C. FIG. 6A shows harvested organs from the non-treatment group. FIG. 6B shows harvested organs after two weeks of CAR T cell therapy.

FIGS. 7A-C show MDA-MB-231 (FR+) xenografts under a CAR T cell therapy comprising treating the cells with CAR T cells with either a FITC-PEG12-Folate conjugate, a FITC-Folate conjugate, or no conjugate. FIG. 7A shows tumor volume measured over 23 days. FIG. 7B shows the body weight measured over 21 days of therapy. FIG. 7C shows the percentage of CAR T cells in CD3+ human T cells post CAR T cell injection.

FIGS. 8A-B show harvested organs from exemplary mice from the models shown in FIGS. 7A-C. FIG. 8A shows harvested organs from the non-treatment group. FIG. 8B shows harvested organs after three weeks of CAR T cell therapy comprising CAR T cells and the FITC-PEG12-Folate conjugate at 500 nmoles/kg body weight.

FIG. 9 shows blood indices of the HEK293 (NK1R+) xenograft model from FIGS. 5-6 and the MDA-MB-231 (FR+) xenograft model from FIGS. 7-8.

FIG. 12A shows harvested organs from the non-treatment group. FIG. 12B shows harvested organs from the CAR T cell therapy group treated with 250 nmol/kg FITC-PEG-12-Folate. FIG. 12C shows harvested organs from the CAR T cell therapy group treated with CAR T cells and 500 nmol/kg FITC-PEG-12-Folate.

FIG. 13 shows blood indices of the mice from the KB xenograft model from FIGS. 11-12.

FIGS. 14A-B show the constructs used for CAR T transduction. FIG. 14A shows the CAR4-1BBZ construct. FIG. 14B shows the lentiviral vector.

FIGS. 15A-B show flow cytometry analysis of transduced T cells. FIG. 15A shows the non-transduced cells. FIG. 15B shows the transduced cells.

FIGS. 16A-B show fluorescent microscopy of transduced CAR T cells. FIG. 16A shows GFP imaging indicating transduction. FIG. 16B shows FITC folate localizing to the positively transduced cells.

FIGS. 19A-C shows anti-tumor efficacy when the same anti-FITC CAR T cell ($10^7$ cells) was introduced to mice bearing two different tumors arising from two different cell lines (i.e. MDA-MB-231(FR+) and HEK (NK1R+)) on separate flanks, after which either PBS only (FIG. 19A), FITC-PEG11-NK1R (500 nmole/kg) (FIG. 19B), or FITC-PEG11-NK1R (500 nmole/kg) plus FITC-PEG12-Folate (500 nmole/kg) (FIG. 19C) was injected every other day. FIG. 19A: (●) FR+ (MDA-MB-231): CAR T cell+PBS, (■) NK1R+(HEK): CAR T cell+PBS; FIG. 19B: (●) FR+ (MDA-MB-231): CAR T cell+PBS, (■) NK1R+(HEK): CAR T cell+FITC-PEG11-NK1R (500 nmole/kg); FIG. 19C: (●) FR+ (MDA-MB-231): CART cell+FITC-PEG12-FA (500 nmole/kg), (■) NK1R+(HEK): CAR T cell+PBS.

DEFINITIONS

Figure 10:
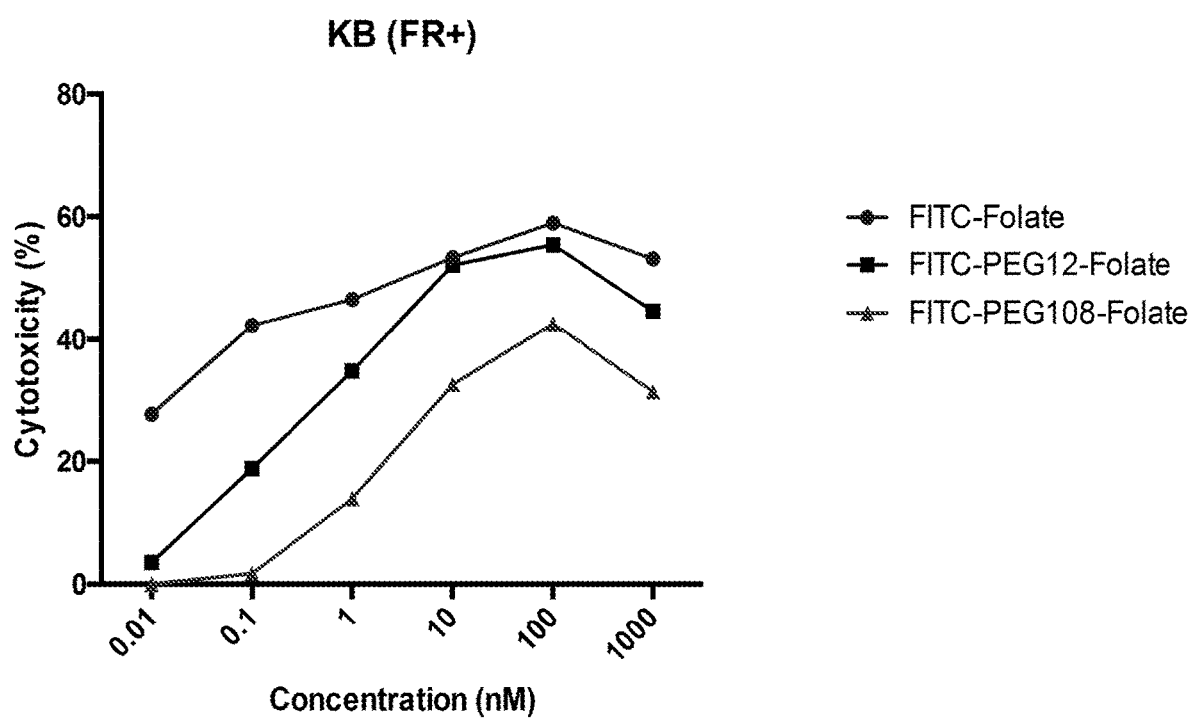
FIG. 10 shows differences in cytotoxicity towards KB (FR+) tumor cells treated with CAR T cells depending on the FITC-small molecule conjugate used.

As used herein, "a" or "an" may mean one or more. As used herein, "about" in reference to a numeric value, including, for example, whole numbers, fractions, and percentages, generally refers to a range of numerical values (e.g., +/−5% to 10% of the recited value) that one of ordinary skill in the art would consider equivalent to the recited value (e.g., having the same function or result).

As used herein, the terms "treat," "treating," "treated," or "treatment" refer to both therapeutic treatment and prophylactic or preventative treatment.

As used herein, the terms "ameliorate," "ameliorating," "amelioration," or "ameliorated" in reference to cancer can mean reducing the symptoms of the cancer, reducing the size of a tumor, completely or partially removing the tumor (e.g., a complete or partial response), causing stable disease, preventing progression of the cancer (e.g., progression free survival), or any other effect on the cancer that would be considered by a physician to be a therapeutic or preventative treatment of the cancer.

As used herein, the terms "administer," administering," or "administered" mean all means of introducing the compound, or pharmaceutically acceptable salt thereof, the first conjugate, or pharmaceutically acceptable salt thereof, the second conjugate, or pharmaceutically acceptable salt thereof, or CAR T cell composition described herein to the patient, including, but not limited to, oral (po), intravenous (iv), intramuscular (im), subcutaneous (sc), and transdermal.

As used herein, the term "off-target toxicity" means organ damage or a reduction in the patient's weight that is unacceptable to the physician treating the patient, or any other effect that is unacceptable to the physician treating the patient, such as B cell aplasia.

As used herein, the terms "transduction" and "transfection" are used equivalently and the terms mean introducing a nucleic acid into a cell by any artificial method, including viral and non-viral methods.

DETAILED DESCRIPTION OF THE ILLUSTRATIVE EMBODIMENTS

In the various embodiments described herein, a small molecule ligand linked to a targeting moiety by a linker is used as a bridge between a cancer and CAR T cells (i.e, cytotoxic T cells expressing a chimeric antigen receptor). The bridge directs the CAR T cells to the cancer for amelioration of the cancer. In one embodiment, the "small molecule ligand" can be a folate, a CAIX ligand, DUPA, an NK-1R ligand, a ligand of gamma glutamyl transpeptidase, or a CCK2R ligand, each of which is a small molecule ligand that binds specifically to a cancer cell type (i.e., the receptor for each of these ligands is overexpressed on cancers compared to normal tissues).

The "targeting moiety" linked to the small molecule ligand binds to the recognition region of the genetically engineered CAR expressed by CAR T cells. Accordingly, the recognition region of the CAR (e.g., a single chain fragment variable region (scFv) of an antibody) is directed to the "targeted moiety." Thus, the small molecule ligand linked to a targeting moiety by a linker acts as a bridge between the cancer and the CAR T cells directing the CAR T cells to the cancer for amelioration of the cancer. In various embodiments, the bridge between the cancer and the CAR T cells can be any of the conjugates shown in Examples 5 to 12.

The bridge is a small organic molecule so clearance from the bloodstream can be rapidly achieved (e.g., about 20 minutes or less). In one aspect, the CAR T cell response can be targeted to only those cancer cells expressing a receptor for the small molecule ligand portion of the 'bridge,' thereby reducing off-target toxicity to normal tissues. In another aspect, CAR T cell activation can be controlled due to the rapid clearance of the bridge from the bloodstream and to the ability to vary the dose and structure of the bridge to regulate CAR T cell activation. Additionally, this system can be 'universal' because one type of CAR T cell construct can be used to target a wide variety of cancers. Illustratively, the targeting moiety recognized by the CAR T cell may remain constant so that one type of CAR T cell construct can be used, while the small molecule ligand that binds to the cancer is altered to allow targeting of a wide variety of cancers.

In one embodiment, the inventors have discovered that varying the dose of the small molecule ligand linked to a targeting moiety by a linker (i.e., the bridge), can result in the ability to control CRS in vivo upon CAR T cell activation. In another embodiment, the inventors have discovered that varying the linker in the small molecule ligand linked to a targeting moiety (the bridge) can control CRS in vivo upon CAR T cell activation. In yet another embodiment, combinations of these methods can be used for precise control of CAR T cell activation and cytokine release in vivo.

In various embodiments described in the clause list below and in the claims, the small molecule ligand linked to a targeting moiety by a linker is referred to as a "compound," a "first conjugate," or a "second conjugate." The term "compound" is used in embodiments where the dose of the small molecule ligand linked to a targeting moiety by a linker is varied to control cytokine release in vivo. The terms "first conjugate" and "second conjugate" are used in embodiments where two different conjugates are administered to a patient. For example, the linker in the small molecule ligand linked to a targeting moiety can be varied to control cytokine release in vivo, or the conjugates can be modified to contain different small molecule ligands or different targeting moieties.

Several embodiments are described by the following enumerated clauses:

1. A method of treatment of a cancer, the method comprising
   i) administering to a patient a first dose of a compound, or a pharmaceutically acceptable salt thereof, wherein the compound comprises a small molecule ligand linked to a targeting moiety by a linker;
   ii) administering to the patient a CAR T cell composition wherein the CAR T cell comprises a CAR directed to the targeting moiety;
   ii) administering to the patient a second dose of the compound, or the pharmaceutically acceptable salt thereof, wherein the second dose is different than the first dose; and
   iv) treating the patient to ameliorate the cancer.
2. A method of treatment of a cancer, the method comprising
   i) administering to the patient a first conjugate, or a pharmaceutically acceptable salt thereof;
   ii) administering to the patient a CAR T cell composition wherein the CAR T cell comprises a CAR directed to the targeting moiety;
   iii) administering to the patient a second conjugate, or a pharmaceutically acceptable salt thereof, wherein the first and the second conjugate each comprise a small molecule ligand linked to a targeting moiety by a linker and wherein the first conjugate and the second conjugate are different; and
   iv) treating the patient to ameliorate the cancer.
3. A method of treatment of a cancer, the method comprising
   i) administering to a patient a first dose of a first conjugate, or a pharmaceutically acceptable salt thereof;
   ii) administering to the patient a CAR T cell composition wherein the CAR T cell comprises a CAR directed to the targeting moiety;
   ii) administering to the patient a second dose of a second conjugate, or a pharmaceutically acceptable salt thereof,
   wherein the first conjugate and the second conjugate each comprise a small molecule ligand linked to a targeting moiety, wherein the first conjugate and the second conjugate are different, and wherein the first dose and the second dose are different; and
   iv) treating the patient to ameliorate the cancer.
4. The method of clause 2 or 3 wherein the linker in the first conjugate, or the pharmaceutically acceptable salt thereof, and the linker in the second conjugate, or the pharmaceutically acceptable salt thereof, are different.
5. The method of clause 2 or 3 wherein the linker in the first conjugate, or the pharmaceutically acceptable salt thereof, and the linker in the second conjugate, or the pharmaceutically acceptable salt thereof, are the same.
6. The method of any one of clauses 2 to 5 wherein the ligand in the first conjugate, or the pharmaceutically acceptable salt thereof, and the ligand in the second conjugate, or the pharmaceutically acceptable salt thereof, are different.
7. The method of any one of clauses 2 to 5 wherein the ligand in the first conjugate, or the pharmaceutically acceptable salt thereof, and the ligand in the second conjugate, or the pharmaceutically acceptable salt thereof, are the same.
8. The method of any one of clauses 2 to 7 wherein the targeting moiety in the first conjugate, or the pharmaceutically acceptable salt thereof, and the targeting moiety in the second conjugate, or the pharmaceutically acceptable salt thereof, are different.
9. The method of any one of clauses 2 to 7 wherein the targeting moiety in the first conjugate, or the pharmaceutically acceptable salt thereof, and the targeting moiety in the second conjugate, or the pharmaceutically acceptable salt thereof, are the same.
10. The method of any one of clauses 1 to 9 wherein the ligand is selected from a folate, DUPA, a CAIX ligand, an NK-1R ligand, a ligand of gamma glutamyl transpeptidase, and a CCK2R ligand.
11. The method of clause 10 wherein the ligand is a folate.
12. The method of clause 10 wherein the ligand is an NK-1R ligand.
13. The method of clause 10 wherein the ligand is DUPA.
14. The method of clause 10 wherein the ligand is a CCK2R ligand.
15. The method of clause 10 wherein the ligand is a ligand of gamma glutamyl transpeptidase.
16. The method of any one of clauses 1 to 15 wherein the targeting moiety is selected from 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester (PFP), tetrafluorophenyl ester (TFP), a knottin, a centyrin, and a DARPin.
17. The method of clause 16 wherein the targeting moiety is FITC.

18. The method of clause 16 wherein the targeting moiety is DNP.
19. The method of clause 16 wherein the targeting moiety is TNP.
20. The method of any one of clauses 1 to 19 wherein the linker comprises polyethylene glycol (PEG), polyproline, a hydrophilic amino acid, a sugar, an unnatural peptidoglycan, a polyvinylpyrrolidone, and/or pluronic F-127.
21. The method of clause 20 wherein the linker comprises PEG.
22. The method of any one of clauses 1 to 21 wherein the compound, or the pharmaceutically acceptable salt thereof, the first conjugate, or the pharmaceutically acceptable salt thereof, or the second conjugate or the pharmaceutically acceptable salt thereof, has the formula

B-L-T, wherein B represents the small molecule ligand, L represents the linker, and T represents the targeting moiety, and wherein L comprises a structure having the formula

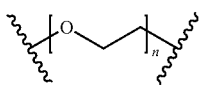

wherein n is an integer from 0 to 200.
23. The method of clause 22 wherein n is an integer from 0 to 150.
24. The method of clause 22 wherein n is an integer from 0 to 110.
25. The method of clause 22 wherein n is an integer from 0 to 20.
26. The method of clause 22 wherein n is an integer from 15 to 20.
27. The method of clause 22 wherein n is an integer from 15 to 110.
28. The method of any one of clauses 1 to 27 wherein the linker comprises PEG and the targeting moiety is FITC, or a pharmaceutically acceptable salt thereof.
29. The method of any one of clauses 1 to 28 wherein the dose of the compound, or the pharmaceutically acceptable salt thereof, the first conjugate, or the pharmaceutically acceptable salt thereof, or the second conjugate, or the pharmaceutically acceptable salt thereof, is about 10 nmol/kg to about 3000 nmol/kg of patient body weight.
30. The method of any one of clauses 1 to 29 wherein the dose of the compound, or the pharmaceutically acceptable salt thereof, the first conjugate, or the pharmaceutically acceptable salt thereof, or the second conjugate, or the pharmaceutically acceptable salt thereof, is about 50 nmol/kg to about 2000 nmol/kg of patient body weight.
31. The method of any one of clauses 1 to 30 wherein the dose of the compound, or the pharmaceutically acceptable salt thereof, the first conjugate, or the pharmaceutically acceptable salt thereof, or the second conjugate, or the pharmaceutically acceptable salt thereof, is about 100 nmol/kg to about 1000 nmol/kg of patient body weight.
32. The method of any one of clauses 1 to 31 wherein the dose of the compound, or the pharmaceutically acceptable salt thereof, the first conjugate, or the pharmaceutically acceptable salt thereof, or the second conjugate, or the pharmaceutically acceptable salt thereof, is about 100 nmol/kg to about 600 nmol/kg of patient body weight.
33. The method of any one of clauses 1 to 32 wherein the dose of the compound, or the pharmaceutically acceptable salt thereof, the first conjugate, or the pharmaceutically acceptable salt thereof, or the second conjugate, or the pharmaceutically acceptable salt thereof, is about 200 nmol/kg to about 500 nmol/kg of patient body weight.
34. The method of any one of clauses 1 to 33 wherein the dose of the compound, or the pharmaceutically acceptable salt thereof, the first conjugate, or the pharmaceutically acceptable salt thereof, or the second conjugate, or the pharmaceutically acceptable salt thereof, is about 250 nmol/kg to about 500 nmol/kg of patient body weight.
35. The method of any one of clauses 1 to 34 wherein the cancer is selected from lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, cancer of the urethra, prostate cancer, chronic leukemia, acute leukemia, lymphocytic lymphoma, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.
36. The method of any one of clauses 1 to 11 or 16 to 35 wherein the cancer is a folate receptor expressing cancer.
37. The method of clause 35 wherein the cancer is an endometrial cancer.
38. The method of clause 35 wherein the cancer is a non-small cell lung cancer.
39. The method of clause 35 wherein the cancer is an ovarian cancer.
40. The method of clause 35 wherein the cancer is a triple negative breast cancer.
41. The method of any one of clauses 1 to 40 wherein the CAR has a recognition region and the recognition region is a single chain fragment variable (scFv) region of an antibody.
42. The method of any one of clauses 1 to 11, 16 to 17, or 20 to 41 wherein the CAR has a recognition region and the recognition region of the CAR is a single chain fragment variable (scFv) region of an anti-FITC antibody.
43. The method of any one of clauses 1 to 42 wherein the CAR has a co-stimulation domain and the co-stimulation domain is selected from CD28, CD137 (4-1BB), CD134 (OX40), and CD278 (ICOS).
44. The method of any one of clauses 1 to 43 wherein the CAR has an activation signaling domain and the activation signaling domain is a T cell CD3ζ chain or an Fc receptor γ.
45. The method of any one of clauses 1 to 11, 16 to 17, or 20 to 41 wherein the CAR has a recognition region and the recognition region is a single chain fragment variable (scFv) region of an anti-FITC antibody, wherein the CAR has a co-stimulation domain and the co-stimulation domain is CD137 (4-1BB), and wherein the CAR has an activation signaling domain and the activation signaling domain is a T cell CD3ζ chain.

46. The method of any one of clauses 1 to 45 wherein multiple doses of the compound, or the pharmaceutically acceptable salt thereof, the first conjugate, or the pharmaceutically acceptable salt thereof, or the second conjugate, or the pharmaceutically acceptable salt thereof, and the CAR T cell composition are administered.

47. The method of any one of clauses 1 to 46 wherein the patient is imaged prior to administration of the compound, or the pharmaceutically acceptable salt thereof, the first conjugate, or the pharmaceutically acceptable salt thereof, or the second conjugate, or the pharmaceutically acceptable salt thereof, or prior to administration of the CAR T cell composition.

48. The method of any one of clauses 1 to 47 wherein the compound, or the pharmaceutically acceptable salt thereof, the first conjugate, or the pharmaceutically acceptable salt thereof, or the second conjugate, or the pharmaceutically acceptable salt thereof, is not an antibody, and does not comprise a fragment of an antibody.

49. The method of any one of clauses 1 to 48 wherein the targeting moiety is not a peptide epitope.

50. The method of any one of clauses 1 to 49 wherein cytokine release resulting in 'off-target' toxicity in the patient does not occur and wherein CAR T cell toxicity to the cancer occurs.

51. The method of any one of clauses 1 to 50 wherein 'off-target' tissue toxicity does not occur in the patient and wherein CAR T cell toxicity to the cancer occurs.

52. The method of any one of clauses 1 to 51 wherein the cancer comprises a tumor, wherein tumor size is reduced in the patient, and wherein 'off-target' toxicity does not occur.

53. A CAR T cell comprising a nucleic acid comprising SEQ ID NO:1.

54. A CAR T cell comprising a polypeptide comprising SEQ ID NO:2.

55. An isolated nucleic acid comprising SEQ ID NO:1 and encoding a chimeric antigen receptor.

56. A chimeric antigen receptor polypeptide comprising SEQ ID NO:2.

57. A vector comprising SEQ ID NO:1.

58. The vector of clause 57 wherein the vector is a lentiviral vector.

59. The method, CAR T cell, isolated nucleic acid encoding a chimeric antigen receptor (CAR), or chimeric antigen receptor polypeptide of any one of clauses 1 to 56 wherein the CAR comprises human amino acid sequences.

60. The method, CAR T cell, isolated nucleic acid encoding a chimeric antigen receptor (CAR), or chimeric antigen receptor polypeptide of any one of clauses 1 to 56 wherein the CAR consists of human amino acid sequences.

61. A kit comprising at least two different types of bridges wherein the bridges comprise a small molecule ligand linked to a targeting moiety wherein the ligand in the at least two different types of bridges is different and wherein the ligand is selected from a folate, DUPA, a CAIX ligand, an NK-1R ligand, a ligand of gamma glutamyl transpeptidase, and a CCK2R ligand.

62. The kit of clause 61 wherein the ligand in at least one of the bridges is an NK-1R ligand.

63. The kit of clause 61 wherein the ligand in at least one of the bridges is a ligand of gamma glutamyl transpeptidase.

64. The kit of clause 61 wherein the ligand in at least one of the bridges is a folate.

65. The kit of any one of clauses 61 to 64 wherein the bridge has the formula

B-L-T, wherein B represents the small molecule ligand, L represents the linker, and T represents the targeting moiety, and wherein L comprises a structure having the formula wherein n is an integer from 0 to 200.

66. The kit of clause 65 wherein n is an integer from 0 to 150.

67. The kit of clause 65 wherein n is an integer from 0 to 110.

68. The kit of clause 65 wherein n is an integer from 0 to 20.

69. The kit of clause 65 wherein n is an integer from 15 to 20.

70. The kit of clause 65 wherein n is an integer from 15 to 110.

71. The method of any one of clauses 1 to 10, 16 to 52, or 59 to 60, or the kit of any one of clauses 61 to 70 wherein the ligand is a CAIX ligand.

72. A conjugate of the formula

-continued

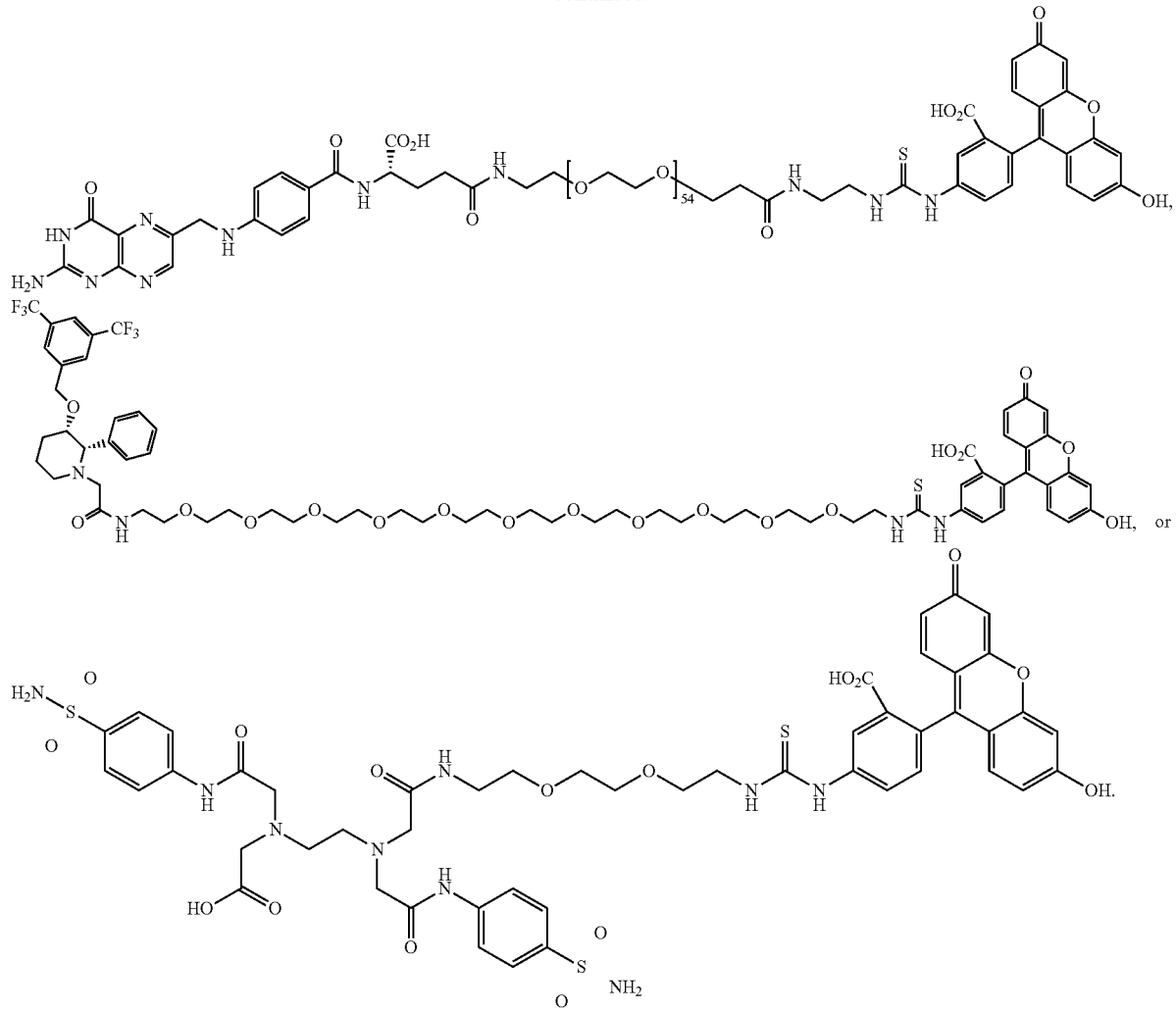

As described herein, a "patient" can be a human or, in the case of veterinary applications, the patient can be a laboratory, an agricultural, a domestic, or a wild animal. In one aspect, the patient can be a laboratory animal such as a rodent (e.g., mouse, rat, hamster, etc.), a rabbit, a monkey, a chimpanzee, a domestic animal such as a dog, a cat, or a rabbit, an agricultural animal such as a cow, a horse, a pig, a sheep, a goat, or a wild animal in captivity such as a bear, a panda, a lion, a tiger, a leopard, an elephant, a zebra, a giraffe, a gorilla, a dolphin, or a whale. In the methods described herein, the step of "treating the patient to ameliorate the cancer" can comprise or consist of the administering steps in the method.

In one illustrative embodiment, the small molecule ligand linked to a targeting moiety by a linker (the bridge) comprises fluorescein isothiocyanate (FITC) linked to the small molecule ligand. The cancer overexpresses a receptor for the small molecule ligand. As a second component, for example, cytotoxic T cells are transformed to express a CAR that comprises anti-FITC scFv. In this aspect, the CAR targets FITC decorating the cancer with FITC molecules as a result of binding of the small molecule ligand to the cancer. Thus, toxicity to normal, non-target cells can be avoided. When the anti-FITC CAR-expressing T cells bind FITC, the CAR T cells are activated and the cancer is ameliorated (e.g., by killing the cancer cells).

In one embodiment, the "small molecule ligand" can be a folate, DUPA (a ligand bound by PSMA-positive human prostate cancer cells and other cancer cell types), an NK-1R ligand (receptors for NK-1R the ligand found, for example, on cancers of the colon and pancreas), a CAIX ligand (receptors for the CAIX ligand found, for example, on renal, ovarian, vulvar, and breast cancers), a ligand of gamma glutamyl transpeptidase (the transpeptidase overexpressed, for example, in ovarian cancer, colon cancer, liver cancer, astrocytic gliomas, melanomas, and leukemias), or a CCK2R ligand (receptors for the CCK2R ligand found on cancers of the thyroid, lung, pancreas, ovary, brain, stomach, gastrointestinal stroma, and colon, among others), each of which is a small molecule ligand that binds specifically to a cancer cell type (i.e., the receptor for each of these ligands can be overexpressed on cancers compared to normal tissues). In one embodiment, a DUPA derivative can be the ligand of the small molecule ligand linked to a targeting moiety, and DUPA derivatives are described in WO 2015/057852, incorporated herein by reference.

In one embodiment, the small molecule ligand is a folate. The folate can be folic acid, a folic acid analog, or another folate receptor-binding molecule. In various embodiments, analogs of folate that can be used include folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid analogs are conventionally termed "folates," reflecting their capacity to bind to folate receptors. Other folate receptor-binding analogs include aminopterin, amethopterin (methotrexate), N10-methylfolate, 2-deamino-hydroxyfolate, deaza analogs such as 1-deazamethopterin or 3-deazamethopterin, and 3',5'-dichloro-4-amino-4-deoxy-N10-methylpteroylglutamic acid (dichloromethotrexate).

In one embodiment, the small molecule ligand may have a mass of less than about 10,000 Daltons, less than about 9000 Daltons, less than about 8,000 Daltons, less than about 7000 Daltons, less than about 6000 Daltons, less than about 5000 Daltons, less than about 4500 Daltons, less than about 4000 Daltons, less than about 3500 Daltons, less than about 3000 Daltons, less than about 2500 Daltons, less than about 2000 Daltons, less than about 1500 Daltons, less than about 1000 Daltons, or less than about 500 Daltons. In another embodiment, the small molecule ligand may have a mass of about 1 to about 10,000 Daltons, about 1 to about 9000 Daltons, about 1 to about 8,000 Daltons, about 1 to about 7000 Daltons, about 1 to about 6000 Daltons, about 1 to about 5000 Daltons, about 1 to about 4500 Daltons, about 1 to about 4000 Daltons, about 1 to about 3500 Daltons, about 1 to about 3000 Daltons, about 1 to about 2500 Daltons, about 1 to about 2000 Daltons, about 1 to about 1500 Daltons, about 1 to about 1000 Daltons, or about 1 to about 500 Daltons.

In one aspect, the "targeting moiety" that binds to the CAR expressed by CAR T cells can be selected, for example, from 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester (PFP), tetrafluorophenyl ester (TFP), a knottin, a centyrin, and a DARPin. The identity of the targeting moiety is limited only in that it should be recognized and bound by the CAR, preferably with specificity, and that it have a relatively low molecular weight. In various aspects, exemplary targeting moieties are haptens that include small molecular weight organic molecules.

In one illustrative embodiment, the targeting moiety can have the following illustrative structure:

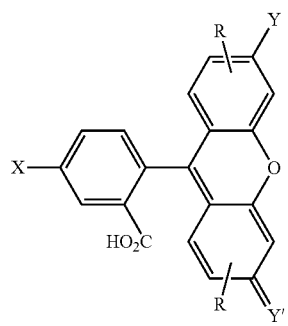

where X is oxygen, nitrogen, or sulfur, and where X is attached to linker L; Y is $OR^a$, $NR^a_2$, or $NR^a_3{}^+$; and Y' is O, $NR^a$, or $NR^a_2{}^+$; where each R is independently selected in each instance from H, fluoro, sulfonic acid, sulfonate, and salts thereof, and the like; and $R^a$ is hydrogen or alkyl.

In one illustrative aspect, the linker in the compound, or pharmaceutically acceptable salt thereof, the first conjugate, or pharmaceutically acceptable salt thereof, the second conjugate, or pharmaceutically acceptable salt thereof, described herein can be a direct linkage (e.g., a reaction between the isothiocyanate group of FITC and a free amine group of a small molecule ligand) or the linkage can be through an intermediary linker. In one embodiment, if present, an intermediary linker can be any biocompatible linker known in the art, such as a divalent linker. In one illustrative embodiment, the divalent linker can comprise about 1 to about 30 carbon atoms. In another illustrative embodiment, the divalent linker can comprise about 2 to about 20 carbon atoms. In other embodiments, lower molecular weight divalent linkers (i.e., those having an approximate molecular weight of about 30 to about 300) are employed. In another embodiment, linkers lengths that are suitable include, but are not limited to, linkers having 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40, or more atoms.

In various embodiments, the small molecule ligand linked to a targeting moiety can be of the formula

B-L-T, wherein B represents the small molecule ligand, L represents the linker, and T represents the targeting moiety, and wherein L comprises a structure having the formula

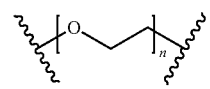

wherein n is an integer from 0 to 200. In another embodiment, n can be an integer from 0 to 150, 0 to 110, 0 to 100, 0 to 90, 0 to 80, 0 to 70, 0 to 60, 0 to 50, 0 to 40, 0 to 30, 0 to 20, 0 to 15, 0 to 14, 0 to 13, 0 to 12, 0 to 11, 0 to 10, 0 to 9, 0 to 8, 0 to 7, 0 to 6, 0 to 5, 0 to 4, 0 to 3, 0 to 2, 0 to 1, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 15 to 31, 15 to 32, 15 to 33, 15 to 34, 15 to 35, 15 to 36, 15 to 37, 15 to 38, 15 to 39, 15 to 40, 15 to 50, 15 to 60, 15 to 70, 15 to 80, 15 to 90, 15 to 100, 15 to 110, 15 to 120, 15 to 130, 15 to 140, 15 to 150, or n can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 108, 110, 120, 130, 140, or 150.

In another embodiment, the linker may be a divalent linker that may include one or more spacers. Illustrative spacers are shown in the following table. The following non-limiting, illustrative spacers are described where * indicates the point of attachment to the small molecule ligand or the targeting moiety.

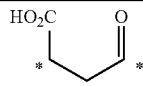

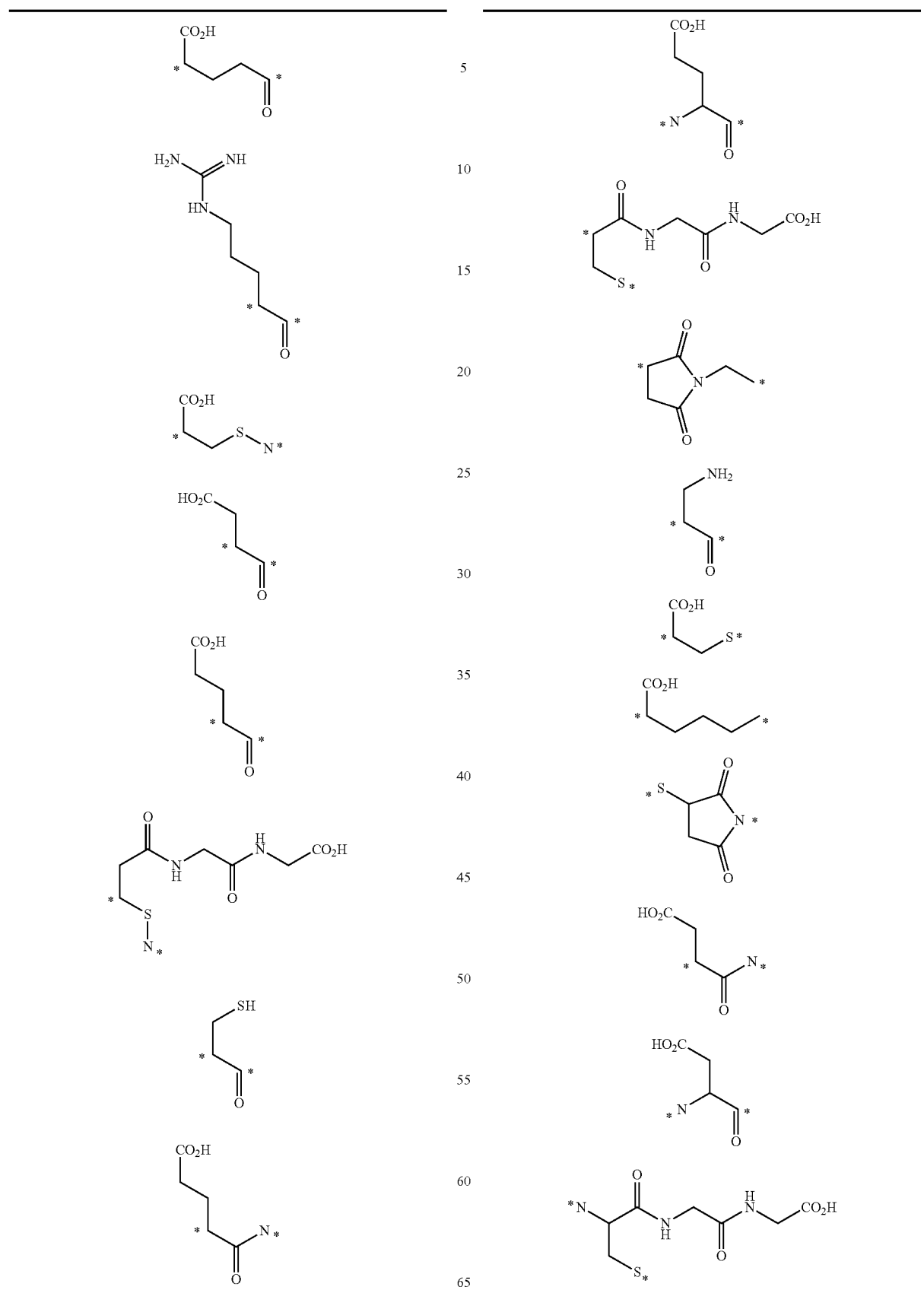

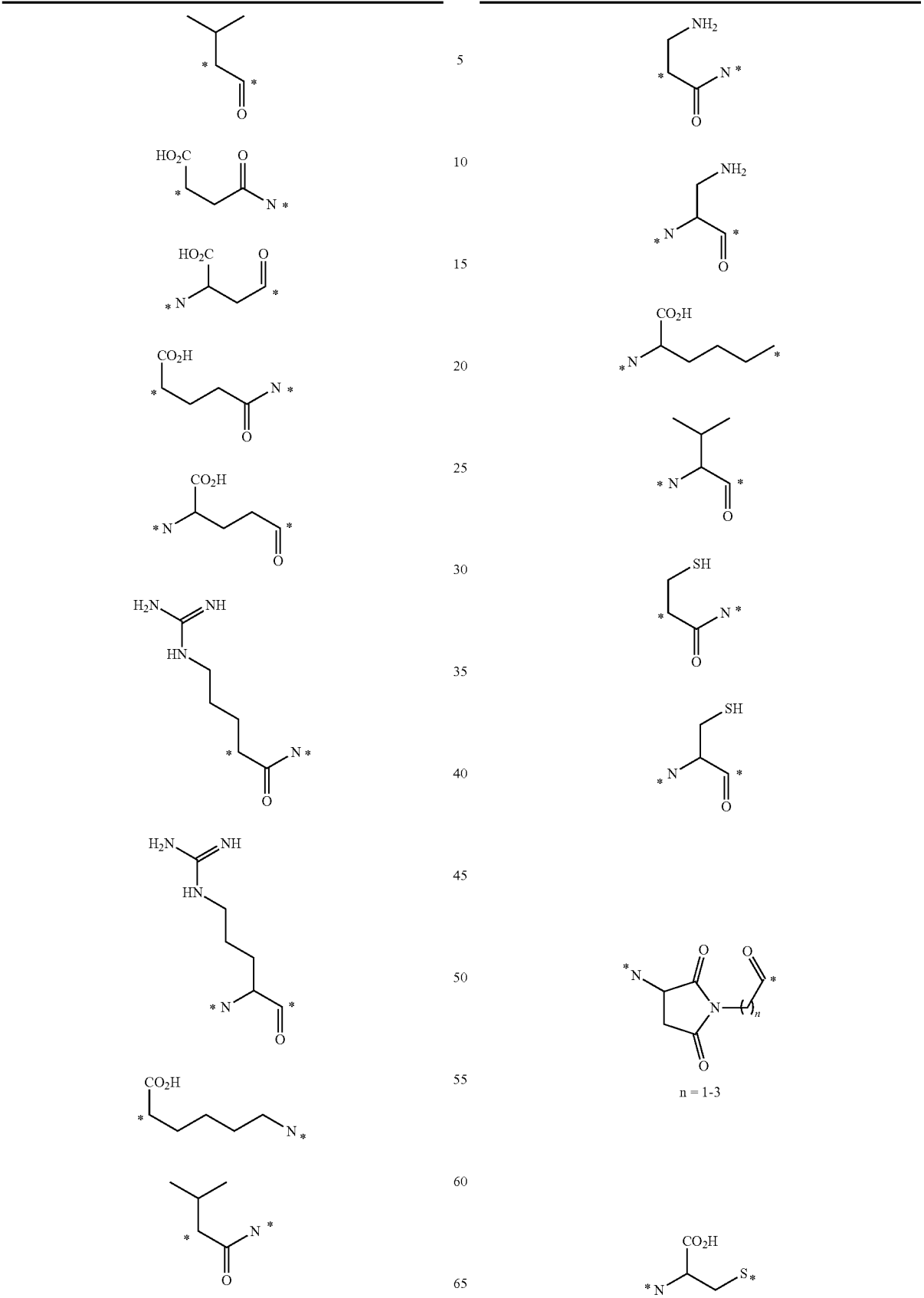

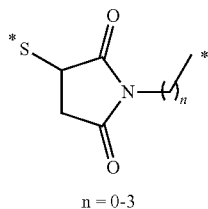
n = 0-3
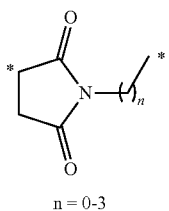
n = 0-3
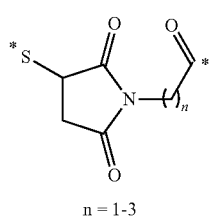
n = 1-3
In other embodiments, the small molecule ligand linked to a targeting moiety (bridge) can have any of the following structures.
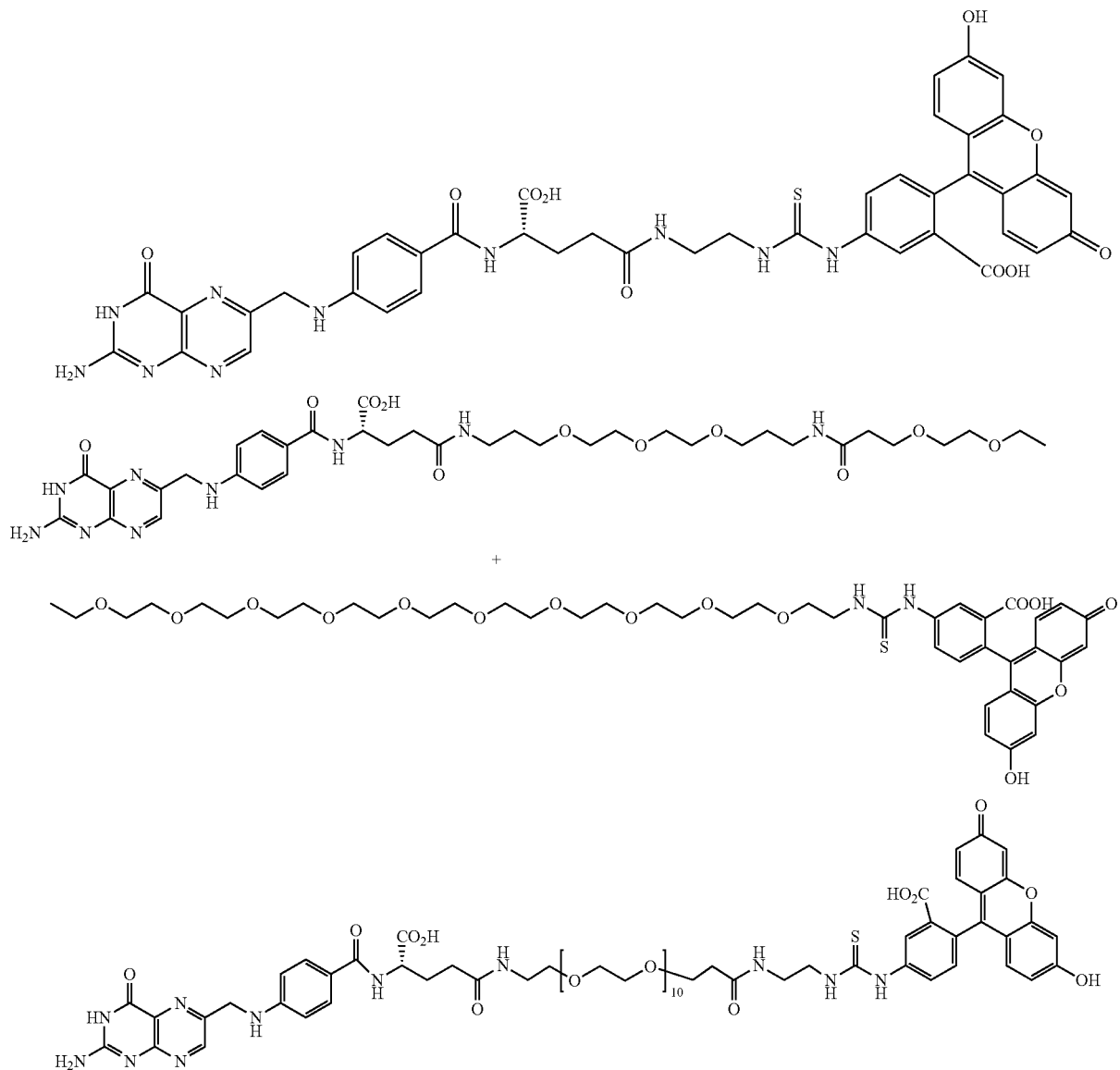

-continued
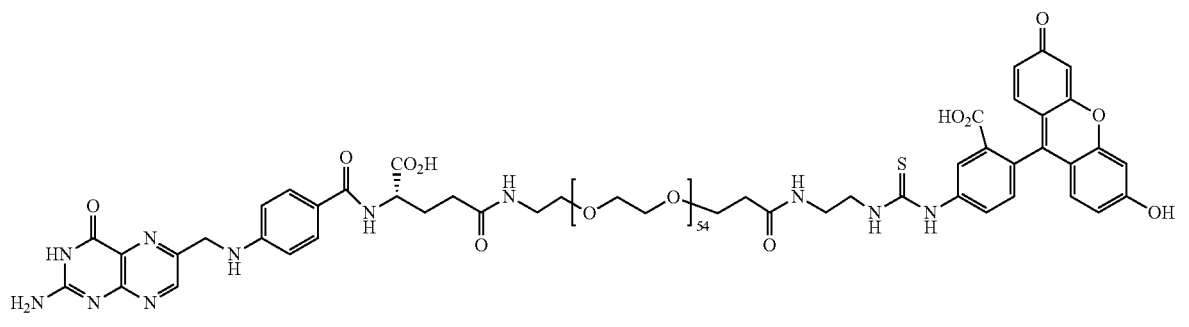
+
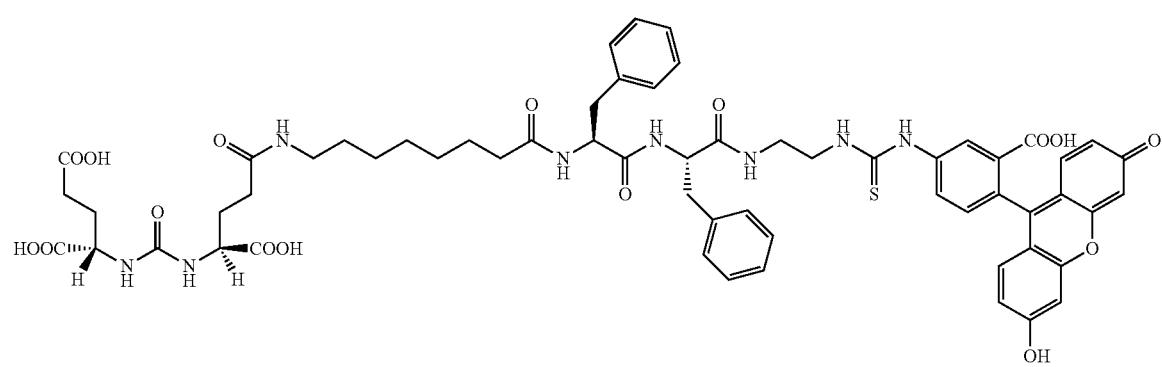
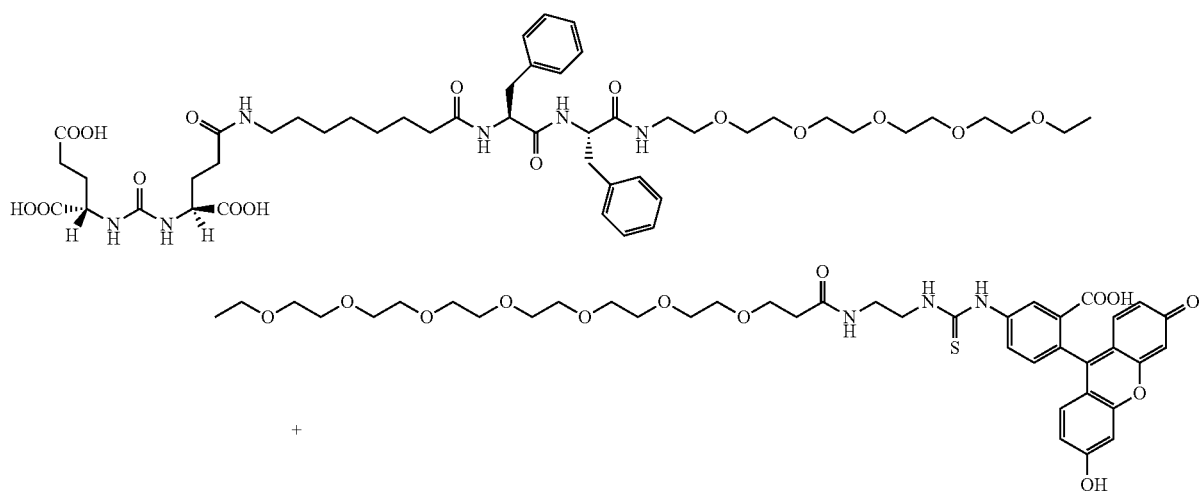
+
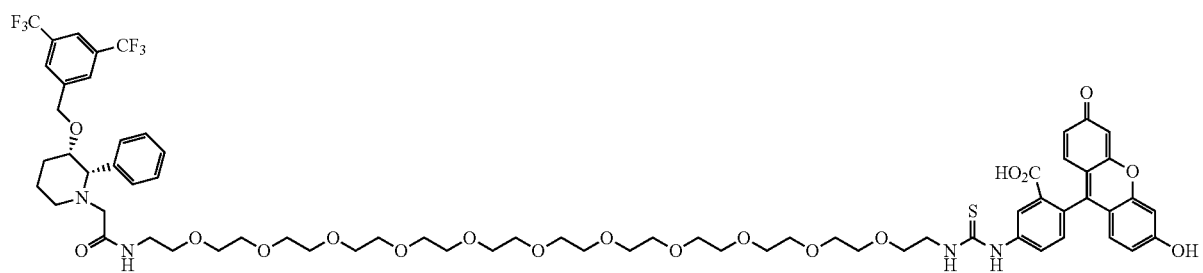

-continued

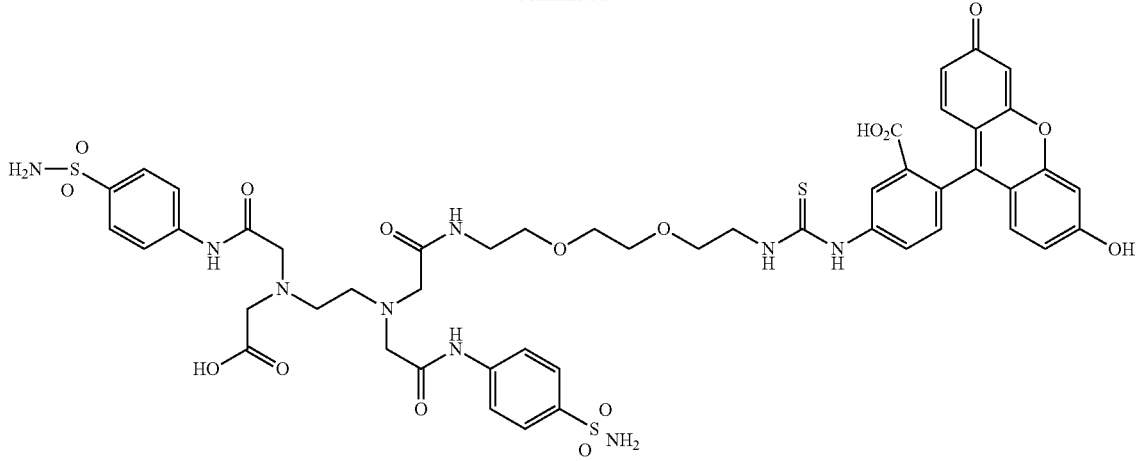

In other embodiments, the compound, or the pharmaceutically acceptable salt thereof, the first conjugate, or the pharmaceutically acceptable salt thereof, or the second conjugate, or the pharmaceutically acceptable salt thereof, is not an antibody, and does not comprise a fragment of an antibody. In yet another embodiment, the targeting moiety is not a peptide epitope.

In one illustrative aspect, different type of conjugates (e.g., a first conjugate and a second conjugate) can be administered to the patient. For example, the linker in the first conjugate, or the pharmaceutically acceptable salt thereof, and the linker in the second conjugate, or the pharmaceutically acceptable salt thereof, can be the same or different. In another aspect, the ligand in the first conjugate, or the pharmaceutically acceptable salt thereof, and the ligand in the second conjugate, or the pharmaceutically acceptable salt thereof, can be the same or different. In another exemplary embodiment, the targeting moiety in the first conjugate, or the pharmaceutically acceptable salt thereof, and the targeting moiety in the second conjugate, or the pharmaceutically acceptable salt thereof, can be the same or different. Any combinations of these embodiments are also contemplated along with any combinations of the doses described below.

In still another embodiment, a kit is provided comprising at least two different types of bridges, wherein the bridges comprise a small molecule ligand linked to a targeting moiety wherein the ligand in the at least two different types of bridges is different and wherein the ligand is selected from a folate, DUPA, a CAIX ligand, an NK-1R ligand, a ligand of gamma glutamyl transpeptidase, and a CCK2R ligand. In this embodiment, the ligand in at least one of the bridges can be an NK-1R ligand, a ligand of gamma glutamyl transpeptidase, a folate, a CAIX ligand, a CCK2R ligand, or DUPA.

In another aspect, the bridge in the kit can have the formula

B-L-T, wherein B represents the small molecule ligand, L represents the linker, and T represents the targeting moiety, and wherein L comprises a structure having the formula wherein n is an integer from 0 to 200. In other embodiments, n can be an integer from 0 to 150, an integer from 0 to 110, an integer from 0 to 20, an integer from 15 to 20, an integer from 15 to 110, or any other value or range of integers described herein for n.

A "pharmaceutically acceptable salt" of a small molecule ligand linked to a targeting moiety by a linker is contemplated. As used herein, the term "pharmaceutically acceptable salt" refers to those salts whose counter ions may be used in pharmaceuticals. Such salts include 1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or 2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like. Pharmaceutically acceptable salts are well-known to those skilled in the art, and any such pharmaceutically acceptable salt may be contemplated in connection with the embodiments described herein.

In various embodiments, suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

In various embodiments, suitable base salts are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

In one illustrative aspect, the compound, or a pharmaceutically salt thereof, the first conjugate, or a pharmaceutically acceptable salt thereof, or the second conjugate, or a pharmaceutically acceptable salt thereof, described herein may contain one or more chiral centers, or may otherwise be capable of existing as multiple stereoisomers. Accordingly, various embodiments may include pure stereoisomers as well as mixtures of stereoisomers, such as enantiomers, diastereomers, and enantiomerically or diastereomerically enriched mixtures. In one aspect, the compound, or pharmaceutically acceptable salt thereof, the first conjugate, or pharmaceutically acceptable salt thereof, the second conjugate, or pharmaceutically acceptable salt thereof, described herein may be capable of existing as geometric isomers. Accordingly, various embodiments may include pure geometric isomers or mixtures of geometric isomers.

In some aspects, the compound, or pharmaceutically acceptable salt thereof, the first conjugate, or pharmaceutically acceptable salt thereof, the second conjugate, or pharmaceutically acceptable salt thereof, described herein may exist in unsolvated forms as well as solvated forms, including hydrated forms. In general, the solvated forms are equivalent to unsolvated forms and are encompassed within the scope of the present invention.

The methods described herein also utilize cytotoxic T lymphocytes engineered to express a chimeric antigen receptor (CAR) that recognizes and binds to the targeting moiety (e.g., FITC, DNP, or TNP) of the bridge. In one embodiment, the CARs described herein comprise three domains including 1) a recognition region (e.g., a single chain fragment variable (scFv) region of an antibody) which recognizes and binds to the targeting moiety with specificity, 2) a co-stimulation domain which enhances the proliferation and survival of the T lymphocytes, and 3) an activation signaling domain which generates a cytotoxic T lymphocyte activation signal.

In various aspects, as non-limiting examples, scFv regions of antibodies that bind a folate, DUPA, a CAIX ligand, an NK-1R ligand, a ligand of gamma glutamyl transpeptidase, or a CCK2R ligand can be used. In illustrative embodiments, the scFv regions can be prepared from (i) an antibody known in the art that binds a targeting moiety, (ii) an antibody newly prepared using a selected targeting moiety, such as a hapten, and (iii) sequence variants derived from the scFv regions of such antibodies, e.g., scFv regions having at least about 80%, at least about 90%, at least about 95%, at least about 97%, at least about 98%, at least about 99%, or at least about 99.5% sequence identity to the amino acid sequence of the scFv region from which they are derived.

In any embodiments described herein, the binding portion of the CAR can be, for example, a single chain fragment variable region (scFv) of an antibody, an Fab, Fv, Fc, or (Fab')2 fragment, and the like.

In one aspect, the co-stimulation domain serves to enhance the proliferation and survival of the cytotoxic T lymphocytes upon binding of the CAR to a targeting moiety. Suitable co-stimulation domains include: 1) CD28, 2) CD137 (4-1BB), a member of the tumor necrosis factor (TNF) receptor family, 3) CD134 (OX40), a member of the TNFR-superfamily of receptors, and 4) CD278 (ICOS), a CD28-superfamily co-stimulatory molecule expressed on activated T cells, or combinations thereof. Suitable co-stimulation domains also include, but are not limited to, CD27, CD30, CD150, DAP10, and NKG2D, or combinations thereof. A skilled artisan will understand that sequence variants of these co-stimulation domains can be used without adversely impacting the invention, where the variants have the same or similar activity as the domain on which they are modeled. In various embodiments, such variants have at least about 80%, at least about 90%, at least about 95%, at least about 97%, at least about 98%, at least about 99%, or at least about 99.5% sequence identity to the amino acid sequence of the domain from which they are derived.

In an illustrative embodiment, the activation signaling domain serves to activate cytotoxic T lymphocytes upon binding of the CAR to a targeting moiety. Suitable activation signaling domains include the T cell CD3ζ chain and Fc receptor γ. The skilled artisan will understand that sequence variants of these noted activation signaling domains can be used where the variants have the same or similar activity as the domain on which they are modeled. In various embodiments, the variants have at least about 80%, at least about 90%, at least about 95%, at least about 97%, at least about 98%, at least about 99%, or at least about 99.5% sequence identity to the amino acid sequence of the domain from which they are derived.

In one aspect, constructs encoding the CARs are prepared using genetic engineering techniques. Such techniques are described in detail in Sambrook et al., "Molecular Cloning: A Laboratory Manual", 3rd Edition, Cold Spring Harbor Laboratory Press, (2001), incorporated herein by reference. As an example, a plasmid or viral expression vector (e.g., a lentiviral vector, a retrovirus vector, sleeping beauty, and piggyback (transposon/transposase systems that include a non-viral mediated CAR gene delivery system)) can be prepared that encodes a fusion protein comprising a recognition region, one or more co-stimulation domains, and an activation signaling domain, in frame and linked in a 5' to 3' direction. In other embodiments, other arrangements are acceptable and include a recognition region, an activation signaling domain, and one or more co-stimulation domains. The placement of the recognition region in the fusion protein will generally be such that display of the region on the exterior of the cell is achieved. In one embodiment, the CARs may include additional elements, such as a signal peptide to ensure proper export of the fusion protein to the cell surface, a transmembrane domain to ensure the fusion protein is maintained as an integral membrane protein, and a hinge domain that imparts flexibility to the recognition region and allows strong binding to the targeting moiety.

Diagrams of an exemplary CAR are shown in FIGS. 14A and B where the fusion protein sequence is incorporated into a lentivirus expression vector and where "SP" is a signal peptide, the CAR is an anti-FITC CAR, a CD8α hinge and a transmembrane (TM) region is present, the co-stimulation domain is 4-1BB, and the activation signaling domain is CD3ζ. In one aspect, the nucleic acid sequence of the CAR insert is provided as SEQ ID NO:1 and the amino acid sequence of the insert is provided as SEQ ID NO:2.

In one embodiment, the CAR has a recognition region and the recognition region is a single chain fragment variable (scFv) region of an anti-FITC antibody, a co-stimulation domain and the co-stimulation domain is CD137 (4-1BB), and an activation signaling domain and the activation signaling domain is a T cell CD3ζ chain. It is well-known to the skilled artisan that an anti-FITC scFv and an anti-fluorescein scFv are equivalent terms.

In one embodiment, cytotoxic T lymphocytes can be genetically engineered to express CAR constructs by transfecting a population of the cytotoxic T lymphocytes with an expression vector encoding the CAR construct. Suitable methods for preparing a transduced population of T lymphocytes expressing a selected CAR construct are well-known to the skilled artisan, and are described in Sambrook et al., "Molecular Cloning: A Laboratory Manual", 3rd Edition, Cold Spring Harbor Laboratory Press, (2001), incorporated herein by reference.

In various embodiments, CAR T cells comprising a nucleic acid of SEQ ID NO:1 or 3 are provided. In another embodiment, CAR T cells comprising a polypeptide of SEQ ID NO:2 are provided. In another illustrative aspect, an isolated nucleic acid comprising SEQ ID NO:1 or 3 and encoding a chimeric antigen receptor is provided. In yet another embodiment, a chimeric antigen receptor polypeptide comprising SEQ ID NO:2 is provided. In another embodiment, a vector is provided comprising SEQ ID NO:1 or 3. In another aspect, a lentiviral vector is provided comprising SEQ ID NO:1 or 3. In another embodiment, SEQ ID NO:2 can comprise or consist of human or humanized amino acid sequences.

In each of these embodiments, variant nucleic acid sequences or amino acid sequences having at least about 80%, at least about 90%, at least about 95%, at least about 97%, at least about 98%, at least about 99%, or at least about 99.5% sequence identity to SEQ ID NO:1, SEQ ID NO:2, or SEQ ID NO:3 are contemplated. In another embodiment, the nucleic acid sequence can be a variant nucleic acid sequence having at least about 80%, at least about 90%, at least about 95%, at least about 97%, at least about 98%, at least about 99%, or at least about 99.5% sequence identity to SEQ ID NO:1 or 3 as long as the variant sequence encodes a polypeptide of SEQ ID NO:2. In another embodiment, the nucleic acid or amino acid sequence can be a variant nucleic acid or amino acid sequence having at least about 80%, at least about 90%, at least about 95%, at least about 97%, at least about 98%, at least about 99%, or at least about 99.5% sequence identity to SEQ ID NO:1 or SEQ ID NO:2 or SEQ ID NO:3 along a stretch of 200 nucleic acids or 200 amino acids of SEQ ID NO:1 or SEQ ID NO:2 or SEQ ID NO:3. Determination of percent identity or similarity between sequences can be done, for example, by using the GAP program (Genetics Computer Group, software; now available via Accelrys on http://www.accelrys.com), and alignments can be done using, for example, the ClustalW algorithm (VNTI software, InforMax Inc.). A sequence database can be searched using the nucleic acid or amino acid sequence of interest. Algorithms for database searching are typically based on the BLAST software (Altschul et al., 1990). In some embodiments, the percent identity can be determined along the full-length of the nucleic acid or amino acid sequence.

Also within the scope of the invention are nucleic acids complementary to the nucleic acid represented by SEQ ID NO:1 or 3, and those that hybridize to the nucleic acid represented by SEQ ID NO:1 or 3 or those that hybridize to its complement under highly stringent conditions. In accordance with the invention "highly stringent conditions" means hybridization at 65° C. in 5×SSPE and 50% formamide, and washing at 65° C. in 0.5×SSPE. Conditions for high stringency, low stringency and moderately stringent hybridization are described in Sambrook et al., "Molecular Cloning: A Laboratory Manual", 3rd Edition, Cold Spring Harbor Laboratory Press, (2001), incorporated herein by reference. In some illustrative aspects, hybridization occurs along the full-length of the nucleic acid.

In one embodiment, the cytotoxic T lymphocytes used to prepare the CAR T cells, used in the methods described herein, can be autologous cells, although heterologous cells can also be used, such as when the patient being treated has received high-dose chemotherapy or radiation treatment to destroy the patient's immune system. In one embodiment, allogenic cells can be used.

In one aspect, the cytotoxic lymphocytes T can be obtained from a patient by means well-known in the art. For example, cytotoxic T cells can be obtained by collecting peripheral blood from the patient, subjecting the blood to Ficoll density gradient centrifugation, and then using a negative T cell isolation kit (such as EasySep™ T Cell Isolation Kit) to isolate a population of cytotoxic T cells from the peripheral blood. In one illustrative embodiment, the population of cytotoxic T lymphocytes need not be pure and may contain other cells such as other T cells, monocytes, macrophages, natural killer cells, and B cells. In one aspect, the population being collected can comprise at least about 90% of the selected cell type, at least about 91%, 92%, 93%, 94%, 95%, 96%, 97%, 98%, 99%, or 100% of the selected cell type.

In one embodiment, after the cytotoxic T lymphocytes are obtained, the cells are cultured under conditions that promote the activation of the cells. In this embodiment, the culture conditions may be such that the cells can be administered to a patient without concern for reactivity against components of the culture medium. For example, the culture conditions may not include bovine serum products, such as bovine serum albumin. In one illustrative aspect, the activation can be achieved by introducing known activators into the culture medium, such as anti-CD3 antibodies in the case of cytotoxic T cells. Other suitable activators include anti-CD28 antibodies. In one aspect, the population of lymphocytes can be cultured under conditions promoting activation for about 1 to about 4 days. In one embodiment, the appropriate level of activation can be determined by cell size, proliferation rate, or activation markers determined by flow cytometry.

In one illustrative embodiment, after the population of cytotoxic T lymphocytes has been cultured under conditions promoting activation, the cells can be transfected with an expression vector encoding a CAR. Suitable vectors and transfection methods are described above. In one aspect, after transfection, the cells can be immediately administered to the patient or the cells can be cultured for at least about 1, 2, 3, 4, 5, 6, 7, 8, 9, 10, 11, 12, 13, 14, 15, 16, 17, 18 or more days, or between about 5 and about 12 days, between about 6 and about 13 days, between about 7 and about 14 days, or between about 8 and about 15 days, for example, to allow time for the cells to recover from the transfection. Suitable culture conditions can be similar to the conditions under which the cells were cultured for activation either with or without the agent that was used to promote activation.

Thus, as described above, in one illustrative aspect, the methods of treatment described herein can further comprise 1) obtaining a population of autologous or heterologous cytotoxic T lymphocytes, 2) culturing the T lymphocytes under conditions that promote the activation of the cells, and 3) transfecting the lymphocytes with an expression vector encoding a CAR to form CAR T cells.

In one illustrative embodiment, when the cells have been transfected and activated a composition comprising the CAR T cells can be prepared and administered to the patient. In one embodiment, culture media that lacks any animal products, such as bovine serum, can be used. In another embodiment, tissue culture conditions typically used by the skilled artisan to avoid contamination with bacteria, fungi and *mycoplasma* can be used. In an exemplary embodiment, prior to being administered to a patient, the cells are pelleted, washed, and resuspended in a pharmaceutically acceptable carrier or diluent. Exemplary compositions comprising CAR-expressing cytotoxic T lymphocytes include compositions comprising the cells in sterile 290 mOsm saline, in infusible cryomedia (containing Plasma-Lyte A, dextrose, sodium chloride injection, human serum albumin and DMSO), in 0.9% NaCl with 2% human serum albumin, or in any other sterile 290 mOsm infusible materials. Alternatively, depending on the identity of the culture medium, the CAR T cells can be administered in the culture media as the composition, or concentrated and resuspended in the culture medium before administration. The CAR T cell composition can be administered to the patient via any suitable means, such as parenteral administration, e.g., intradermally, subcutaneously, intramuscularly, intraperitoneally, intravenously, or intrathecally.

In one aspect, the total number of CAR T cells and the concentration of the cells in the composition administered to the patient will vary depending on a number of factors including the type of cytotoxic T lymphocytes being used, the binding specificity of the CAR, the identity of the targeting moiety and the small molecule ligand, the identity of the cancer, the location of the cancer in the patient, the means used to administer the compositions to the patient, and the health, age and weight of the patient being treated. However, suitable compositions comprising transduced CAR T cells include those having a volume of between about 5 ml and about 200 ml, containing from about $1 \times 10^5$ to about $1 \times 10^{15}$ transduced CAR T cells. Typical compositions comprise a volume of between about 10 ml and about 125 ml, containing from about $1 \times 10^7$ to about $1 \times 10^{10}$ CAR T cells. An exemplary composition comprises about $1 \times 10^9$ CAR T cells in a volume of about 100 ml. In one aspect, a single dose or multiple doses of the CAR T cells can be administered to the patient.

In various embodiments, the cancer to be treated is a carcinoma, a sarcoma, a lymphoma, a melanoma, a mesothelioma, a nasopharyngeal carcinoma, a leukemia, an adenocarcinoma, or a myeloma. In other embodiments, the cancer may be lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, cancer of the urethra, prostate cancer, chronic leukemia, acute leukemia, a lymphocytic lymphoma, pleural mesothelioma, cancer of the bladder, Burkitt's lymphoma, cancer of the ureter, cancer of the kidney, renal cell carcinoma, carcinoma of the renal pelvis, a neoplasm of the central nervous system (CNS), primary CNS lymphoma, a spinal axis tumor, a brain stem glioma, a pituitary adenoma, or an adenocarcinoma of the gastroesophageal junction.

In some aspects of these embodiments, the cancer is a folate receptor expressing cancer. In some aspects of these embodiments, the cancer is an endometrial cancer, a non-small cell lung cancer, an ovarian cancer, or a triple-negative breast cancer. In another embodiment, the cancer being imaged is a tumor. In another embodiment, the cancer is malignant.

The compound, or pharmaceutically acceptable salt thereof, the first conjugate, or pharmaceutically acceptable salt thereof, the second conjugate, or pharmaceutically acceptable salt thereof, or CAR T cell composition described herein can be administered to the patient using any suitable method known in the art. As described herein, the term "administering" or "administered" includes all means of introducing the compound, or pharmaceutically acceptable salt thereof, the first conjugate, or pharmaceutically acceptable salt thereof, the second conjugate, or pharmaceutically acceptable salt thereof, or CAR T cell composition to the patient, including, but not limited to, oral (po), intravenous (iv), intramuscular (im), subcutaneous (sc), transdermal, and the like. The compound, or pharmaceutically acceptable salt thereof, the first conjugate, or pharmaceutically acceptable salt thereof, the second conjugate, or pharmaceutically acceptable salt thereof, described herein may be administered in unit dosage forms and/or formulations containing conventional nontoxic pharmaceutically-acceptable carriers, adjuvants, and vehicles.

In one aspect, the compound, or pharmaceutically acceptable salt thereof, the first conjugate, or pharmaceutically acceptable salt thereof, the second conjugate, or pharmaceutically acceptable salt thereof, or CAR T cell composition as described herein may be administered directly into the blood stream, into muscle, or into an internal organ. Suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. In one embodiment, means for parenteral administration include needle (including microneedle) injectors, needle-free injectors and infusion techniques.

In one illustrative aspect, parenteral formulations are typically aqueous solutions which may contain carriers or excipients such as salts, carbohydrates and buffering agents (preferably at a pH of from 3 to 9), but they may be more suitably formulated as a sterile non-aqueous solution or as a dried form to be used in conjunction with a suitable vehicle such as sterile, pyrogen-free water or sterile saline. In other embodiments, any of the liquid formulations described herein may be adapted for parenteral administration as described herein. The preparation under sterile conditions, by lyophilization to produce a sterile lyophilized powder for a parenteral formulation, may readily be accomplished using standard pharmaceutical techniques well-known to those skilled in the art. In one embodiment, the solubility of the compound, or pharmaceutically acceptable salt thereof, the first conjugate, or pharmaceutically acceptable salt thereof, the second conjugate, or pharmaceutically acceptable salt thereof, used in the preparation of a parenteral formulation may be increased by the use of appropriate formulation techniques, such as the incorporation of solubility-enhancing agents.

In some embodiments, the rate of tumor lysis can be regulated by adjusting the concentration of the first conjugate, or pharmaceutically acceptable salt thereof, the second conjugate, or pharmaceutically acceptable salt thereof, or both the first and second conjugate, or pharmaceutically acceptable salt thereof. Accordingly, by varying the concentration of the first conjugate, or pharmaceutically acceptable salt thereof, the second conjugate, or pharmaceutically acceptable salt thereof, or both the first and second conjugate, or pharmaceutically acceptable salt thereof, the cytotoxicity of the CAR T cell composition can be regulated. In some embodiments, the cytotoxicity of the CAR T cell composition can be balanced against the risk of tumor lysis syndrome, or cytokine release syndrome (CRS), as described herein by adjusting the concentration of the first conjugate, or pharmaceutically acceptable salt thereof, the second conjugate, or pharmaceutically acceptable salt thereof, or both the first and second conjugate, or pharmaceutically acceptable salt thereof. It will be appreciated that the concentration of the first conjugate, or pharmaceutically acceptable salt thereof, the second conjugate, or pharmaceutically acceptable salt thereof, or both the first and second conjugate, or pharmaceutically acceptable salt thereof can be a function of the amount or dose of the first conjugate, or pharmaceutically acceptable salt thereof, the second conjugate, or pharmaceutically acceptable salt thereof, or both the first and second conjugate, or pharmaceutically acceptable salt thereof that is administered to the patient.

The amount of the compound, or pharmaceutically acceptable salt thereof, the first conjugate, or pharmaceutically acceptable salt thereof, the second conjugate, or pharmaceutically acceptable salt thereof, to be administered to the patient can vary significantly depending on the cancer being treated, the route of administration of the compound, or pharmaceutically acceptable salt thereof, the first conjugate, or pharmaceutically acceptable salt thereof, the second conjugate, or pharmaceutically acceptable salt thereof, and the tissue distribution. The amount to be administered to a patient can be based on body surface area, mass, and physician assessment. In various embodiments, amounts to be administered can range, for example, from about 0.05 mg to about 30 mg, 0.05 mg to about 25.0 mg, about 0.05 mg to about 20.0 mg, about 0.05 mg to about 15.0 mg, about 0.05 mg to about 10.0 mg, about 0.05 mg to about 9.0 mg, about 0.05 mg to about 8.0 mg, about 0.05 mg to about 7.0 mg, about 0.05 mg to about 6.0 mg, about 0.05 mg to about 5.0 mg, about 0.05 mg to about 4.0 mg, about 0.05 mg to about 3.0 mg, about 0.05 mg to about 2.0 mg, about 0.05 mg to about 1.0 mg, about 0.05 mg to about 0.5 mg, about 0.05 mg to about 0.4 mg, about 0.05 mg to about 0.3 mg, about 0.05 mg to about 0.2 mg, about 0.05 mg to about 0.1 mg, about 0.01 mg to about 2 mg, about 0.3 mg to about 10 mg, about 0.1 mg to about 20 mg, or about 0.8 to about 3 mg. One of skill in the art will readily appreciate that the dose may vary within the various ranges provided above based on the factors noted above, and may be at the physician's discretion.

In other embodiments, the dose of the compound, or pharmaceutically acceptable salt thereof, the first conjugate, or pharmaceutically acceptable salt thereof, the second conjugate, or pharmaceutically acceptable salt thereof, can range, for example, from about 50 nmol/kg to about 3000 nmol/kg of patient body weight, about 50 nmol/kg to about 2000 nmol/kg, about 50 nmol/kg to about 1000 nmol/kg, about 50 nmol/kg to about 900 nmol/kg, about 50 nmol/kg to about 800 nmol/kg, about 50 nmol/kg to about 700 nmol/kg, about 50 nmol/kg to about 600 nmol/kg, about 50 nmol/kg to about 500 nmol/kg, about 50 nmol/kg to about 400 nmol/kg, about 50 nmol/kg to about 300 nmol/kg, about 50 nmol/kg to about 200 nmol/kg, about 50 nmol/kg to about 100 nmol/kg, about 100 nmol/kg to about 300 nmol/kg, about 100 nmol/kg to about 500 nmol/kg, about 100 nmol/kg to about 1000 nmol/kg, about 100 nmol/kg to about 2000 nmol/kg of patient body weight. In other embodiments, the dose may be about 100 nmol/kg, about 150 nmol/kg, about 200 nmol/kg, about 250 nmol/kg, about 300 nmol/kg, about 350 nmol/kg, about 400 nmol/kg, about 450 nmol/kg, about 500 nmol/kg, about 600 nmol/kg, about 700 nmol/kg, about 800 nmol/kg, about 900 nmol/kg, about 1000 nmol/kg, about 2000 nmol/kg, or about 3000 nmol/kg of patient body weight. In these embodiments, "kg" is kilograms of patient body weight. In one aspect, a single dose or multiple doses of the compound, or pharmaceutically acceptable salt thereof, the first conjugate, or pharmaceutically acceptable salt thereof, the second conjugate, or pharmaceutically acceptable salt thereof, may be administered to the patient.

In another embodiment, between about 20 ug/kg of patient body weight and about 3 mg/kg of patient body weight of the compound, or pharmaceutically acceptable salt thereof, the first conjugate, or pharmaceutically acceptable salt thereof, the second conjugate, or pharmaceutically acceptable salt thereof, is administered to the patient. In another aspect, amounts can be between about 0.2 mg/kg of patient body weight and about 0.4 mg/kg of patient body weight, or can be about 50 ug/kg of patient body weight. In one aspect, a single dose or multiple doses of the compound, or pharmaceutically acceptable salt thereof, the first conjugate, or pharmaceutically acceptable salt thereof, the second conjugate, or pharmaceutically acceptable salt thereof, may be administered to the patient.

In one embodiment, the small molecule ligand linked to the targeting moiety can be administered to the patient before the CAR T cell composition. In another embodiment, the small molecule ligand linked to the targeting moiety can be administered to the patient at the same time as the CAR T cell composition, but in different formulations. In yet another embodiment, the small molecule ligand linked to the targeting moiety can be administered to the patient after the CAR T cell composition.

In one illustrative aspect, the timing between the administration of CAR T cells and the small molecule linked to the targeting moiety may vary widely depending on factors that include the type of CAR T cells being used, the binding specificity of the CAR, the identity of the targeting moiety and the ligand, the identity of the cancer, the location in the patient of the cancer, the means used to administer to the patient the CAR T cells and the small molecule ligand linked to the targeting moiety, and the health, age, and weight of the patient. In one aspect, the small molecule ligand linked to the targeting moiety can be administered before or after the CAR T cells, such as within about 3, 6, 9, 12, 15, 18, 21, or 24 hours, or within about 0.5, 1, 1.5, 2, 2.5, 3, 4 5, 6, 7, 8, 9, 10 or more days.

In some embodiments, the rate of tumor lysis can be regulated by adjusting the rate of administration of the first conjugate, or pharmaceutically acceptable salt thereof, the second conjugate, or pharmaceutically acceptable salt thereof, or both the first and second conjugate, or pharmaceutically acceptable salt thereof. Accordingly, by varying the rate of administration of the first conjugate, or pharmaceutically acceptable salt thereof, the second conjugate, or pharmaceutically acceptable salt thereof, or both the first and second conjugate, or pharmaceutically acceptable salt thereof, the cytotoxicity of the CAR T cell composition can be regulated. In some embodiments, the cytotoxicity of the CAR T cell composition can be balanced against the risk of tumor lysis syndrome, or cytokine release syndrome (CRS), as described herein by adjusting the rate of administration of the first conjugate, or pharmaceutically acceptable salt thereof, the second conjugate, or pharmaceutically acceptable salt thereof, or both the first and second conjugate, or pharmaceutically acceptable salt thereof. It will be appreciated that the rate of administration of the first conjugate, or pharmaceutically acceptable salt thereof, the second conjugate, or pharmaceutically acceptable salt thereof, or both the first and second conjugate, or pharmaceutically acceptable salt thereof can be a function of any applicable dosing schedule known in the art. For example, the rate of administration can be a function of a dosing schedule that is based on continuous dosing, once per day dosing (a.k.a qd), twice per day dosing (a.k.a. bid), three times per day dosing (a.k.a. tid), twice per week (a.k.a. BIW), three times per week (a.k.a. TIW), once weekly, and the like. It will be appreciated that the dosing schedule selected for first conjugate, or pharmaceutically acceptable salt thereof, the second conjugate, or pharmaceutically acceptable salt thereof, or both the first and second conjugate, or pharmaceutically acceptable salt thereof can be applied in connection with the concentration to regulate the cytotoxicity of the CAR T cell composition. In some embodiments, the cytotoxicity of the CAR T cell composition can be balanced against the risk of tumor lysis syndrome, or cytokine release syndrome (CRS), as described herein by adjusting the dosing schedule in connection with the concentration of the first conjugate, or pharmaceutically acceptable salt thereof, the second conjugate, or pharmaceutically acceptable salt thereof, or both the first and second conjugate, or pharmaceutically acceptable salt thereof.

In one embodiment of the methods described herein, the cancer is imaged prior to administration to the patient of the compound, or pharmaceutically acceptable salt thereof, the first conjugate, or pharmaceutically acceptable salt thereof, the second conjugate, or pharmaceutically acceptable salt thereof, or prior to administration of the CAR T cell composition to the patient. In one illustrative embodiment, imaging occurs by PET imaging. In other illustrative embodiments imaging occurs by MRI imaging or SPECT/CT imaging. It is appreciated by one skilled in the art that the imaging method can be any suitable imaging method known in the art.

In any of the embodiments described herein, cytokine release resulting in 'off-target' toxicity in the patient may not occur even though CAR T cell toxicity to the cancer occurs. In any embodiment described herein, 'off-target' tissue toxicity may not occur in the patient even though CAR T cell toxicity to the cancer occurs. In any embodiment described herein, the cancer may comprise a tumor, and tumor size may be reduced in the patient, even though 'off-target' toxicity does not occur.

EXAMPLES

Example 1

Generation of Lentiviral Vector Encoding CAR Gene

An overlap PCR method was used to generate CAR constructs comprising scFv against fluorescein. scFV against fluorescein, 4M5.3 (Kd=270 fM, 762 bp) derived from anti-fluorescein (4-4-20) antibody was synthesized. Sequence encoding the human CD8α signal peptide (SP, 63 bp), the hinge, and transmembrane region (249 bp), the cytoplasmic domain of 4-1BB (CD137, 141 bp) and the CD3ζ chain (336 bp), as shown in FIG. 14A, were fused with the anti-fluorescein scFV by overlapping PCR. The resulting CAR construct (1551 bp) was inserted into EcoRI/NotI cleaved lentiviral expression vector pCDH-EF1-MCS-(PGK-GFP) (FIG. 14B, System Biosciences). The sequence of the CAR construct in lentiviral vector was confirmed by DNA sequencing.

An exemplary CAR nucleic acid coding sequence may comprise:

(SEQ ID NO: 1)
ATGGCCTTACCAGTGACCGCCTTGCTCCTGCCGCTGGCCTTGCTGCTCC

ACGCCGCCAGGCCGGATGTCGTGATGACCCAGACCCCCCTCAGCCTCCC

AGTGTCCCTCGGTGACCAGGCTTCTATTAGTTGCAGATCCAGCCAGTCC

CTCGTGCACTCTAACGGTAATACCTACCTGAGATGGTATCTCCAGAAGC

CCGGACAGAGCCCTAAGGTGCTGATCTACAAAGTCTCCAACCGGGTGTC

TGGAGTCCCTGACCGCTTCTCAGGGAGCGGTTCCGGCACCGACTTCACC

CTGAAGATCAACCGGGTGGAGGCCGAAGACCTCGGCGTCTATTTCTGCT

CTCAGAGTACACATGTGCCCTGGACCTTCGGCGGAGGGACCAAGCTGGA

GATCAAAAGCTCCGCAGACGATGCCAAGAAAGATGCCGCTAAGAAAGAC

GATGCTAAGAAAGACGATGCAAAGAAAGACGGTGGCGTGAAGCTGGATG

AAACCGGAGGAGGTCTCGTCCAGCCAGGAGGAGCCATGAAGCTGAGTTG

CGTGACCAGCGGATTCACCTTTGGGCACTACTGGATGAACTGGGTGCGA

CAGTCCCCAGAGAAGGGGCTCGAATGGGTCGCTCAGTTCAGGAACAAAC

CCTACAATTATGAGACATACTATTCAGACAGCGTGAAGGGCAGGTTTAC

TATCAGTAGAGACGATTCCAAATCTAGCGTGTACCTGCAGATGAACAAT

CTCAGGGTCGAAGATACAGGCATCTACTATTGCACAGGGGCATCCTATG

GTATGGAGTATCTCGGTCAGGGGACAAGCGTCACAGTCAGTTTCGTGCC

GGTCTTCCTGCCAGCGAAGCCCACCACGACGCCAGCGCCGCGACCACCA

ACACCGGCGCCCACCATCGCGTCGCAGCCCCTGTCCCTGCGCCCAGAGG

CGTGCCGGCCAGCGGCGGGGGCGCAGTGCACACGAGGGGGCTGGACTT

CGCCTGTGATATCTACATCTGGGCGCCCTTGGCCGGGACTTGTGGGGTC

CTTCTCCTGTCACTGGTTATCACCCTTTACTGCAACCACAGGAACCGTT

TCTCTGTTGTTAAACGGGGCAGAAAGAAACTCCTGTATATATTCAAACA

ACCATTTATGAGACCAGTACAAACTACTCAAGAGGAAGATGGCTGTAGC

TGCCGATTTCCAGAAGAAGAAGAAGGAGGATGTGAACTGAGAGTGAAGT

TCAGCAGGAGCGCAGACGCCCCCGCGTACCAGCAGGGCCAGAACCAGCT

CTATAACGAGCTCAATCTAGGACGAAGAGAGGAGTACGATGTTTTGGAC

AAGAGACGTGGCCGGGACCCTGAGATGGGGGGAAAGCCGAGAAGGAAGA

ACCCTCAGGAAGGCCTGTACAATGAACTGCAGAAAGATAAGATGGCGGA

GGCCTACAGTGAGATTGGGATGAAAGGCGAGCGCCGGAGGGGCAAGGGG

CACGATGGCCTTTACCAGGGTCTCAGTACAGCCACCAAGGACACCTACG

ACGCCCTTCACATGCAGGCCCTGCCCCCTCGCTAA.

In the exemplary nucleic acid sequence shown above, the first ATG is the start codon. An exemplary CAR amino acid sequence may comprise:

(SEQ ID NO: 2)
MALPVTALLLPLALLLHAARPDVVMTQTPLSLPVSLGDQASISCRSSQS
LVHSNGNTYLRWYLQKPGQSPKVLIYKVSNRVSGVPDRFSGSGSGTDFT
LKINRVEAEDLGVYFCSQSTHVPWTFGGGTKLEIKSSADDAKKDAAKKD
DAKKDDAKKDGGVKLDETGGGLVQPGGAMKLSCVTSGFTFGHYWMNWVR
QSPEKGLEWVAQFRNKPYNYETYYSDSVKGRFTISRDDSKSSVYLQMNN
LRVEDTGIYYCTGASYGMEYLGQGTSVTVSFVPVFLPAKPTTTPAPRPP
TPAPTIASQPLSLRPEACRPAAGGAVHTRGLDFACDIYIWAPLAGTCGV
LLLSLVITLYCNHRNRFSVVKRGRKKLLYIFKQPFMRPVQTTQEEDGCS
CRFPEEEEGGCELRVKFSRSADAPAYQQGQNQLYNELNLGRREEYDVLD
KRRGRDPEMGGKPRRKNPQEGLYNELQKDKMAEAYSEIGMKGERRRGKG
HDGLYQGLSTATKDTYDALHMQALPPR

An exemplary insert may comprise:

(SEQ ID NO: 3)
GCCACCATGGCCTTACCAGTGACCGCCTTGCTCCTGCCGCTGGCCTTGC
TGCTCCACGCCGCCAGGCCGGATGTCGTGATGACCCAGACCCCCCTCAG
CCTCCCAGTGTCCCTCGGTGACCAGGCTTCTATTAGTTGCAGATCCAGC
CAGTCCCTCGTGCACTCTAACGGTAATACCTACCTGAGATGGTATCTCC
AGAAGCCCGGACAGAGCCCTAAGGTGCTGATCTACAAAGTCTCCAACCG
GGTGTCTGGAGTCCCTGACCGCTTCTCAGGGAGCGGTTCCGGCACCGAC
TTCACCCTGAAGATCAACCGGGTGGAGGCCGAAGACCTCGGCGTCTATT
TCTGCTCTCAGAGTACACATGTGCCCTGGACCTTCGGCGGAGGGACCAA
GCTGGAGATCAAAAGCTCCGCAGACGATGCCAAGAAAGATGCCGCTAAG
AAAGACGATGCTAAGAAAGACGATGCAAAGAAAGACGGTGGCGTGAAGC
TGGATGAAACCGGAGGAGGTCTCGTCCAGCCAGGAGGAGCCATGAAGCT
GAGTTGCGTGACCAGCGGATTCACCTTTGGGCACTACTGGATGAACTGG
GTGCGACAGTCCCCAGAGAAGGGGCTCGAATGGGTCGCTCAGTTCAGGA
ACAAACCCTACAATTATGAGACATACTATTCAGACAGCGTGAAGGGCAG
GTTTACTATCAGTAGAGACGATTCCAAATCTAGCGTGTACCTGCAGATG
AACAATCTCAGGGTCGAAGATACAGGCATCTACTATTGCACAGGGGCAT
CCTATGGTATGGAGTATCTCGGTCAGGGGACAAGCGTCACAGTCAGTTT
CGTGCCGGTCTTCCTGCCAGCGAAGCCCACCACGACGCCAGCGCCGCGA
CCACCAACACCGGCGCCCACCATCGCGTCGCAGCCCCTGTCCCTGCGCC
CAGAGGCGTGCCGGCCAGCGGCGGGGGCGCAGTGCACACGAGGGGGCT
GGACTTCGCCTGTGATATCTACATCTGGGCGCCCTTGGCCGGGACTTGT
GGGGTCCTTCTCCTGTCACTGGTTATCACCCTTTACTGCAACCACAGGA
ACCGTTTCTCTGTTGTTAAACGGGGCAGAAAGAAACTCCTGTATATATT
CAAACAACCATTTATGAGACCAGTACAAACTACTCAAGAGGAAGATGGC

TGTAGCTGCCGATTTCCAGAAGAAGAAGAAGGAGGATGTGAACTGAGAG
TGAAGTTCAGCAGGAGCGCAGACGCCCCCGCGTACCAGCAGGGCCAGAA
CCAGCTCTATAACGAGCTCAATCTAGGACGAAGAGAGGAGTACGATGTT
TTGGACAAGAGACGTGGCCGGACCCTGAGATGGGGGAAAGCCGAGAA
GGAAGAACCCTCAGGAAGGCCTGTACAATGAACTGCAGAAAGATAAGAT
GGCGGAGGCCTACAGTGAGATTGGGATGAAAGGCGAGCGCCGGAGGGGC
AAGGGGCACGATGGCCTTTACCAGGGTCTCAGTACAGCCACCAAGGACA
CCTACGACGCCCTTCACATGCAGGCCCTGCCCCCTCGCTAA

In the exemplary insert shown above, the first GCCACC sequence may be a restriction enzyme cleavage site, followed by the ATG start codon. An exemplary insert amino acid sequence may comprise:

(SEQ ID NO: 4)
ATMALPVTALLLPLALLLHAARPDVVMTQTPLSLPVSLGDQASISCRSS
QSLVHSNGNTYLRWYLQKPGQSPKVLIYKVSNRVSGVPDRFSGSGSGTD
FTLKINRVEAEDLGVYFCSQSTHVPWTFGGGTKLEIKSSADDAKKDAAK
KDDAKKDDAKKDGGVKLDETGGGLVQPGGAMKLSCVTSGFTFGHYWMNW
VRQSPEKGLEWVAQFRNKPYNYETYYSDSVKGRFTISRDDSKSSVYLQM
NNLRVEDTGIYYCTGASYGMEYLGQGTSVTVSFVPVFLPAKPTTTPAPR
PPTPAPTIASQPLSLRPEACRPAAGGAVHTRGLDFACDIYIWAPLAGTC
GVLLLSLVITLYCNHRNRFSVVKRGRKKLLYIFKQPFMRPVQTTQEEDG
CSCRFPEEEEGGCELRVKFSRSADAPAYQQGQNQLYNELNLGRREEYDV
LDKRRGRDPEMGGKPRRKNPQEGLYNELQKDKMAEAYSEIGMKGERRRG
KGHDGLYQGLSTATKDTYDALHMQALPPR

Example 2

Production of Lentivius Containing CAR Gene for Human T Cell Transduction

To prepare lentiviral virus containing an anti-fluorescein single chain fragment variable (scFv) CAR, a 293TN packaging cell line was co-transfected with the lentiviral vector encoding anti-fluorescein scFv CAR and a 2nd generation of a mixture of packaging plasmids (Cellecta). After 24 and 48 hours of transfection, supernatants containing the lentivirus with the CAR gene were harvested and virus particles were concentrated by the standard polyethylene glycol virus concentration method (Clontech) for future transduction with human T cells.

Example 3

Isolation of Human T Cells from Human PBMC

T cells were isolated from human peripheral blood mononuclear cells (PBMC) by Ficoll density gradient centrifugation (GE Healthcare Lifesciences). After washing away remaining Ficoll solution, T cells were isolated by using an EasySep™ Human T Cell Isolation Kit (STEM CELL technologies). Purified T cells were cultured in TexMACS™ medium (Miltenyi Biotech Inc) with 1% penicillin and streptomycin sulfate in the presence of human IL-2 (100

IU/mL, Miltenyi Biotech Inc). T cells were cultured at density of 1×10⁶ cells/mL in multi-well plates. T cells were split and re-feed every 2-3 days.

Example 4

Transduction of Human T Cells

Isolated T cells were activated with Dynabeads coupled with anti-CD3/CD28 antibodies (Life Technologies) for 12-24 hours in the presence of human IL-2 (100 IU/mL), then transduced with lentivirus encoding an anti-fluorescein CAR gene. Cells were harvested after 72 hours and the expression of CAR on transduced T cells was identified by measuring GFP fluorescent cells using flow cytometry. As shown in FIG. 15A, non-transduced T cells do not show GFP expression. As shown in FIG. 15B, transduced T-cells express GFP.

Example 5

Synthesis of FITC-Folate

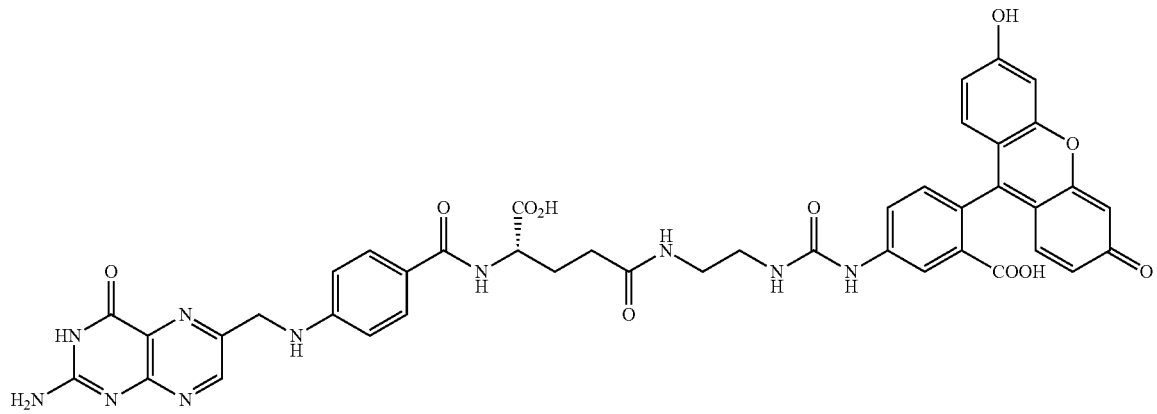 [SMILES: Nc1nc2ncc(CNc3ccc(C(=O)N[C@@H](CCC(=O)NCCNC(=O)Nc4ccc(-c5c6ccc(=O)cc-6oc6cc(O)ccc56)c(C(=O)O)c4)C(=O)O)cc3)nc2c(=O)[nH]1]

Folate-γ-ethylenediamine was coupled to fluorescein isothiocyanate (FITC) isomer I (Sigma-Aldrich) in anhydrous dimethylsulfoxide (DMF) in the presence of tetramethylguanidine and diisopropylamine. The crude product was loaded onto an Xterra RP18 preparative HPLC column (Waters) and eluted with gradient conditions starting with 99% 5 mM sodium phosphate (mobile phase A, pH 7.4) and 1% acetonitrile (mobile phase B) and reaching 90% A and 10% B in 10 min at a flow rate of 20 mL/min. Under these conditions, the FITC-folate main peak typically eluted at 27-50 min. The quality of the FITC-folate fraction was monitored by analytical reverse-phase HPLC with a UV detector. Fractions with greater than 98.0% purity (LCMS) were lyophilized to obtain the final FITC-folate product.

Example 6

Synthesis of FITC-PEG12-Folate

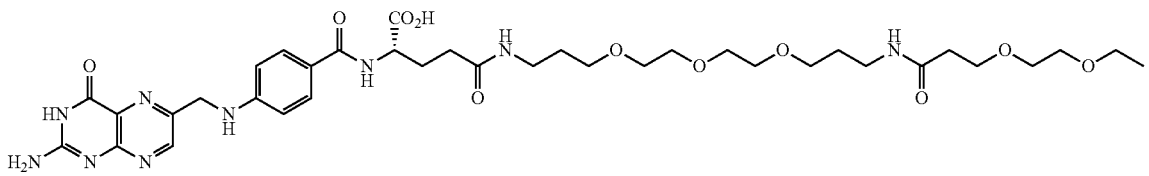

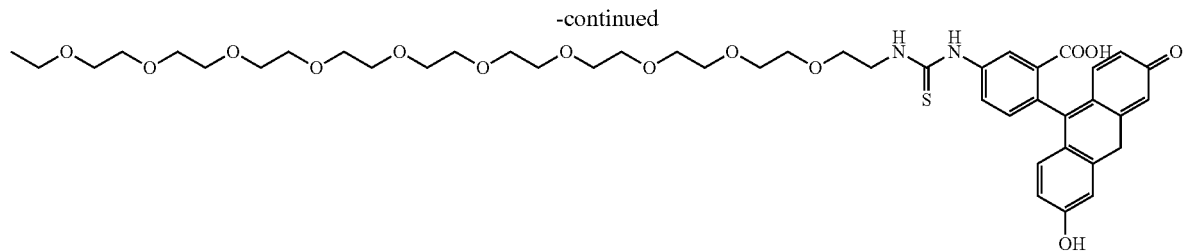

Universal polyethylene glycol (PEG) Nova Tag™ resin (0.2 g) was loaded into a peptide synthesis vessel and washed with isopropyl alcohol (i-PrOH) (3×10 mL) and dimethylformamide (DMF, 3×10 mL). 9-fluorenylmethoxycarbonyl (Fmoc) deprotection was carried out using 20% piperidine in DMF (3×10 mL). Kaiser tests were performed to assess reaction progress. To the vessel was then introduced a solution of Fmoc-L-glutamic acid 5-tert-butyl ester (Fmoc-Glu-(O-t-Bu)-OH) (23.5 mg) in DMF, N,N-diisopropylethylamine (i-Pr$_2$NEt) (4 equiv), and benzotriazol-1-yl-oxytripyrrolidinophosphonium hexafluorophosphate (PyBOP) (2 equiv). Fmoc deprotection was carried out using 20% piperidine in DMF (3×10 mL). To the vessel was then introduced a solution of N$^{10}$-TFA-Pte-OH (22.5 mg), DMF, i-Pr$_2$NEt (4 equiv), and PyBOP (2 equiv). Argon was bubbled for 2 h, and the resin was washed with DMF (3×3 mL) and i-PrOH (3×3 mL). After swelling the resin in dichloromethane (DCM), a solution of 1M hydroxybenzotriazole (HOBT) in DCM/trifluoroethane (TFE) (1:1) (2×3 mL) was added. Argon was bubbled for 1 h, the solvent was removed, and the resin was washed with DMF (3×3 mL) and i-PrOH (3×3 mL). After swelling the resin in DMF, a solution of Fmoc-NH-(PEG)$_{12}$-COOH (46.3 mg) in DMF, i-Pr$_2$NEt (4 equiv), and PyBOP (2 equiv) was added. Argon was bubbled for 2 h, and the resin was washed with DMF (3×3 mL) and i-PrOH (3×3 mL). Fmoc deprotection was carried out using 20% piperidine in DMF (3×10 mL). Kaiser tests were performed to assess reaction progress. To the vessel was then introduced a solution of FITC (Life Technologies 21.4 mg) in DMF and i-Pr$_2$NEt (4 equiv), then Argon was bubbled for 2 h, and the resin was washed with DMF (3×3 mL) and i-PrOH (3×3 mL). Then to the vessel was added 2% NH$_2$NH$_2$ in DMF (2×2 mL). The final compound was cleaved from the resin using a TFA:H$_2$O:triisopropylsilane (TIS) (95:2.5:2.5) (Cleavage Solution) and concentrated under vacuum. The concentrated product was precipitated in Et$_2$O and dried under vacuum. The crude product was purified using preparative RP-HPLC (mobile phase: A=10 mM ammonium acetate pH=7, B=ACN; method: 0% B to 30% B in 30 min at 13 mL/min). The pure fractions were pooled and freeze-dried, providing the FITC-PEG12-Folate.

Example 7

Synthesis of FITC-PEG20-Folate

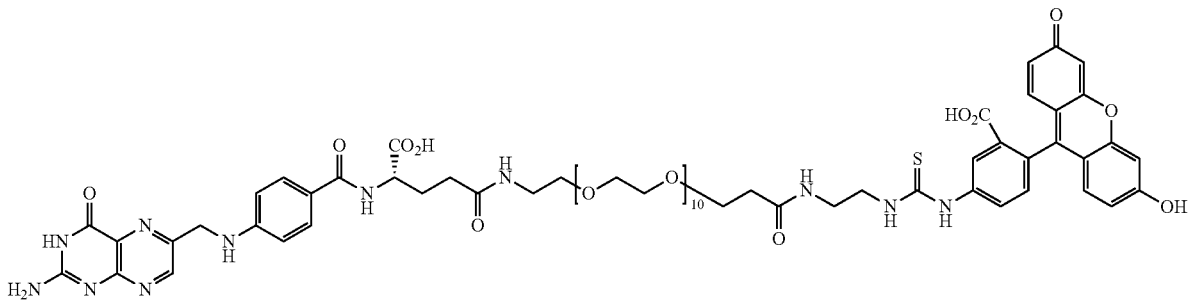

Ethylenediamine, polymer-bound (200-400 mesh)-resin (50 mg) was loaded into a peptide synthesis vessel and swollen with DCM (3 mL) followed by DMF (3 mL). To the vessel was then introduced the Fmoc-PEG$_{20}$-COOH solution (131 mg, 1.0 equiv) in DMF, i-Pr$_2$NEt (6.0 equiv), and PyBOP (4.0 equiv). Argon was bubbled for 6 h, the coupling solution was drained, and the resin was washed with DMF (3×10 mL) and i-PrOH (3×10 mL). Kaiser tests were performed to assess reaction progress. Fmoc deprotection was carried out using 20% piperidine in DMF (3×10 mL), before each amino acid coupling. The above sequence was repeated to complete the reaction with Fmoc-Glu-OtBu (72 mg, 2.0 equiv) and Tfa.Pteroic-acid (41 mg, 1.2 equiv) coupling steps. The resin was washed with 2% hydrazine in DMF 3×10 mL (5 min) to cleave the trifluoro-acetyl protecting group on pteroic acid and washed with i-PrOH (3×10 mL) followed by DMF (3×10 mL). The resin was dried under argon for 30 min. The folate-peptide was cleaved from the resin using the Cleavage Solution. 10 mL of the cleavage mixture was introduced and argon was bubbled for 1.5 h. The cleavage mixture was drained into a clean flask. The resin was washed 3 times with more cleavage mixture. The combined mixture was concentrated under reduced pressure to a smaller volume (~5 mL) and precipitated in ethyl ether.

The precipitate was collected by centrifugation, washed with ethyl ether (3 times) and dried under high vacuum. The dried Folate-PEG$_{20}$-EDA (1.0 equiv) was treated with FITC (50 mg, 1.5 equiv) in DMSO and DIPEA at room temperature. Progress of the reaction monitored by LCMS. After 8 h the starting material was consumed to give the product. The crude reaction mixture was purified by preparative HPLC, (mobile phase A=10 mM Ammonium Acetate, pH=7; Organic phase B=Acetonitrile; Method: 0% B to 30% B in 35 minutes at 13 mL/min) and provided FITC-PEG20-Folate in 60% yield.

Example 8

Synthesis of FITC-PEG108-Folate

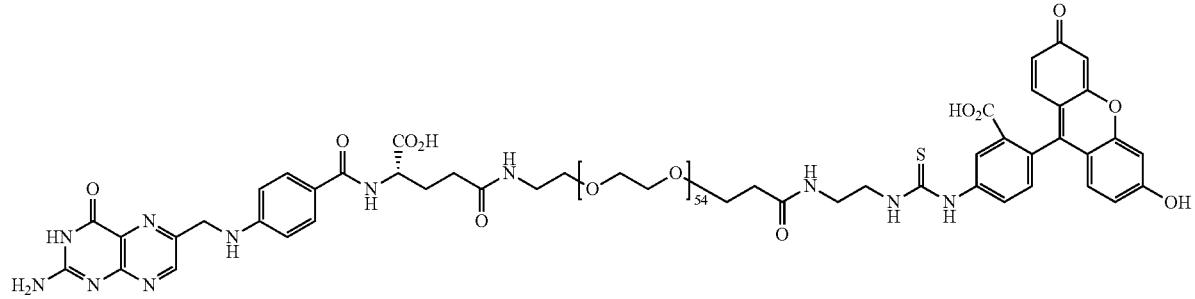

Ethylenediamine, polymer-bound (200-400 mesh)-resin (50 mg) was loaded in a peptide synthesis vessel and swollen with DCM (3 mL) followed by DMF (3 mL). To the vessel was then introduced the Fmoc-PEG$_{36}$-COOH solution (161 mg, 1.0 equiv) in DMF, i-Pr$_2$NEt (6.0 equiv), and PyBOP (4.0 equiv). Argon was bubbled for 6 h, the coupling solution was drained, and the resin was washed with DMF (3×10 mL) and i-PrOH (3×10 mL). Kaiser tests were performed to assess reaction progress. Fmoc deprotection was carried out using 20% piperidine in DMF (3×10 mL), before each amino acid coupling. The above sequence was repeated to complete reaction with 2×Fmoc-PEG$_{36}$-COOH (161 mg, 1.0 equiv), Fmoc-Glu-OtBu (72 mg, 2.0 equiv) and Tfa.Pteroic-acid (41.0 mg, 1.2 equiv) coupling steps. At the end the resin was washed with 2% hydrazine in DMF 3×10 mL (5 min) to cleave the trifluoro-acetyl protecting group on pteroic acid and washed with i-PrOH (3×10 mL) followed by DMF (3×10 mL). The resin was dried under argon for 30 min. Folate-peptide was cleaved from the resin using the Cleavage Solution. 10 mL of the cleavage mixture was introduced and argon was bubbled for 1.5 h. The cleavage mixture was drained into a clean flask. The resin was washed 3× with more Cleavage Solution. The combined mixture was concentrated under reduced pressure to a smaller volume (~5 mL) and precipitated in ethyl ether.

The precipitate was collected by centrifugation, washed with ethyl ether (3×) and dried under high vacuum. The dried Folate-PEG$_{108}$-EDA (1.0 equiv) was treated with FITC (50 mg, 1.5 equiv) in DMSO and DIPEA at room temperature. Reaction progress was monitored by LCMS.

After 10 h starting material was consumed to give the product. The crude reaction mixture was purified by preparative HPLC, (mobile phase A=10 mM Ammonium Acetate, pH=7; Organic phase B=Acetonitrile; Method: 0% B to 30% B in 35 minutes at 13 mL/min) and provided FITC-PEG108-Folate in 64% yield.

Example 9

Synthesis of FITC-DUPA

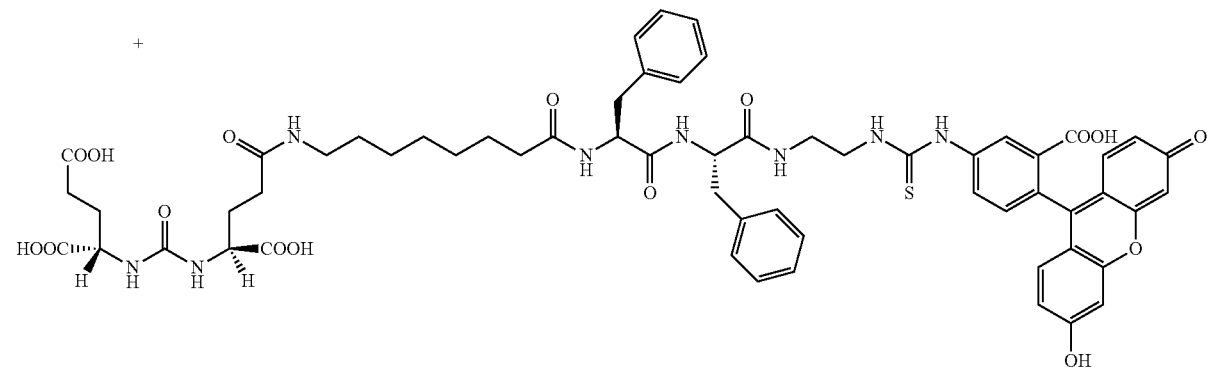 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

DUPA-FITC was synthesized by solid phase methodology as follows. Universal Nova Tag™ resin (50 mg, 0.53 mM) was swollen with DCM (3 mL) followed by DMF 3 mL). A solution of 20% piperidine in DMF (3×3 mL) was added to the resin, and argon was bubbled for 5 min. The resin was washed with DMF (3×3 mL) and isopropyl alcohol (i-PrOH, 3×3 mL). After swelling the resin in DMF, a solution of DUPA-(OtBu)-OH (1.5 equiv), HATU (2.5 equiv), and i-Pr$_2$NEt (4.0 equiv) in DMF was added. Argon was bubbled for 2 h, and resin was washed with DMF (3×3 mL) and i-PrOH (3×3 mL). After swelling the resin in DCM, a solution of 1 M HOBt in DCM/TFE (1:1) (2×3 mL) was added. Argon was bubbled for 1 h, the solvent was removed and resin was washed with DMF (3×3 mL) and i-PrOH (3×3 mL). After swelling the resin in DMF, a solution of Fmoc-Phe-OH (2.5 equiv), HATU (2.5 equiv) and DIPEA (4.0 equiv) in DMF was added. Argon was bubbled for 2 h, and the resin was washed with DMF (3×3 mL) and i-PrOH (3×3 mL). The above sequence was repeated for 2 more coupling steps for addition of 8-aminooctanoic acid and fluorescein isothiocyanate or rhodamine B isothiocyanate. The final compound was cleaved from the resin using the Cleavage Solution and concentrated under vacuum. The concentrated product was precipitated in diethyl ether and dried under vacuum. The crude product was purified using preparative RP-HPLC [λ, =488 nm; solvent gradient: 1% B to 80% B in 25 min, 80% B wash 30 mM run; A=10 mM $NH_4OAc$, pH=7; B=acetonitrile (ACN)]. ACN was removed under vacuum, and purified fractions were freeze-dried to yield FITC-DUPA as a brownish-orange solid. RP-HPLC: tR=8.0 min (A=10 mM $NH_4OAc$, pH=7.0; B=ACN, solvent gradient: 1% B to 50% B in 10 min, 80% B wash 15 min run). $^1$H NMR (DMSO-d6/$D_2O$): δ 0.98-1.27 (ms, 9H); 1.45 (b, 3H); 1.68-1.85 (ms, 11H); 2.03 (m, 8H); 2.6-3.44 (ms, 12H); 3.82 (b, 2H); 4.35 (m, 1H); 6.53 (d, J=8.1 Hz, 2H); 6.61 (dd, J=5.3, 3.5 Hz, 2H); 6.64 (s, 2H); 7.05 (d, J=8.2 Hz, 2H), 7.19 (m, 5H); 7.76 (d, J=8.0 Hz, 1H); 8.38 (s, 1H). HRMS (ESI) (m/z): $(M+H)^+$ calcd for $C_{51}H_{59}N_7O_{15}S$, 1040.3712, found, 1040.3702. UV/vis: λ, max=491 nm.

Example 10

Synthesis of FITC-PEG12-DUPA 1,2-Diaminoethane trityl-resin (0.025 g) was loaded into a peptide synthesis vessel and washed with i-PrOH (3×10 mL), followed by DMF (3×10 mL). To the vessel was then introduced a solution of Fmoc-NH-$(PEG)_{12}$-COOH (42.8 mg) in DMF, i-$Pr_2$NEt (2.5 equiv), and PyBOP (2.5 equiv). The resulting solution was bubbled with Ar for 1 h, the coupling solution was drained, and the resin washed with DMF (3×10 mL) and i-PrOH (3×10 mL). Kaiser tests were performed to assess reaction progress. Fmoc deprotection was carried out using 20% piperidine in DMF (3×10 mL). This procedure was repeated to complete the all coupling steps (2×1.5 equiv of Fmoc-Phe-OH and 1.5 equiv of 8-aminooctanoic acid and 1.2 equiv of DUPA were used on each of their respective coupling steps). After the DUPA coupling, the resin was washed with DMF (3×10 mL) and i-PrOH (3×10 mL) and dried under reduced pressure. The peptide was cleaved from the resin in the peptide synthesis vessel using the Cleavage Solution. 15 mL of the Cleavage Solution was added to the peptide synthesis vessel, and the reaction was bubbled under Ar for 15 min. The resin was treated with two additional 10 mL quantities of the Cleavage Solution for 5 min each. The cleavage mixture was concentrated to about 5 mL and precipitated with ethyl ether. The precipitate was collected by centrifugation, washed with ethyl ether (3×), and dried under high vacuum, resulting in the recovery of crude material. To a stirred solution of the crude DUPA-$(PEG)_{12}$-EDA (10 mg) and FITC (5.6 mg) in dimethylsulfoxide (DMSO, 1 mL) was added i-$Pr_2$NEt (5 equiv) at room temperature and stirred for 6 h under argon.

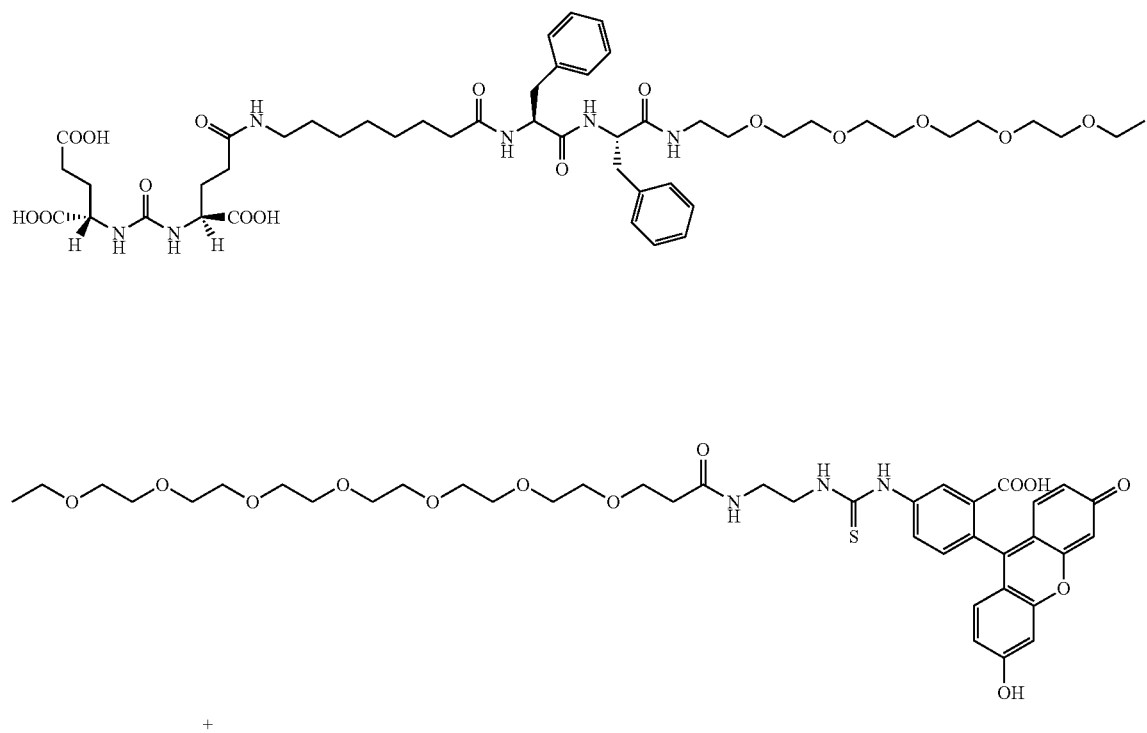

+

The reaction was monitored by LCMS and purified by preparative HPLC (mobile phase: A=10 mM ammonium acetate pH=7, B=ACN; method: 0% B to 50% B in 30 min at 13 mL/min). The purified fractions were pooled and freeze-dried, providing the FITC-PEG12-DUPA.

Example 11

Synthesis of FITC-PEG11-NK1

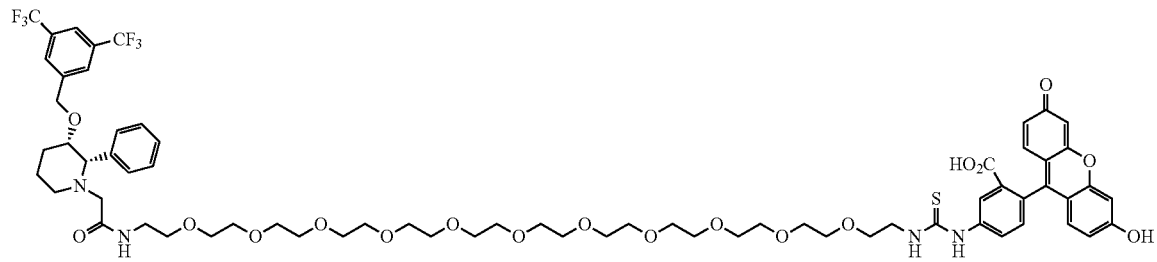 [SMILES: O=C(CN1CCC[C@H](OCc2cc(C(F)(F)F)cc(C(F)(F)F)c2)[C@@H]1c1ccccc1)NCCOCCOCCOCCOCCOCCOCCOCCOCCOCCOCCOCCNC(=S)Nc1ccc(-c2c3ccc(=O)cc-3oc3cc(O)ccc23)c(C(=O)O)c1]

To a stirred solution of NK-1 (0.02 g, 0.0433 mmol, 1.0 eq.), O-(2-Aminoethyl)-O'-[2-(Boc-amino)ethyl]decaethylene glycol (BocNH-PEG$_{11}$-NH$_2$) (Sigma, 0.0336 g, 0.0521 mmol, 1.2 eq.), Benzotriazol-1-yl-oxytripyrrolidinophosphonium hexafluorophosphate (PyBOP) (0.027 g, 0.0521 mmol, 1.2 eq.) in dry CH$_2$Cl$_2$ was added N,N-Diisopropylethylamine (DIPEA) (0.076 mL, 0.4338 mmol, 10 eq.) under argon at room temperature. The reaction progress was monitored by LCMS and purified by preparative RP-HPLC (Waters, XBridge™ Prep C18, 5 μm; 19×100 mm column, mobile phase A=20 mM ammonium acetate buffer, pH 7, B=acetonitrile, gradient 10-100% B in 30 min, 13 mL/min, λ=220 nm, 254 nm). The pure fractions were collected, all organic solvents were evaporated and the sample was lyophilized for 48 h to provide the NK1-PEG$_{11}$-NHBoc. Yield: 40.13 mg (97%). To the NK1-PEG$_{11}$-NHBoc (0.0165 g, 0.015 mmol) in dry DCM was added trifluoroacetic acid (TFA, 20 eq.) and the reaction mixture was stirred for 4 h at r.t. The excess TFA was removed, and the remaining solution was diluted with water and extracted using CH$_2$Cl$_2$ (3×5 mL). The combined organic layers were washed with brine, dried (Na$_2$SO$_4$) and concentrated. The residue obtained was dried under vacuum and used for the next-step without further purification. A stirred solution of NK1-PEG$_{11}$-NH$_2$ (0.008 g, 0.0081 mmol, 1.0 eq.), Fluorescein isothiocyanate (FITC) (Sigma, 0.0037 g, 0.0097 mmol, 1.2 eq.) in dry dimethylsulfoxide (DMSO, 0.3 mL) was added to diisopropylethyl amine (0.0028 mL, 0.0162 mmol, 2.0 eq.) at room temperature under argon. The reaction progress was monitored by LCMS and the product was purified by preparative RP-HPLC (Waters, XBridge™ Prep C18, 5 μm; 19×100 mm column, mobile phase A=20 mM ammonium acetate buffer, pH 7, B=acetonitrile, gradient 10-100% B in 30 min, 13 mL/min, λ=280 nm). The pure fractions were collected, all organic solvents were evaporated and the sample was lyophilized for 48 h to provide the FITC-PEG11-NK1 in a yield of 8.54 mg (77%).

*Note: The NK-1 compound was synthesized by a two-step procedure starting from the base ligand, which was prepared by using a procedure in the literature. (Ref: DESIGN AND DEVELOPMENT OF NEUROKININ-1 RECEPTOR-BINDING AGENT DELIVERY CONJUGATES, Application Number: PCT/US2015/44229; incorporated herein by reference.

Example 12

Synthesis of FITC-PEG2-CA9

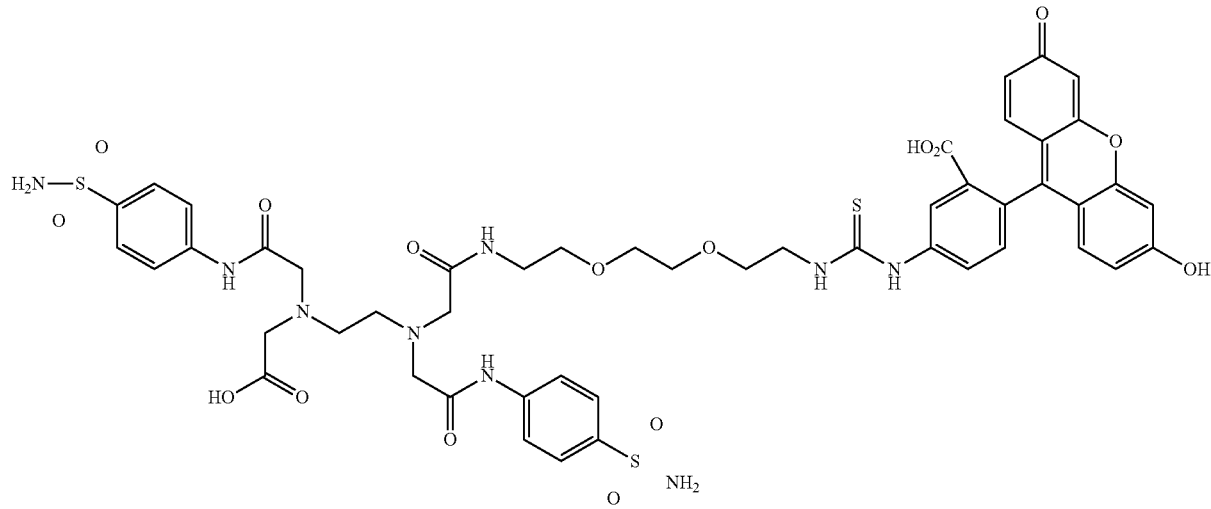

CA9 ligand (53.6 mg) was dissolved in DMF (2-3 mL) in a 50 mL round bottom flask using a Teflon magnetic stir bar. Ambient air was removed using a vacuum and replaced with nitrogen gas, this was done in three cycles. The round bottom flask was kept under constant nitrogen gas. To the flask, 28.9 mg of N-(3-Dimethylaminopropyl)-N'-ethylcarbodiimide hydrochloride (EDC) was added followed by 21.6 mg 1-Hydroxybenzotriazole hydrate (HOBt) and 18.9 µL of Boc-PEG$_2$-NH$_2$ (Sigma Aldrich). 5.4 µL of triethylamine (TEA) was added and the reaction was stirred overnight. The reaction mixture was purified using HPLC and confirmed with UHPLC-MS (target m/z of 831). Acetonitrile was removed using high vacuum rotary evaporation and the product lyopholized. The compound was mixed with 1:1 TFA:DCM for 30 minutes. The TFA/DCM was removed using high vacuum rotary evaporation followed by 30 minutes on high vacuum. The compound was then dissolved in DMF and combined with 5 molar equivalents of i-Pr$_2$NEt, 16 mg of fluorescein isothiocyanate (Life Technologies) and stirred for 1 h. The reaction mixture was purified by HPLC and the target compound was confirmed with UHPLC-MS (target m/z of 1120). The samples were lyophilized and stored at −20° C.

Example 13

Evaluation of Anti-FITC scFv Expression on Transduced CAR-T Cells

In order to confirm whether functional anti-FITC scFv is expressed on the cell surface of transduced CAR T cells, CAR T cells were incubated with FITC-Folate conjugate for 30 min on ice. After washing the cells, an anti-folate antibody (Santa Cruz) was added and incubated for 30 min on ice. Finally, Alexa Fluor 647-labeled secondary antibody (Jackson ImmunoResearch) was used to visualize CAR T cells expressing functional anti-FITC scFv. As shown in FIG. 16A, transduced CAR T cells show GFP expression. As shown in FIG. 16B, those transduced CAR-T cells can bind FITC-Folate conjugate which was visualized by immunofluorescence labeling.

Example 14

Cytotoxicity Assay of CAR T Cells In Vitro

In order to test cytotoxicity of CAR T cells with desired FITC-ligands, a standard lactate dehydrogenase (LDH) release assay was performed using a Pierce™ LDH cytotoxicity assay kit from ThermoFisher Scientific. To prepare samples for the LDH assay, cancer cells were seeded at a density of 10$^4$ cells/100 µL of media in each well of a 96 well plate and grown overnight. CAR T cells were prepared the next day at various numbers to have different effector (CAR T cell):target cell (cancer cell) ratios (e.g. E:T=20:1, 10:1, 5:1 and 1:1). FITC-ligands at various concentrations were introduced into each well and co-cultured for 6-24 hours. After co-incubation, the plate containing CAR T cells and cancer cells was centrifuged at 350×g at room temperature for 10 min to remove cell debris or remaining cells. 50 µL of the supernatants of each sample were then transferred into a new 96 well plate. 50 µL of the prepared LDH reaction mixture was added to the transferred 50 µL of each sample and incubated at room temperature for 30 min. 50 µL of stop solution was added and the absorbance of each sample was measured at 490 nm and 680 nm. The percent of cytotoxicity was calculated for each sample by using the equation below:

% Cytotoxicity=(Experimental value−effector cells spontaneous−target cells spontaneous)/(Target cell maximum control−target cell spontaneous control)×100

As shown in FIGS. 3A-C, CAR T cells are only activated when coupled with matching conjugates to tumor antigens. FIG. 3A shows the cytotoxicity of CAR T cells in a KB (FR+) model with an E:T of 10:1 using 100 nM of each conjugate. FITC-Folate, FITC-PEG20-Folate, and FITC-PEG108-Folate activation is greater than activation with FITC-DUPA or in the absence of a conjugate. FIG. 3B shows the cytotoxicity of CAR T cells in an LNCaP (PSMA+) model with an E:T of 10:1 using 100 nM FITC-DUPA or FITC-PEG12-DUPA. The FITC-DUPA conjugates show greater activation than using FITC-Folate or in the absence of a conjugate. FIG. 3C shows the cytotoxicity of CAR T cells in a HEK293 (NK1R+) model with an E:T of 10:1 using 100 nM FITC-PEG11-NK1. FITC-PEG11-NK1 shows greater than activation using FITC-Folate or in the absence of a conjugate.

As shown in FIG. 3D, CAR T cell cytotoxicity to tumor cells in a KB (FR+) model is a function of the E:T ratio used during the assay with 100 nM of FITC-Folate and FITC-DUPA. As shown in FIG. 3E, CAR T cell cytotoxicity to tumor cells in a KB (FR+) model is a function of the concentration of FITC-Folate used during the co-incubation (E:T ratio of 10:1).

As shown in FIG. 10, CAR T cytotoxicity in a KB (FR+) model can be controlled by adjusting concentration of the conjugate bridge, or using linkers with different lengths of PEG with a E:T of 10:1.

Example 15

Identification of CAR T Cell Proliferation and CAR T Cell Activation

CAR T cell proliferation was mainly measured by flow cytometry. First, cancer cells (KB (FR+) or HEK (NK1R+)) were seeded at density of 10$^4$ cells/100 µL of media in each well of a 96 well plate and grown overnight. The next day, CAR T cells were introduced into each well in either the presence or absence of the desired FITC-ligands and the cells were co-cultured for 5 days (120 hours). After co-incubation, CAR T cells were stained with anti-human CD3 APC antibody (Biolegend) by standard immunostaining procedures (20 min on ice). Cells positive for both anti-human CD3 staining and GFP were counted for CAR T cell proliferation.

As shown in FIG. 1A-B, CAR T cells were proliferated as a result of targeting the tumor cells (E:T=5:1) with FITC-small molecular conjugate (100 nM) using KB (FR+) cells and HEK293 (NK1R+) cells. FIG. 1A shows CAR T cell proliferation in the presence of KB (FR+) cells with different conjugates. FIG. 1B shows CAR T cell proliferation in the presence of HEK (NK1R+) cells with different conjugates. As can be further seen in FIG. 1, the presence of linkers with different lengths of PEG affect the levels of CAR-T cell proliferation.

Figure 17:
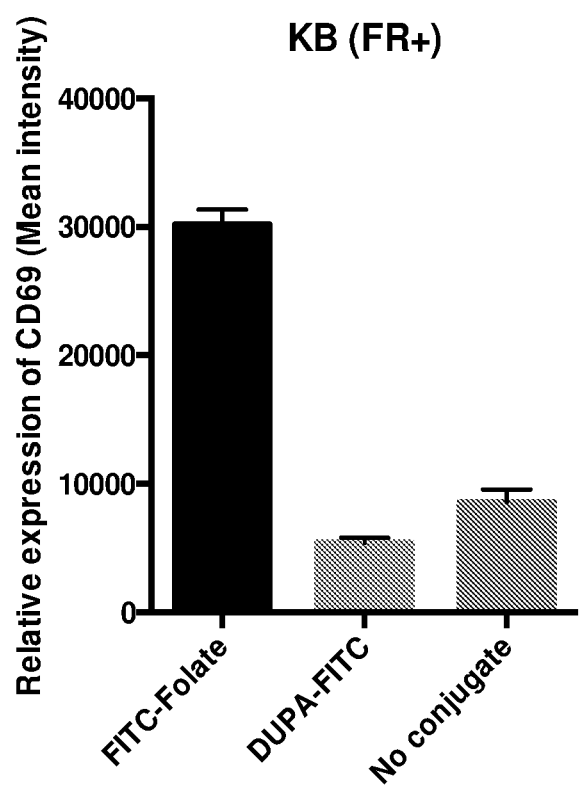
FIG. 17 shows activation of CAR T cells as measured by relative expression of CD69 as a function of the conjugate used.
Figure 18:
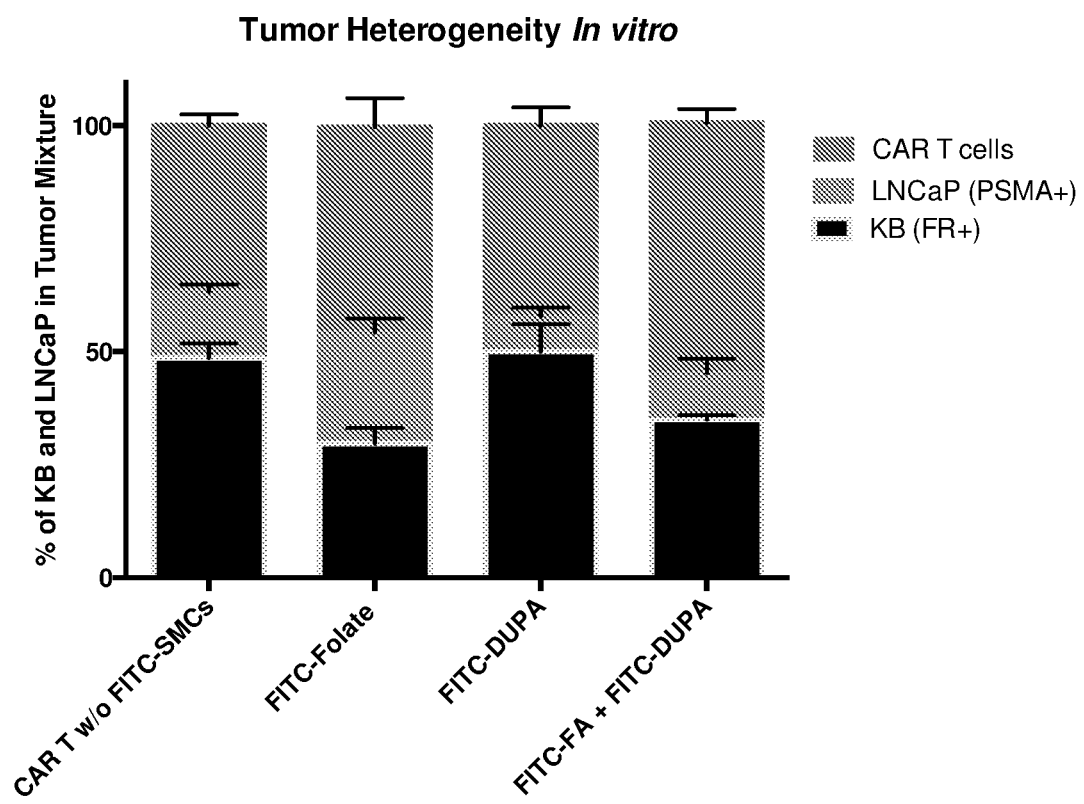
FIG. 18 shows tumor heterogeneity of KB, LNCaP, and CAR T cells as a function of the conjugate used.

To measure CAR T cell activation, cancer cells were prepared by the same procedure described above. Cancer cells and CAR T cells were co-cultured in the presence or absence of 100 nM FITC-ligands with an E:T ratio of 10:1 for 24 hours and harvested. After washing, cells from each sample were stained with anti-human CD69 Alexa Fluor 647 (Biolegend). Data was analyzed in the gate of GFP positive T cells in order to quantify CAR T cell activation. As shown in FIG. 17, CD69 expression is related to the co-cultured conjugate.

Example 16

IFN-γ Production Assay

To test production of IFN-γ by CAR T cells, a standard ELISA assay was performed using a Human IFN-γ detection ELISA kit from Biolegend. Briefly, cancer cells were seeded at density of $10^4$ cells/100 µL of media in each well of a 96 well plate and grown overnight. CAR T cells were introduced into each cancer sample with desired FITC-ligands and co-cultured for 24 hours. After co-incubation, supernatants of each sample were harvested and centrifuged at 1000×g and 4° C. for 10 min to remove cell debris. Clear supernatants from each sample were then either used to detect IFN-γ by ELISA or stored at −80° C. for future usage. After completing preparation of each sample, standard ELISA was performed based on the manufacturer's instructions.

As shown in FIGS. 2A-C, with an E:T ratio of 5:1 in KB cells(FR+) (FIG. 2A), LNCaP (PSMA+) (FIG. 2B), or HEK (NK1R+) (FIG. 2C) CAR T cells produce a significant amount of inflammatory cytokine in the presence of 100 nM FITC-small molecular conjugate. As can be further seen, the amount of cytokine is dependent on the conjugate used. As shown in FIG. 2D, the amount of inflammatory cytokine is related to the concentration of FITC-Folate used with KB (FR+) cells. As shown in FIGS. 2E and 2F, the different conjugates (100 nM) produce different IFN-γ responses with KB (FR+) cells.

As shown in FIGS. 4A-B, activation of CAR T cells is correlated with the tumor antigen level in KB (FR+) cells and MDA-MB-231 cells. Measuring IFN-γ production from incubating the cells with same the conjugate dose shows that activation of anti-FITC CAR T cells is correlated with the expression level of tumor antigen on cancer cells.

Example 17

Evaluation of Correlation Between Tumor Antigen Level and CAR-T Activation

KB (FR+) cells and MDA-MB-231 cells were incubated with 100 nM FITC-folate for 30 min on ice. After washing, FITC-folate binding to FRα tumor antigen on cells was measured by flow cytometry. As shown in FIG. 4A, KB (FR+) cells have a higher level of FR expression and corresponding FITC binding than MDA-MB-231 cells.

These two cell lines were co-cultured with CAR T cells in the presence of 100 nM FITC-Folate, FITC-PEG20-Folate and FITC-PEG108-Folate with an E:T ratio of 10:1 for 24 hours. CAR T cell activation was detected by measuring its INF-γ production. The supernatant of the cultured cells was harvested and the IFN-γ production was measured using an ELISA kit. As shown in FIG. 4B, with higher FRα level, KB cells (FR+) cells activated CAR T cells much better than MDA-MB-231 cells.

Example 18

Anti-Tumor Efficacy of CAR T Cells In Vivo

Immunodeficient NSG mice (Jackson Laboratory) were used to identify the efficacy of CAR T cell anti-tumor activity in vivo. Each tumor-specific antigen expressing cancer cell line was subcutaneously injected into the shoulder of NSG mice to establish solid tumor xenografts. When tumor volume of around 50-100 $mm^3$ was reached, CAR T cells were introduced into mice bearing tumors and desired FITC-ligands were also introduced (i.v.) every other day. Control mice were administered PBS instead of FITC-ligands. Tumor volume and cytokine levels in the blood (IL2, IL6, IL10, IFNγ, and TNFα) were measured. General toxicity of the therapy was monitored by measuring weight loss. At the end of each treatment, mouse blood was collected to test for anemia, number of white blood cells and CAR T cell proliferation. Mouse organs were also evaluated.

A xenograft model using HEK293 (NK1R+) cells is shown in FIGS. 5A-C and 6A-B. As shown in FIG. 5A, tumor size decreased in the mice treated with FITC-PEG11-NK1 (500 nmol/kg) but continued to grow in the control mouse. As shown in FIG. 5B, the body weight of mice treated with FITC-PEG11-NK1 was unchanged relative to the control mouse. As shown in FIG. 5C, the percentage of CAR T cells in human T cells increased after CAR T cell injection. As shown in FIGS. 6A-B, harvested organs from the treatment group (6B) appeared normal in size with no indications of cytokine release syndrome after two weeks of therapy when compared to the harvested mouse organs from a control group (6A).

A xenograft model using MDA-MB-231 (FR+) cells is shown in FIGS. 7A-C and 8A-B. As shown in FIG. 7A, tumor size decreased in the mice treated with FITC-PEG12-Folate (500 nmol/kg) or FITC-Folate (500 nmoles/kg) but tumors continued to grow in the control mouse. As shown in FIG. 7B, the body weight of mice treated with FITC-PEG11-NK1 was unchanged during treatment. As shown in FIG. 7C, the percentage of CAR T cells in human T cells increased after CAR T cell and conjugate therapy. As shown in FIGS. 8A-B, harvested organs from the mice treated with FITC-PEG12-Folate (8B) appeared normal in size and no indication of cytokine release syndrome was observed after 3 weeks of therapy when compared to the harvested mouse organs from a control group (8A). As used in any of the embodiments in this patent application, "nmol/kg" and "nmoles/kg" are equivalent.

As shown in FIG. 9, blood indices of the HEK-NK1R model using FITC-PEG11-NK1 (500 nmoles/kg) and the MDA-MB-231 model using FITC-PEG12-Folate (500 nmoles/kg) also indicated that a cytokine storm had not occurred during the course of the treatment.

Figure 11:
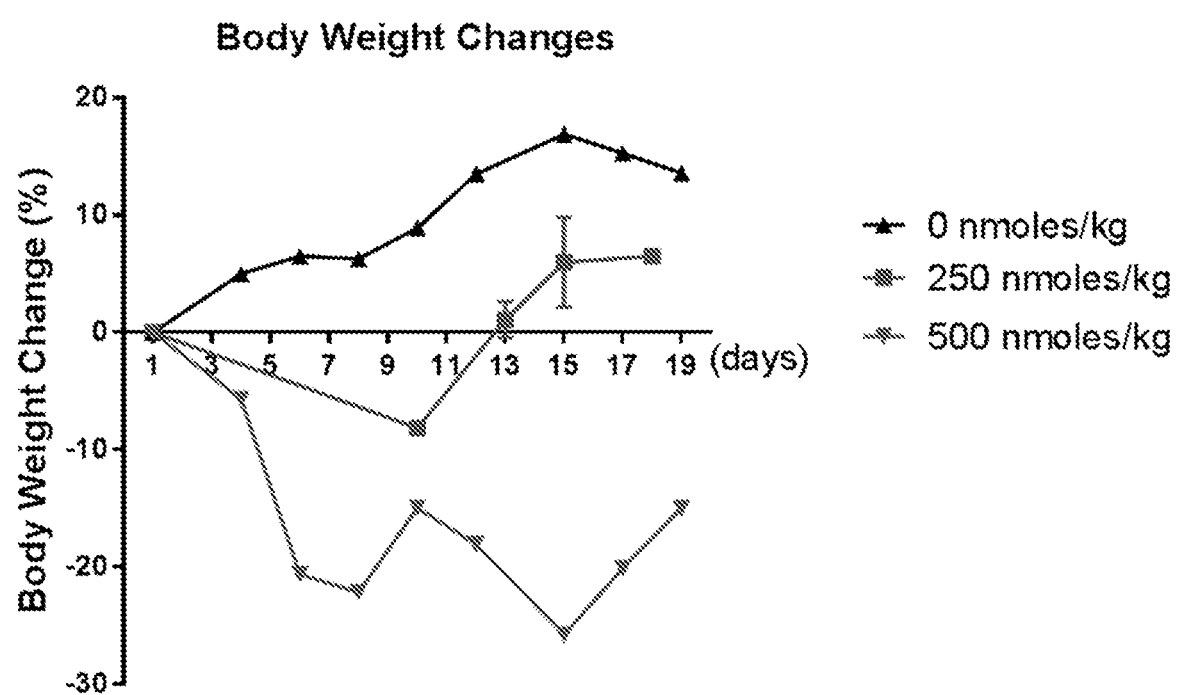
FIG. 11 shows body weight percentage change in a KB tumor xenograft model using CAR T cells with different concentrations of a FITC-PEG-12-Folate conjugate.
Figure 12:
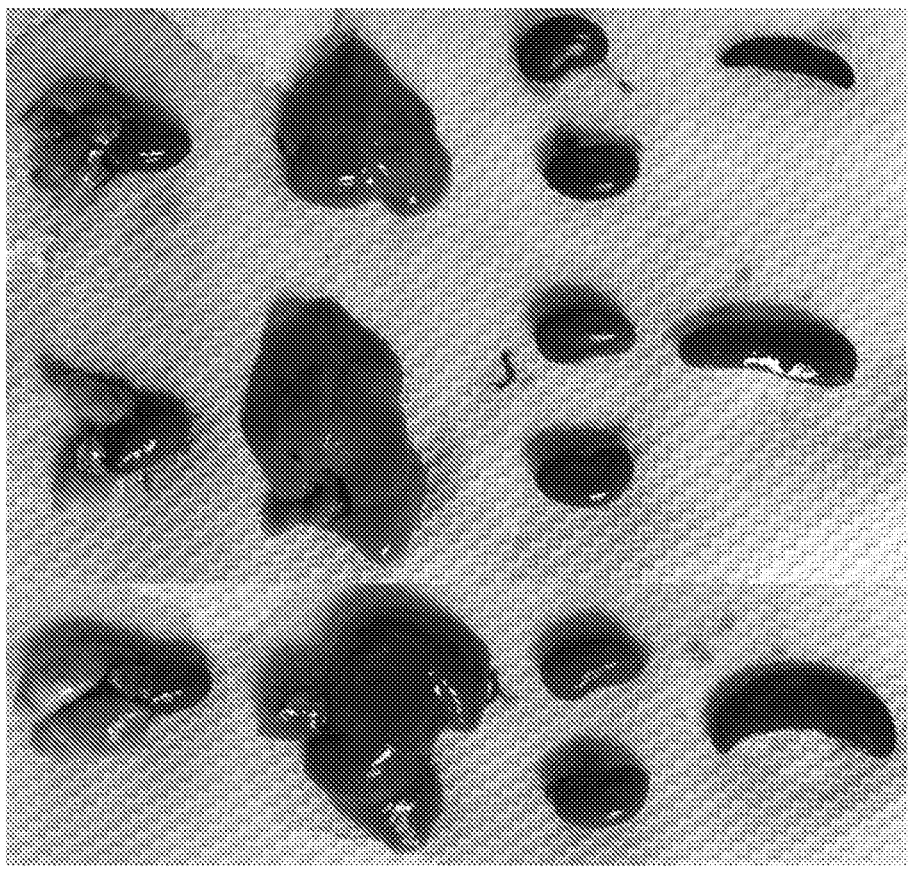
FIGS. 12A-C show harvested organs from exemplary mice of the KB xenograft model shown in FIG. 11.

As shown in FIGS. 11, 12A-C, and 13, KB (FR+) tumor xenografts were treated with two difference concentrations of FITC-PEG12-Folate. As shown in FIG. 11, the mice treated with the lower dose (250 nmoles/kg) had milder body weight loss compared to the mice treated with a higher dose (500 nmoles/kg). As shown in FIGS. 12A-C, harvested organs from untreated mice (FIG. 12A) and mice receiving the lower dose (FIG. 12B) showed milder cytokine release syndrome compared to the higher dose (FIG. 12C). As shown in FIG. 13, KB xenograft mice receiving lower dosing showed better blood indices indicating milder cytokine release.

Example 19

Anti-Tumor Efficacy of CAR T Cells In Vivo

In order to study whether same anti-FITC CAR T cell can eradicate mixture of heterogeneous cancer cells with cocktail of FITC-ligands, immunodeficient NSG mice (Jackson laboratory) were utilized for the in vivo study. Two different cancer cell lines (e.g. MDA-MB-231(FR+) and HEK (NK1R+)) were implanted into separate flanks on the same mouse. Then, anti-FITC CAR T cell ($10^7$ cells) was introduced by intravenous injection when tumor volumes reached about 50-100 mm$^3$. In addition, either a mixture of FITC-ligands (i.e. FITC-PEG12-Folate (500 nmole/kg) and FITC-PEG11-NK1R (500 nmole/kg)), single FITC-PEG11-NK-1R (500 nmole/kg) or PBS was introduced every other day by intravenous injection. The anti-tumor efficacy of CAR T cell with FITC-ligands was analyzed by measuring tumor volume at every other day.

As shown in the FIGS. 19A-C, both tumors (i.e. MDA-MB-231 (MDA) and HEK (NK1R)) were eliminated by the same anti-FITC CAR T cell when both FITC-PEG11-NK1R and FITC-PEG12-Folate were introduced. Only HEK (NK1R) tumor was eradicated in the mouse that was treated by only FITC-PEG11-NK1R. Without being bound by theory, it is believed that the MDA-MB-231 continued growing in the same mouse where only FITC-PEG11-NK1R was administered because FITC-PEG12-Folate was not administrated. As expected, both tumors did not show any response when PBS was introduced. These data suggest that the same anti-FITC CAR T cell can eradicate antigenically heterogamous tumor mixture though cocktail of FITC-ligands.

What is claimed is:

1. A method of treating a patient for cancer, the method comprising:
   administering to the patient a chimeric antigen receptor T cell (CAR T cell) composition, wherein the CAR T cell comprises a chimeric antigen receptor (CAR) directed to fluorescein isothiocyanate (FITC), and
   administering to the patient an effective amount of a first conjugate, or a pharmaceutically acceptable salt thereof, wherein the first conjugate comprises an NK-1 receptor-binding ligand (NK1RL) and FITC,
   wherein the NK1RL is a small molecule comprising

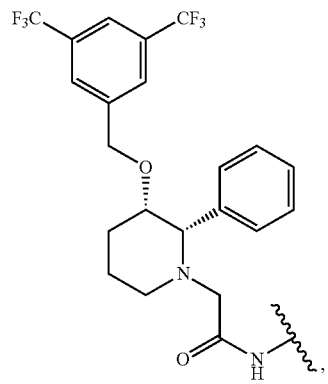 [SMILES: *NC(=O)CN1CCC[C@H](OCc2cc(C(F)(F)F)cc(C(F)(F)F)c2)[C@@H]1c1ccccc1]

wherein the CAR T cell comprises a nucleic acid comprising SEQ ID NO: 1 or SEQ ID NO: 3,
   wherein the cancer is an NK-1 receptor-expressing cancer, and
   wherein the patient is treated for cancer.

2. The method of claim 1, further comprising administering to the patient an effective amount of a second conjugate, or a pharmaceutically acceptable salt thereof, wherein the second conjugate comprises a folate and FITC.

3. The method of claim 2, wherein the first conjugate comprises a first divalent linker covalently bound to FITC and covalently bound to the NK1RL, and the second conjugate comprises is a second divalent linker covalently bound to FITC and covalently bound to the folate.

4. The method of claim 3, wherein the first divalent linker and the second divalent linker each comprises polyethylene glycol (PEG).

5. The method of claim 2, wherein the second conjugate is:

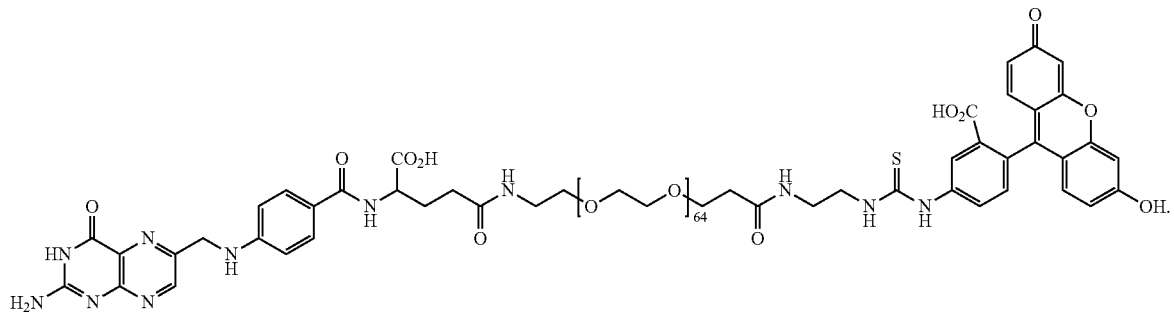

6. The method of claim 1, wherein the cancer comprises a folate receptor-expressing cancer.

7. The method of claim 1, wherein the first conjugate is:

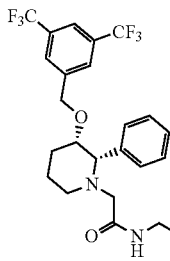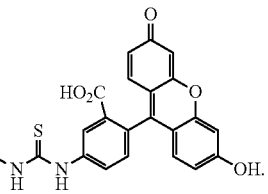

8. A method of treating a patient for cancer, the method comprising:
   administering to the patient a chimeric antigen receptor T cell (CAR T cell) composition, wherein the CAR T cell comprises a chimeric antigen receptor (CAR) directed to fluorescein isothiocyanate (FITC), and
   administering to the patient an effective amount of a first conjugate, or a pharmaceutically acceptable salt thereof, wherein the first conjugate comprises an NK-1 receptor-binding ligand (NK1RL) and FITC,
   wherein the NK1RL is a small molecule comprising

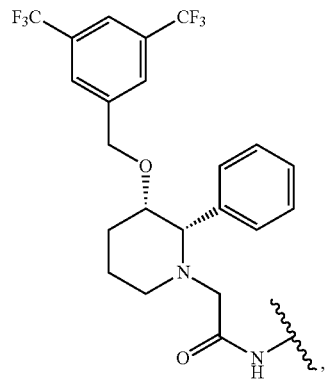 [SMILES: *NC(=O)CN1CCC[C@H](OCc2cc(C(F)(F)F)cc(C(F)(F)F)c2)[C@@H]1c1ccccc1]

wherein the CAR T cell comprises a polypeptide comprising SEQ ID NO: 2,
wherein the cancer is an NK-1 receptor-expressing cancer, and
wherein the patient is treated for cancer.

9. The method of claim 8, further comprising administering to the patient an effective amount of a second conjugate, or a pharmaceutically acceptable salt thereof, wherein the second conjugate comprises a folate and FITC.

10. The method of claim 9, wherein the first conjugate comprises a first divalent linker covalently bound to FITC and covalently bound to the NK1RL, and the second conjugate comprises is a second divalent linker covalently bound to FITC and covalently bound to the folate.

11. The method of claim 10, wherein the first divalent linker and the second divalent linker each comprises polyethylene glycol (PEG).

12. The method of claim 9, wherein the second conjugate is:

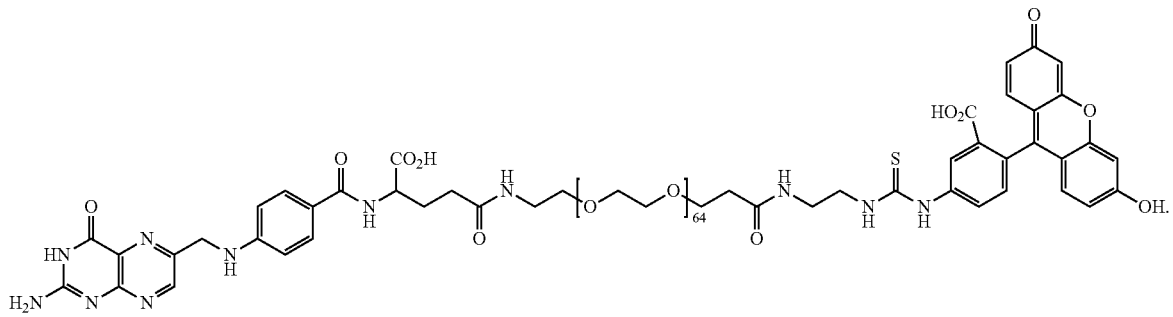

13. The method of claim 8, wherein the first conjugate is:

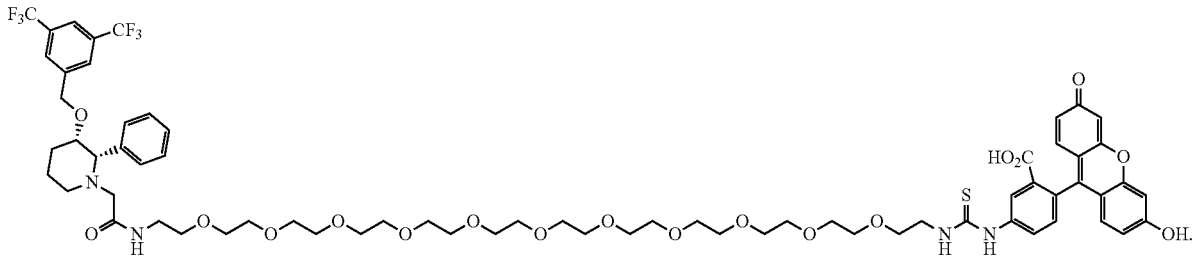 [SMILES: O=C(CN1CCC[C@H](OCc2cc(C(F)(F)F)cc(C(F)(F)F)c2)[C@@H]1c1ccccc1)NCCOCCOCCOCCOCCOCCOCCOCCOCCOCCOCCOCCNC(=S)Nc1ccc(-c2c3ccc(=O)cc-3oc3cc(O)ccc23)c(C(=O)O)c1]

14. The method of claim 8, wherein the cancer comprises a folate receptor-expressing cancer.

* * * * *

UNITED STATES PATENT AND TRADEMARK OFFICE
CERTIFICATE OF CORRECTION

PATENT NO. : 12,144,850 B2
APPLICATION NO. : 16/092054
DATED : November 19, 2024
INVENTOR(S) : Low et al.

Page 1 of 1

It is certified that error appears in the above-identified patent and that said Letters Patent is hereby corrected as shown below:

On the Title Page

On page 6, in Column 1, under "Other Publications", Line 6, delete "AnalyticalTechniques,"" and insert --Analytical Techniques,"-- therefor On page 6, in Column 2, under "Other Publications", Line 16, delete "receptor-a" and insert --receptor-α-- therefor On page 10, in Column 1, under "Other Publications", Line 43, delete "Foell" and insert --Focll-- therefor On page 10, in Column 2, under "Other Publications", Line 70, delete "Bel-x" and insert --Bcl-x-- therefor On page 11, in Column 1, under "Other Publications", Line 35, delete "effec"" and insert --effect"-- therefor In the Claims In Column 71, Line 10, in Claim 8, delete "(NKIRL)" and insert --(NK1RL)-- therefor Signed and Sealed this
Twenty-seventh Day of January, 2026

John A. Squires
*Director of the United States Patent and Trademark Office*